(12) United States Patent
Sakai et al.

(10) Patent No.: US 8,586,505 B2
(45) Date of Patent: Nov. 19, 2013

(54) 4-(3-BUTYNYL)AMINOPYRIMIDINE DERIVATIVES AS PEST CONTROL AGENTS FOR AGRICULTURAL AND HORTICULTURAL USE

(75) Inventors: Masaaki Sakai, Tsukuba (JP); Tomoaki Matsumura, Tsukuba (JP); Satohiro Midorikawa, Tsukuba (JP); Takashi Nomoto, Tsukuba (JP); Ryutaro Katsuki, Tsukuba (JP); Tomoko Muraki, Tsukuba (JP)

(73) Assignee: SDS Biotech K. K., Tokyo (JP)

( * ) Notice: Subject to any disclaimer, the term of this patent is extended or adjusted under 35 U.S.C. 154(b) by 30 days.

(21) Appl. No.: 13/378,866

(22) PCT Filed: Jul. 15, 2010

(86) PCT No.: PCT/JP2010/061993
§ 371 (c)(1),
(2), (4) Date: Feb. 17, 2012

(87) PCT Pub. No.: WO2011/007839
PCT Pub. Date: Jan. 20, 2011

(65) Prior Publication Data
US 2012/0136150 A1    May 31, 2012

(30) Foreign Application Priority Data

Jul. 16, 2009 (JP) ................... 2009-168286
Apr. 27, 2010 (JP) ................... 2010-101951

(51) Int. Cl.
| | |
|---|---|
| *C07D 239/42* | (2006.01) |
| *C07D 239/94* | (2006.01) |
| *C07D 417/12* | (2006.01) |
| *C07D 487/04* | (2006.01) |
| *C07D 495/04* | (2006.01) |
| *A01N 43/90* | (2006.01) |
| *A01N 47/02* | (2006.01) |
| *A01N 47/24* | (2006.01) |
| *A01N 55/00* | (2006.01) |

(52) U.S. Cl.
USPC ........... 504/239; 504/240; 504/241; 514/257; 514/258.1; 514/260.1; 514/262.1; 514/263.4; 514/264.11; 514/265.1; 514/266.1; 544/249; 544/264; 544/278; 544/279; 544/280; 544/283; 544/326

(58) Field of Classification Search
USPC ......... 544/249, 264, 278, 279, 280, 283, 326; 514/257, 258, 260.1, 262.1, 263.4, 514/264.11, 265.1, 266.1; 504/239, 240, 504/241
See application file for complete search history.

(56) References Cited

U.S. PATENT DOCUMENTS 4,146,716 A * 3/1979 Cox et al. ............... 544/278

FOREIGN PATENT DOCUMENTS

| EP | 1074546 A1 | 2/2001 |
|---|---|---|
| JP | 05-230036 | 9/1993 |
| JP | 06-025187 | 2/1994 |
| JP | 08-113564 | 5/1996 |
| JP | 11-158161 | 6/1999 |
| JP | 11-302261 | 11/1999 |
| JP | 2006-008542 | 1/2006 |
| WO | WO 03/076415 A1 | 9/2003 |
| WO | WO 2004/087706 A1 | 10/2004 |
| WO | WO 2006/047397 A1 | 5/2006 |
| WO | WO 2007/046809 A1 | 4/2007 |
| WO | WO 2007/135029 A1 | 11/2007 |

OTHER PUBLICATIONS

Chesterfield, J. et al., (1955), "Pyrimidines. Part VIII. Halogeno- and Hydrazino-pyrimidines," Journal of the Chemical Society, pp. 3478-3481.
Extended European Search Report mailed Dec. 20, 2012 in EP Appln. No. 10799897.3.

* cited by examiner

*Primary Examiner* — Bruck Kifle
(74) *Attorney, Agent, or Firm* — Swanson & Bratschun, L.L.C.

(57) ABSTRACT

Novel 4-(3-butynyl)aminopyrimidine derivatives represented by general formula [I] are useful as pest control agents. In general formula [I], $R^1$ is a mono- or bi-cyclic ring which may contain 0 to 3 heteroatoms, for example, phenyl or oxazolyl; $R^2$ is a hydrogen atom, —R, —OR, —C(O)OR, —C(O)NHR, —CONR$_2$ (wherein R is straight-chain or branched $C_{1-8}$ alkyl, or the like), hydroxyalkyl, or the like; $R^3$ is a hydrogen atom, a halogen atom, acyloxy represented by (straight-chain or branched $C_{1-8}$ aliphatic hydrocarbon group) —CO—O—, or the like; and $R^4$ is a hydrogen atom, a halogen atom, $C_{1-6}$ alkyl, or the like, or alternatively, $R^4$ and $R^3$ together with the carbon atoms on the pyrimidine ring may form a thiophene ring, a pyrrole ring, an imidazole ring, a benzene ring, a pyrimidine ring, a furan ring, a pyrazine ring, or a pyrrolidine ring.

8 Claims, No Drawings

4-(3-BUTYNYL)AMINOPYRIMIDINE DERIVATIVES AS PEST CONTROL AGENTS FOR AGRICULTURAL AND HORTICULTURAL USE

CROSS-REFERENCE TO RELATED APPLICATIONS

This application is a 35 USC §371 of PCT Application Serial No. PCT/JP2010/061993, filed Jul. 15, 2010, currently pending, entitled "4-(3-Butynyl)Aminopyrimidine Derivatives as Pest Control Agents for Agricultural and Horticultural Use," which claims priority to Japanese Patent Application No. 2009-168286, filed Jul. 16, 2009, and Japanese Patent Application No. 2010-101951, filed Apr. 27, 2010, which are each incorporated herein in their entirety by reference.

TECHNICAL FIELD

The present invention relates to a novel 4-(3-butynyl)aminopyrimidine derivative useful as a pest control agent, and in particular, as a pest control agent for agricultural and horticultural use.

BACKGROUND ART

To date, various aminopyrimidine derivatives having pest control activity have been known. Please refer to the citation list as set forth below for some examples of such aminopyrimidine derivatives.

In recent years, however, a decrease in medicinal effects due to the development of drug resistance to pest control agents has caused a serious problem. Thus, it has been still desired to develop a novel compound which will be used instead of conventional aminopyrimidine compounds having pest control activity. The 4-(3-butynyl)aminopyrimidine derivative of the present invention is a novel compound, and it has not been known that this compound has activity of controlling agricultural and horticultural pests.

PRIOR ART DOCUMENTS

Patent Documents

Patent Document 1: Japanese Patent Laid-Open No. 5-230036
Patent Document 2: Japanese Patent Laid-Open No. 6-25187
Patent Document 3: Japanese Patent Laid-Open No. 8-113564
Patent Document 4: Japanese Patent Laid-Open No. 11-302261
Patent Document 5: Japanese Patent Laid-Open No. 11-158161
Patent Document 6: Japanese Patent Laid-Open No. 2006-8542
Patent Document 7: WO2007/135029
Patent Document 8: WO2007/46809
Patent Document 9: WO2006/47397

Non-Patent Documents

Non-Patent Document 1: Journal of the Chemical Society, 1995, pp. 3478-3481

SUMMARY OF THE INVENTION

Problems to be Solved by the Invention

It is an object of the present invention to provide a novel 4-(3-butynyl)aminopyrimidine derivative, a method for producing the same, and a pest control agent for agricultural and horticultural use, which comprises the 4-(3-butynyl)aminopyrimidine derivative as an active ingredient.

Means for Solving the Problems

As a result of intensive studies directed towards achieving the aforementioned object, the present inventors have found that a 4-(3-butynyl)aminopyrimidine derivative that is a novel compound has significant activity of killing agricultural and horticultural insects, mites, nematodes and fungi, and they have completed the present invention based on such findings.

That is to say, the present invention is as follows.

A first invention relates to a 4-(3-butynyl)aminopyrimidine derivative represented by the following general formula [I]:

[Formula 1]

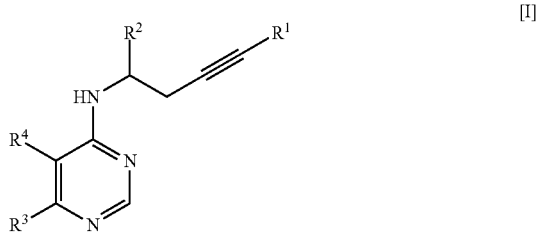

[I]

[wherein
$R^1$ is selected from among
a) a mono- or bi-cyclic ring which may contain 0 to 3 heteroatoms selected from the group consisting of phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolinyl, pyridyl, quinolyl, isoquinolyl, benzothiazolyl, benzoisothiazolyl, pyrrolyl, indolyl, isoindolyl, benzoxazolyl, benzisoxazolyl, thienyl, benzothienyl, imidazolyl, benzimidazolyl, pyrazolyl, and pyridonyl,
b) linear or branched alkyl containing 1 to 6 carbon atoms, linear or branched alkenyl containing 2 to 8 carbon atoms, linear or branched alkynyl containing 2 to 8 carbon atoms, cycloalkyl containing 3 to 8 carbon atoms, or cycloalkenyl containing 3 to 8 carbon atoms,
c) —SiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), and
d) a hydrogen atom, wherein
in the case of a) or b) above, $R^1$ may be substituted with —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), —SiR$^5$R$^6$R$^7$, —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), haloalkyl (a linear or branched alkyl group containing 1 to 4 carbon atoms which is identically or differently substituted with 1 to 9 halogen atoms), haloalkenyl (a linear or branched alkenyl group containing 2 to 6 carbon atoms which is identically or differently substituted with 1 to 4 halogen atoms), haloalkoxy (a linear or branched alkoxy group containing 1 to 4 carbon atoms which is identically or differently substituted with 1 to 9 halogen atoms), acylalkoxy (a linear or branched alkoxy group containing 1 to 3 carbon atoms which is substituted with 1 to 2 acyl groups represented by —CO— (a linear or branched aliphatic hydrocarbon group containing 1 to 8 carbon atoms)), acyloxyalkyl (a linear or branched alkyl group containing 1 to 3 carbon atoms which is substituted with an acyloxy group represented by 1 to 2 (a linear or branched aliphatic hydrocarbon group containing 1 to 8 carbon atoms)-CO—O— groups, alkylsulfonylalkyl (a linear or branched alkyl group containing 1 to 3 carbon atoms which is substituted with 1 to 2 linear or branched alkylsulfonyl groups containing 1 to 8 carbon atoms), siloxyalkyl (a linear or branched alkyl group containing 1 to 3 carbon atoms which is substituted with —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents)), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with 1 to 2 linear or branched alkoxy groups containing 1 to 8 carbon atoms), haloalkoxyalkyl (a linear or branched alkyl group containing 1 to 3 carbon atoms substituted with 1 to 2 linear or branched haloalkoxy groups containing 1 to 4 carbon atoms which is identically or differently substituted with 1 to 9 halogen atoms), alkylthioalkyl (a linear or branched alkyl group containing 1 to 3 carbon atoms which is substituted with 1 to 2 linear or branched alkylthio groups containing 1 to 8 carbon atoms), dialkoxyacetal (a dialkoxymethyl group in which two linear or branched alkoxy groups each containing 1 to 8 carbon atoms are substituted with methyl groups), alkoxyalkoxy (a linear or branched alkyl group containing 1 to 3 carbon atoms which is substituted with 1 to 2 linear or branched alkoxy groups containing 1 to 8 carbon atoms), cyanoalkyl (a linear or branched alkyl group containing 1 to 3 carbon atoms which is substituted with 1 to 2 cyano groups), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine, R$^2$ represents a hydrogen atom, —R, —OR, —C(O)OR, —C(O)NHR, —CONR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with 1 to 2 linear or branched alkoxy groups containing 1 to 8 carbon atoms), haloalkoxyalkyl (a linear or branched alkyl group containing 1 to 3 carbon atoms substituted with 1 to 2 linear or branched haloalkoxy groups containing 1 to 4 carbon atoms which is identically or differently substituted with 1 to 9 halogen atoms), phenyl, heteroaryl, halogen, cyano, haloalkyl (a linear or branched alkyl group containing 1 to 4 carbon atoms which is substituted with 1 to 9 halogen atoms), or haloalkoxy (a linear or branched alkoxy group containing 1 to 4 carbon atoms which is identically or different substituted with 1 to 9 halogen atoms), R$^3$ represents (1) a hydrogen atom, (2) a halogen atom, (3) alkyl containing 1 to 6 carbon atoms substituted with acyloxy represented by 1 to 2 (a linear or branched aliphatic hydrocarbon group containing 1 to 8 carbon atoms)-CO—O— groups, 1 to 13 halogen atoms, or 1 to 4 hydroxyl groups, (4) unsubstituted alkyl containing 1 to 6 carbon atoms, (5) —OR, —SR, or —SO$_2$R (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), or (6) haloalkyl (a linear or branched alkyl group containing 1 to 4 carbon atoms which is identically or different substituted with 1 to 9 halogen atoms), and R$^4$ represents a hydrogen atom, a halogen atom, alkyl containing 1 to 6 carbon atoms, nitro, amino, phenyl, benzyl, or a thiophene ring, a pyridine ring, a pyrrole ring, an imidazole ring, a benzene ring, a naphthalene ring, a pyrimidine ring, a furan ring, a pyrazine ring, a pyrazole ring or an oxazole ring, which is formed together with a carbon atom on a pyrimidine ring as a result of binding with R$^3$].

In addition, a second invention relates to a method for producing the 4-(3-butynyl)aminopyrimidine derivative represented by general formula [I].

Moreover, a third invention relates to a pest control agent comprising, as active ingredient(s), one or two or more of the 4-(3-butynyl)aminopyrimidine derivatives represented by the general formula [I].

Advantageous Effects of Invention

The novel 4-(3-butynyl)aminopyrimidine derivative represented by the general formula [I] of the present invention has an excellent control effect on pests, and particularly, on agricultural and horticultural pests.

DESCRIPTION OF EMBODIMENTS

Hereinafter, the present invention will be described in detail.

The above described 4-(3-butynyl)aminopyrimidine derivative of the present invention includes the salts thereof (a sodium salt, a potassium salt, a magnesium salt, a calcium salt, an aluminum salt, etc.), and substances such as a hydrate, a solvate and a crystalline polymorphism, as well as the 4-(3-butynyl)aminopyrimidine derivative represented by the general formula [I]. Moreover, the compound of the present invention (the 4-(3-butynyl)aminopyrimidine derivative represented by the general formula [I]) also includes all possible stereoisomers, optical isomers, and mixtures comprising two or more such isomers at any given ratio.

Various substituents represented by the above described compound [I] are as follows.

R$^1$ is a substituent selected from any one of the following a) to d).

a) A group having, as a bond, any given ring atom (a carbon atom or heteroatom) that constitutes a mono- or bi-cyclic ring which may contain 0 to 3 heteroatoms selected from the group consisting of phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolinyl, pyridyl, quinolyl, isoquinolyl, benzothiazolyl, benzoisothiazolyl, pyrrolyl, indolyl, isoindolyl, benzoxazolyl, benzisoxazolyl, thienyl, benzothienyl, imidazolyl, benzimidazolyl, pyrazolyl, and pyridonyl.

b) Linear or branched alkyl containing 1 to 6 carbon atoms, linear or branched alkenyl containing 2 to 8 carbon atoms, linear or branched alkynyl containing 2 to 8 carbon atoms, cycloalkyl containing 3 to 8 carbon atoms, or cycloalkenyl containing 3 to 8 carbon atoms.

c) —SiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents).

d) A hydrogen atom.

In the case of a) or b) above, R$^1$ may be substituted with —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), —SiR$^5$R$^6$R$^7$, —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), haloalkyl (a linear or branched alkyl group containing 1 to 4 carbon atoms which is identically or differently substituted with 1 to 9 halogen atoms), haloalkenyl (a linear or branched alkenyl group containing 2 to 6 carbon atoms which is identically or differently substituted with 1 to 4 halogen atoms), haloalkoxy (a linear or branched alkoxy group containing 1 to 4 carbon atoms which is identically or differently substituted with 1 to 9 halogen atoms), acylalkoxy (a linear or branched alkoxy group containing 1 to 3 carbon atoms which is substituted with 1 to 2 acyl groups represented by —CO— (a linear or branched aliphatic hydrocarbon group containing 1 to 8 carbon atoms)), acyloxyalkyl (a linear or branched alkyl group containing 1 to 3 carbon atoms which is substituted with 1 to 2 acyloxy groups represented by (a linear or branched aliphatic hydrocarbon group containing 1 to 8 carbon atoms)-CO—O—), alkylsulfonylalkyl (a linear or branched alkyl group containing 1 to 3 carbon atoms which is substituted with 1 to 2 linear or branched alkylsulfonyl groups containing 1 to 8 carbon atoms), siloxyalkyl (a linear or branched alkyl group containing 1 to 3 carbon atoms which is substituted with —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents)), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with a linear or branched alkoxy group containing 1 to 8 carbon atoms), haloalkoxyalkyl (a linear or branched alkyl group containing 1 to 3 carbon atoms substituted with a linear or branched haloalkoxy group containing 1 to 4 carbon atoms which is identically or differently substituted with 1 to 9 halogen atoms), alkylthioalkyl (a linear or branched alkyl group containing 1 to 3 carbon atoms which is substituted with 1 to 2 linear or branched alkylthio groups containing 1 to 8 carbon atoms), dialkoxyacetal (a dialkoxymethyl group in which two linear or branched alkoxy groups each containing 1 to 8 carbon atoms are substituted with methyl groups), alkoxyalkoxy (a linear or branched alkyl group containing 1 to 3 carbon atoms which is substituted with 1 to 2 linear or branched alkoxy groups containing 1 to 8 carbon atoms), cyanoalkyl (a linear or branched alkyl group containing 1 to 3 carbon atoms which is substituted with 1 to 2 cyano groups), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine.

R$^2$ represents a hydrogen atom, —R, —OR, —C(O)OR, —C(O)NHR, —CONR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with 1 to 2 linear or branched alkoxy groups containing 1 to 8 carbon atoms), haloalkoxyalkyl (a linear or branched alkyl group containing 1 to 3 carbon atoms substituted with 1 to 2 linear or branched haloalkoxy groups containing 1 to 4 carbon atoms which is identically or differently substituted with 1 to 9 halogen atoms), phenyl, heteroaryl, halogen, cyano, haloalkyl (a linear or branched alkyl group containing 1 to 4 carbon atoms which is substituted with 1 to 9 halogen atoms), or haloalkoxy (a linear or branched alkoxy group containing 1 to 4 carbon atoms which is identically or different substituted with 1 to 9 halogen atoms).

R$^3$ represents (1) a hydrogen atom, (2) a halogen atom, (3) alkyl containing 1 to 6 carbon atoms substituted with acyloxy represented by 1 to 4 (a linear or branched aliphatic hydrocarbon groups containing 1 to 8 carbon atoms)-CO—O— groups, 1 to 13 halogen atoms, or 1 to 4a hydroxyl groups, (4) unsubstituted alkyl containing 1 to 6 carbon atoms, (5) —OR, —SR, or —SO$_2$R (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), or (6) haloalkyl (a linear or branched alkyl group containing 1 to 4 carbon atoms which is identically or different substituted with 1 to 9 halogen atoms).

R$^4$ represents a hydrogen atom, a halogen atom, alkyl containing 1 to 6 carbon atoms, nitro, amino, phenyl, benzyl, or a thiophene ring, a pyridine ring, a pyrrole ring, an imidazole ring, a benzene ring, a naphthalene ring, a pyrimidine ring, a furan ring, a pyrazine ring, a pyrazole ring or an oxazole ring, which is formed together with a carbon atom on a pyrimidine ring as a result of binding with R$^3$.

Examples of the mono- or bi-cyclic ring which may contain 0 to 3 heteroatoms, represented by R$^1$, include phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolinyl, pyridyl, quinolyl, isoquinolyl, benzothiazolyl, benzoisothiazolyl, pyrrolyl, indolyl, isoindolyl, benzoxazolyl, benzisoxazolyl, thienyl, benzothienyl, imidazolyl, benzimidazolyl, pyrazolyl and pyridonyl groups. Of these, phenyl, oxazolyl, thiazolyl, pyridyl and thienyl groups are preferable, and phenyl, pyridyl and thiazolyl groups are more preferable. Moreover, examples of the substituent include —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), —SiR$^5$R$^6$R$^7$, —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), haloalkyl (a linear or branched alkyl group containing 1 to 4 carbon atoms which is identically or differently substituted with 1 to 9 halogen atoms), haloalkenyl (a linear or branched alkenyl group containing 2 to 6 carbon atoms which is identically or differently substituted with 1 to 4 halogen atoms), haloalkoxy (a linear or branched alkoxy group containing 1 to 4 carbon atoms which is identically or differently substituted with 1 to 9 halogen atoms), acylalkoxy (a linear or branched alkoxy group containing 1 to 3 carbon atoms which is substituted with 1 to 2 acyl groups represented by —CO— (a linear or branched aliphatic hydrocarbon group containing 1 to 8 carbon atoms)), acyloxyalkyl (a linear or branched alkyl group containing 1 to 3 carbon atoms which is substituted with 1 to 2 acyloxy groups represented by an (a linear or branched aliphatic hydrocarbon group containing 1 to 8 carbon atoms)-CO—O— group, alkylsulfonylalkyl (a linear or branched alkyl group containing 1 to 3 carbon atoms which is substituted with 1 to 2 linear or branched alkylsulfonyl groups containing 1 to 8 carbon atoms), siloxyalkyl (a linear or branched alkyl group containing 1 to 3 carbon atoms which is substituted with —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents)), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with 1 to 2 linear or branched alkoxy groups containing 1 to 8 carbon atoms), haloalkoxyalkyl (a linear or branched alkyl group containing 1 to 3 carbon atoms substituted with 1 to 2 linear or branched haloalkoxy groups containing 1 to 4 carbon atoms which is identically or differently substituted with 1 to 9 halogen atoms), alkylthioalkyl (a linear or branched alkyl group containing 1 to 3 carbon atoms which is substituted with 1 to 2 linear or branched alkylthio groups containing 1 to 8 carbon atoms), dialkoxyacetal (a dialkoxymethyl group in which two linear or branched alkoxy groups each containing 1 to 8 carbon atoms are substituted with methyl groups), alkoxyalkoxy (a linear or branched alkyl group containing 1 to 3 carbon atoms which is substituted with 1 to 2 linear or branched alkoxys group containing 1 to 8 carbon atoms), cyanoalkyl (a linear or branched alkyl group containing 1 to 3 carbon atoms which is substituted with a cyano group), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine. Preferred examples of the substituent include alkyl (e.g. a methyl group, an ethyl group, an n-propyl group, and an isopropyl group), alkoxy (e.g. a methoxy group, an ethoxy group, an n-propoxy group, and an isopropoxy group), acylalkoxy (e.g. an acetylmethoxy group, a propionylmethoxy group, and an acetylethoxy group), halogen (e.g. a fluorine atom, a chlorine atom, and a bromine atom), cyano, haloalkyl (e.g. a monofluoromethyl group, a difluoromethyl group, a trifluoromethyl group, and a heptafluoroisopropyl group), hydroxyalkyl (e.g. a hydroxymethyl group and a hydroxyethyl group), cyanoalkyl (e.g. a cyanomethyl group and a cyanoethyl group), alkoxyalkyl (e.g. a methoxymethoxy group, an ethoxymethoxy group, and a methoxyethoxy group), haloalkoxyalkyl (e.g. a monofluoromethoxymethyl group, a difluoromethoxymethyl group, and a trifluoromethoxymethyl group), haloalkoxy (e.g. a monofluoromethoxy group, a difluoromethoxy group, and a trifluoromethoxy group), a benzyloxy group, and a phenoxy group.

Examples of the linear or branched alkyl containing 1 to 6 carbon atoms, linear or branched alkenyl containing 2 to 8 carbon atoms, linear or branched alkynyl containing 2 to 8 carbon atoms, cycloalkyl containing 3 to 8 carbon atoms or cycloalkenyl containing 3 to 8 carbon atoms, represented by R', include an n-butyl group, an s-butyl group, a t-butyl group, an n-hexyl group, a 1-propenyl group, a 2-propenyl group, and an isopropenyl group. Of these, an n-butyl group, an s-butyl group, a t-butyl group, a 1-propenyl group, and an isopropenyl group are preferable. Examples of the substituent include —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), —SiR$^5$R$^6$R$^7$, —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), haloalkyl (a linear or branched alkyl group containing 1 to 4 carbon atoms which is identically or differently substituted with 1 to 9 halogen atoms), haloalkenyl (a linear or branched alkenyl group containing 2 to 6 carbon atoms which is identically or differently substituted with 1 to 4 halogen atoms), haloalkoxy (a linear or branched alkoxy group containing 1 to 4 carbon atoms which is identically or differently substituted with 1 to 9 halogen atoms), acylalkoxy (a linear or branched alkoxy group containing 1 to 3 carbon atoms which is substituted with 1 to 2 acyl groups represented by —CO— (a linear or branched aliphatic hydrocarbon group containing 1 to 8 carbon atoms)), acyloxyalkyl (a linear or branched alkyl group containing 1 to 3 carbon atoms which is substituted with 1 to 2 acyloxy groups represented by an (a linear or branched aliphatic hydrocarbon group containing 1 to 8 carbon atoms)-CO—O— group, alkylsulfonylalkyl (a linear or branched alkyl group containing 1 to 3 carbon atoms which is substituted with 1 to 2 linear or branched alkylsulfonyl groups containing 1 to 8 carbon atoms), siloxyalkyl (a linear or branched alkyl group containing 1 to 3 carbon atoms which is substituted with —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents)), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with 1 to 2 linear or branched alkoxy groups containing 1 to 8 carbon atoms), haloalkoxyalkyl (a linear or branched alkyl group containing 1 to 3 carbon atoms substituted with 1 to 2 linear or branched haloalkoxy groups containing 1 to 4 carbon atoms which is identically or differently substituted with 1 to 9 halogen atoms), alkylthioalkyl (a linear or branched alkyl group containing 1 to 3 carbon atoms which is substituted with 1 to 2 linear or branched alkylthio groups containing 1 to 8 carbon atoms), dialkoxyacetal (a dialkoxymethyl group in which two linear or branched alkoxy groups each containing 1 to 8 carbon atoms are substituted with methyl groups), alkoxyalkoxy (a linear or branched alkyl group containing 1 to 3 carbon atoms which is substituted with 1 to 2 linear or branched alkoxy groups containing 1 to 8 carbon atoms), cyanoalkyl (a linear or branched alkyl group containing 1 to 3 carbon atoms which is substituted with 1 to 2 cyano groups), halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine. Preferred examples of the substituent include alkoxycarbonyl (e.g. a methoxycarbonyl group and an ethoxycarbonyl group), halogen (e.g. a fluorine atom, a chlorine atom, and a bromine atom), cyano, hydroxyalkyl (e.g. a hydroxymethyl group and a hydroxyethyl group), alkoxyalkyl (e.g. a methoxymethyl group, an ethoxymethyl group, and a methoxyethyl group), haloalkyl (e.g. a monofluoromethyl group, a difluoromethyl group, a trifluoromethyl group, and a heptafluoroisopropyl group), haloalkoxy (e.g. a monofluoromethoxy group, a difluoromethoxy group, and a trifluoromethoxy group), haloalkoxyalkyl (e.g. a monofluoromethoxymethyl group, a difluoromethoxymethyl group, and a trifluoromethoxymethyl group), cyanoalkyl (e.g. a cyanomethyl group and a cyanoethyl group), a phenyl group, a pyridyl group, a furyl group, a thiazolyl group, and a pyrimidinyl group.

Examples of the —SiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), represented by R$^1$, include a trimethylsilyl group, a triethylsilyl group, a triisopropylsilyl group, a t-butyldimethylsilyl group, and a t-butyldiphenylsilyl group. Of these, a trimethylsilyl group and a triethylsilyl group are preferable.

R$^2$ preferably represents a hydrogen atom or a cyano group. As linear or branched alkyl containing 1 to 8 carbon atoms, a methyl group and an ethyl group are preferable. As linear or branched alkenyl containing 2 to 8 carbon atoms, an ethynyl group and a propenyl group are preferable.

Examples of R$^2$ include —C(O)OR, —C(O)NHR, —CONR$_2$ (wherein R represents linear or branched alkyl containing 1 to 6 carbon atoms, linear or branched alkenyl containing 2 to 8 carbon atoms, linear or branched alkynyl containing 2 to 8 carbon atoms, or cycloalkyl containing 3 to 8 carbon atoms), a phenyl group, and a heteroaryl group. Of these, a phenyl group is preferable.

Examples of the halogen atom represented by R$^2$ include a chlorine atom, an iodine atom, a bromine atom, and a fluorine atom. Of these, a chlorine atom and a fluorine atom are preferable.

Examples of the alkoxy group represented by R$^2$ include a methoxy group, an ethoxy group, an n-propoxy group, and an isopropoxy group. Of these, a methoxy group and an ethoxy group are preferable.

Preferred examples of the haloalkyl group represented by R$^2$ include a monofluoromethyl group, a difluoromethyl group, and a trifluoromethyl group. Preferred examples of the haloalkoxy group represented by R$^2$ include a monofluoromethoxy group, a difluoromethoxy group, and a trifluoromethoxy group.

Examples of the halogen atom represented by R$^3$ include a chlorine atom, an iodine atom, a bromine atom, and a fluorine atom. Of these, a chlorine atom, a bromine atom, and an iodine atom are preferable.

Examples of the alkyl group containing 1 to 6 carbon atoms substituted with 1 to 4 acyloxy groups represented by (a linear or branched aliphatic hydrocarbon group containing 1 to 8 carbon atoms)-CO—O— groups, 1 to 13 halogen atoms or 1 to 4 hydroxyl groups, represented by R$^3$, include a chloromethyl group, a 1-chloroethyl group, a 1-bromoethyl group, a 1-fluoroethyl group, an acetyloxymethyl group, a 1-acetyloxyethyl group, a 1-propionyloxyethyl group, and a 1-hydroxyethyl group. Of these, a 1-chloroethyl group, a 1-fluoroethyl group, a 1-acetyloxyethyl group, and a 1-hydroxyethyl group are preferable.

Preferred examples of the unsubstituted alkyl group containing 1 to 6 carbon atoms, represented by R$^3$, include a methyl group and an ethyl group.

Examples of R$^3$ include —OR, —SR, and —SO$_2$R (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms). Of these, a methoxy group, an ethoxy group, a methylthio group, and an ethylthio group are preferable.

Examples of the haloalkyl group represented by R$^3$ include a monofluoromethyl group, a difluoromethyl group, a trifluoromethyl group, a pentafluoroethyl group, a heptafluoropropyl group, and a heptafluoroisopropyl group. Of these, a monofluoromethyl group, a difluoromethyl group, and a trifluoromethyl group are preferable.

Examples of the halogen atom represented by R$^4$ include a chlorine atom, an iodine atom, a bromine atom, and a fluorine atom. Of these, a chlorine atom, a bromine atom, and an iodine atom are preferable.

Preferred examples of the linear or branched alkyl group containing 1 to 6 carbon atoms, represented by R$^4$, include a methyl group and an ethyl group.

An example of the thiophene ring represented by R$^4$, which is formed together with a carbon atom on a pyrimidine ring as a result of binding with R$^3$ is a ring represented by the following general formula (IV-1):

[Formula 2]

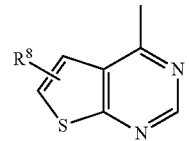

[IV-1]

(wherein R$^8$ represents a hydrogen atom, a methyl group, a fluorine atom, or a chlorine atom). A thieno[2,3-d]pyrimidine ring, wherein R$^8$ represents a hydrogen atom or a chlorine atom, is preferable.

An example of the benzene ring represented by R$^4$, which is formed together with a carbon atom on a pyrimidine ring as a result of binding with R$^3$, is a ring represented by the following general formula (IV-2):

[Formula 3]

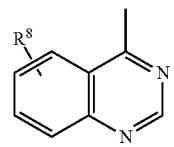

[IV-2]

(wherein $R^8$ represents a hydrogen atom, a methyl group, a fluorine atom, a chlorine atom, a bromine atom, an iodine atom, a methoxy group, a trifluoromethyl group, a cyano group, a nitro group, a methylthio group, a propargyl group, a propargyloxy group, a benzyl group, a benzyloxy group, a heteroaryl group, or a phenyl group). A quinazoline ring, wherein $R^8$ represents a hydrogen atom, a fluorine atom or a chlorine atom, is preferable.

The term "alkyl" is used in the invention of the present application to mean a linear or branched alkyl group containing 1 to 8 carbon atoms. Examples of such an alkyl group include a methyl group, an ethyl group, an n-propyl group, an isopropyl group, an n-butyl group, an isobutyl group, an s-butyl group, a t-butyl group, an n-pentyl group, an isopentyl group, a neopentyl group, an n-hexyl group, an n-heptyl group, and an n-octyl group.

The term "alkenyl" is used in the invention of the present application to mean a linear or branched alkenyl group containing 2 to 8 carbon atoms. Examples of such an alkenyl group include an ethenyl group, a 1-propenyl group, a 2-propenyl group, an isopropenyl group, a 1-butenyl group, a 2-butenyl group, and a 3-butenyl group.

The term "alkynyl" is used in the invention of the present application to mean a linear or branched alkynyl group containing 2 to 8 carbon atoms. Examples of such an alkynyl group include an ethynyl group, a 2-propynyl group, a 2-butynyl group, and a 3-butynyl group.

The term "cycloalkyl" is used in the invention of the present application to mean a cycloalkyl group containing 3 to 8 carbon atoms. Examples of such a cycloalkyl group include a cyclopropyl group, a cyclobutyl group, a cyclopentyl group, and a cyclohexyl group.

The term "cycloalkenyl" is used in the invention of the present application to mean a cycloalkenyl group containing 3 to 8 carbon atoms. Examples of such a cycloalkenyl group include a 1-cyclopentyl group, a 2-cyclopentyl group, a 3-cyclopentyl group, a 1-cyclohexyl group, a 2-cyclohexyl group, and a 3-cyclohexyl group.

The term "heteroatom" is used in the invention of the present application to include a nitrogen atom, an oxygen atom, and a sulfur atom.

The term "halogen" is used in the invention of the present application to include fluorine, chlorine, bromine, and iodine.

The term "halo . . . " (for example, "haloalkyl") is used in the invention of the present application to include fluorine, chlorine, bromine, and iodine.

The term "haloalkyl" is used in the invention of the present application to mean a linear or branched alkyl group containing 1 to 4 carbon atoms which is identically or differently substituted with 1 to 9 halogen atoms. Examples of such haloalkyl include a monofluoromethyl group, a monochloromethyl group, a monobromomethyl group, a difluoromethyl group, a trifluoromethyl group, a pentafluoroethyl group, an n-heptafluoropropyl group, and an isoheptafluoropropyl group.

The term "haloalkenyl" is used in the invention of the present application to mean a linear or branched alkenyl group containing 2 to 6 carbon atoms which is identically or differently substituted with 1 to 4 halogen atoms. Examples of such haloalkenyl include a 1,2-difluoroethenyl group, a 2,2-difluoroethenyl group, and a 3,3-difluoro-2-propenyl group.

The term "alkoxy" is used in the invention of the present application to mean an (alkyl)-O— group, the alkyl portion of which has the above described meanings. Examples of such alkoxy include a methoxy group, an ethoxy group, an n-propoxy group, an isopropoxy group, an n-butoxy group, an s-butoxy group, and a t-butoxy group.

The term "haloalkoxy" is used in the invention of the present application to mean a (haloalkyl)-O— group, the haloalkyl portion of which has the above described meanings. Examples of such haloalkoxy include a monofluoromethoxy group, a difluoromethoxy group, a trifluoromethoxy group, a 2,2-difluoroethoxy group, and a 2,2,2-trifluoroethoxy group.

All of the term "acyl," the term "acyl" in acylalkoxy, the term "acyl" in acyloxyalkyl, and the term "acyl" in acyloxy are used in the invention of the present application to mean a group represented by —CO— (a linear or branched aliphatic hydrocarbon group containing 1 to 8 carbon atoms). Examples of such a group include an acetyl group, a propionyl group, a butyryl group and an isobutyryl group. It is to be noted that the aliphatic hydrocarbon group means alkyl, alkenyl, alkynyl, cycloalkyl, cycloalkenyl, and cycloalkynyl in the present application.

The term "acylalkoxy" is used in the invention of the present application to mean a linear or branched alkoxy group containing 1 to 3 carbon atoms which is substituted with 1 to 2 above described acyl groups. Examples of such acylalkoxy include an acetylmethoxy group, an acetylethoxy group, and an acetylpropoxy group.

The term "acyloxy" is used in the invention of the present application to mean a (a linear or branched aliphatic hydrocarbon group containing 1 to 8 carbon atoms)-CO—O— group. Examples of such acyloxy include an acetoxy group, a propionyloxy group, an isopropionyloxy group, and a pivaloyloxy group.

The term "acyloxyalkyl" is used in the invention of the present application to mean a linear or branched alkyl group containing 1 to 3 carbon atoms which is substituted with 1 to 2 above described acyl groups. Examples of such acyloxyalkyl include an acetoxymethyl group, an acetoxyethyl group, and an acetoxypropyl group.

The term "alkylsulfonyl" is used in the invention of the present application to mean an (alkyl)-SO$_2$— group, the alkyl portion of which has the above described meanings. Examples of such alkylsulfonyl include a methylsulfonyl group, an ethylsulfonyl group, an n-propylsulfonyl group, and an isopropylsulfonyl group.

The term "alkylsulfonylalkyl" is used in the invention of the present application to mean a linear or branched alkyl group containing 1 to 3 carbon atoms which is substituted with 1 to 2 above described alkylsulfonyl groups. Examples of such alkylsulfonylalkyl include a methylsulfonylmethyl group, a methylsulfonylethyl group, and a methylsulfonylpropyl group.

The term "siloxy" is used in the invention of the present application to mean —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents). Examples of such siloxy include a trimethylsiloxy group, a triethylsiloxy group, a triisopropylsiloxy group, a t-butyldimethylsiloxy group, and a t-butyldiphenylsiloxy group.

The term "siloxyalkyl" is used in the invention of the present application to mean a linear or branched alkyl group containing 1 to 3 carbon atoms which is substituted with the above described siloxy group. Examples of such siloxyalkyl include a trimethylsiloxymethyl group, a trimethylsiloxyethyl group, a trimethylsiloxypropyl group, a triethylsiloxymethyl group, and a t-butyldimethylsiloxymethyl group.

The term "hydroxyalkyl" is used in the invention of the present application to mean a linear or branched alkyl group containing 1 to 3 carbon atoms which is substituted with 1 to 2 hydroxyl groups. Examples of such hydroxyalkyl include a hydroxymethyl group, a hydroxyethyl group, and a hydroxypropyl group.

The term "alkoxyalkyl" is used in the invention of the present application to mean a linear or branched alkyl group containing 1 to 3 carbon atoms which is substituted with 1 to 2 above described alkoxy groups. Examples of such alkoxyalkyl include a methoxymethyl group, an ethoxymethyl group, a propoxymethyl group, and an isopropoxymethyl group.

The term "alkylthio" is used in the invention of the present application to mean an (alkyl)-S— group, the alkyl portion of which has the above described meanings. Examples of such alkylthio include a methylthio group, an ethylthio group, and a propylthio group.

The term "alkylthioalkyl" is used in the invention of the present application to mean a linear or branched alkyl group containing 1 to 3 carbon atoms which is substituted with 1 to 2 above described alkylthio groups. Examples of such alkylthioalkyl include a methylthiomethyl group, an ethylthiomethyl group, a methylthioethyl group, and an ethylthioethyl group.

The term "dialkoxyacetal" is used in the invention of the present application to mean a dialkoxymethyl group in which the above described two alkoxy groups are substituted with methyl groups. Examples of such dialkoxyacetal include a dimethoxymethyl group, a diethoxymethyl group, and a dipropoxymethyl group.

The term "alkoxyalkoxy" is used in the invention of the present application to mean a linear or branched alkoxy group containing 1 to 3 carbon atoms which is substituted with 1 to 2 above described alkoxy groups. Examples of such alkoxyalkoxy include a methoxymethoxy group, a methoxyethoxy group, and a methoxypropoxy group.

The term "haloalkoxyalkyl" is used in the invention of the present application to mean a linear or branched alkyl group containing 1 to 3 carbon atoms which is substituted with 1 to 2 above described haloalkoxy groups. Examples of such haloalkoxyalkyl include a monofluoromethoxymethyl group, a difluoromethoxymethyl group, and a trifluoromethoxymethyl group.

The term "cyanoalkyl" is used in the invention of the present application to mean a linear or branched alkyl group containing 1 to 3 carbon atoms which is substituted with 1 to 2 cyano groups. Examples of such cyanoalkyl include a cyanomethyl group, a cyanoethyl group, and a cyanopropyl group.

In the invention of the present application, "phenyl," "thienyl," "pyridyl," "oxazolyl," "furanyl," "thiazolyl," "naphthyl," "pyrimidinyl," "benzothiazolyl," "benzoxazolyl," and "benzodioxolyl" may optionally have one or more substituents that are identical to or different from one another, or may not have such substituent(s).

The term "phenoxy" is used in the invention of the present application to include a phenoxy group having one or more substituents that may be identical to or different from one another, and an unsubstituted phenoxy group.

The term "benzyl" is used in the invention of the present application to include a benzyl group having one or more substituents that may be identical to or different from one another, and an unsubstituted benzyl group.

The term "benzyloxy" is used in the invention of the present application to include a benzyloxy group having one or more substituents that may be identical to or different from one another, and an unsubstituted benzyloxy group.

The term "propargyl" is used in the invention of the present application to include a propargyl group having a substituent at the alkyne terminus thereof, and an unsubstituted propargyl group.

The term "propargyloxy" is used in the invention of the present application to include a propargyloxy group having a substituent at the alkyne terminus thereof, and an unsubstituted propargyloxy group.

The term "heteroaryl" is used in the invention of the present application to include oxazolyl, isoxazolyl, thiazolyl, isothiazolyl, pyrimidinyl, pirazinyl, quinoxalyl, quinazolinyl, quinolyl, isoquinolyl, indolyl, isoindolyl, imidazolyl, pyrazolyl, pyridyl, furyl, thienyl, and pyrrolyl. There groups may optionally have one or more substituents that may be identical to or different from one another, or may not have such substituent(s).

The term "cyclic ether" is used in the invention of the present application to include epoxy, oxetane, tetrahydrofuran, tetrahydropyran, dioxolane, and dioxane.

The term "cyclic amine" is used in the invention of the present application to include pyrrolidinyl, imidazolidinyl, pyrazolidinyl, piperidinyl, piperazinyl, and morpholinyl.

The term "imide" is used in the invention of the present application to include chain imide and cyclic imide.

Since the compound represented by the general formula [I] of the present invention has an amino group, acid-added salts derived from such an amino group are also included in the present invention.

Examples of an acid that forms such acid-added salts include: inorganic acids such as hydrochloric acid, hydrobromic acid, nitric acid, sulfuric acid, and phosphoric acid; carboxylic acids such as formic acid, oxalic acid, fumaric acid, adipic acid, stearic acid, oleic acid, and aconitic acid; sulfonic acids such as methanesulfonic acid, benzenesulfonic acid, and p-toluenesulfonic acid; and saccharin.

Moreover, various optical isomers, racemic bodies, and mixtures thereof, which are derived from asymmetric carbon atoms that are generated when $R^2$ in the compound represented by the general formula [I] of the present invention is —R, —OR, —C(O)OR, —C(O)NHR, —CONR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), hydroxyalkyl (a linear or branched alkyl group containing 1 to 3 carbon atoms which is substituted with 1 to 2 hydroxyl groups), alkoxyalkyl (a linear or branched alkyl group containing 1 to 3 carbon atoms which is substituted with 1 to 2 linear or branched alkoxy groups containing 1 to 8 carbon atoms), phenyl, heteroaryl, halogen, cyano, haloalkyl (a linear or branched alkyl group containing 1 to 4 carbon atoms which is substituted with 1 to 9 halogen atoms), or haloalkoxy (a linear or branched alkoxy group containing 1 to 4 carbon atoms which is identically or different substituted with 1 to 9 halogen atoms), are all included in the present invention.

Furthermore, various optical isomers, racemic bodies, and mixtures thereof, which are derived from asymmetric carbon atoms that are generated when $R^3$ in the compound represented by the general formula [I] of the present invention is alkyl containing 1 to 6 carbon atoms substituted with acyloxy represented by —CO—O— (a linear or branched aliphatic hydrocarbon group containing 1 to 8 carbon atoms), a halogen atom, or a hydroxyl group, are all included in the present invention.

As shown in the following reaction process formula, the compound [I] of the present invention, which is represented by the following formula, can be produced, for example, by reacting a chloropyrimidine derivative represented by the following general formula [II] with a 3-butynylamine derivative represented by the following general formula [III] in the presence of a base and a solvent.

[Formula 4]

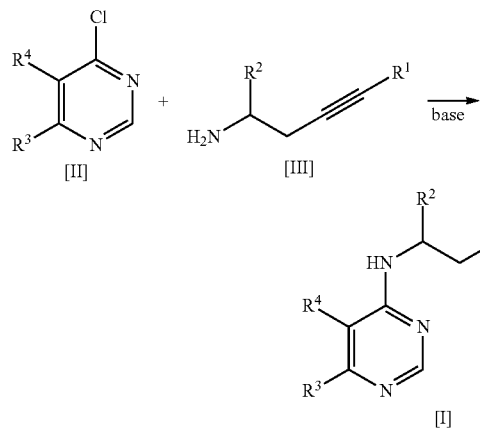

(wherein $R^1$, $R^2$, $R^3$ and $R^4$ have the same definitions as those described above).

The type of the solvent is not particularly limited, as long as it is not directly involved in the present reaction. Examples of such a solvent include: chlorinated or unchlorinated, aromatic, aliphatic or alicyclic hydrocarbons, such as benzene, toluene, xylene, methylnaphthalene, petroleum ether, ligroin, hexane, chlorobenzene, dichlorobenzene, chloroform, dichloroethane, and trichloroethylene; ethers such as tetrahydrofuran, dioxane, and diethyl ether; nitriles such as acetonitrile and propionitrile; ketones such as acetone and methyl ethyl ketone; amide compounds such as N,N-dimethylformamide, N,N-dimethylacetamide, and N-methyl pyrrolidone; sulfoxy compounds such as dimethyl sulfoxide; urea compounds such as N,N-dimethylimidazolidinone; sulfolane; and mixtures of the above described solvents. Of these, amide compounds such as N,N-dimethylformamide, N,N-dimethylacetamide and N-methylpyrrolidone are preferable.

The amount of the solvent can be determined, such that the amount of the compound [II] can be 5% to 80% by weight, and preferably 10% to 70% by weight.

The type of the base used herein is not particularly limited. Examples of the base include organic and inorganic bases, for example, organic bases such as tertiary amines (triethylamine, etc.) and DBU, and inorganic bases such as the hydrides, hydroxides, carbonates, hydrogencarbonates and the like of alkaline metals and alkaline-earth metals. Of these, organic bases such as tertiary amines (triethylamine, etc.) and DBU are preferable.

The base is used in an amount of 1.0 to 5.0 moles, and preferably of 1.2 to 2.0 moles, with respect to 1.0 mole of the compound [II].

The compound [III] is used as a raw material in an amount of 1.0 to 5.0 moles, and preferably of 1.0 to 1.2 moles, with respect to 1.0 mole of the compound [II].

The reaction temperature is not particularly limited. It is within a temperature range from a room temperature to the boiling point of a solvent used or lower. It is preferably from 60° C. to 110° C.

The reaction time changes depending on the above described concentration and temperature. It is generally from 0.5 to 8 hours.

After completion of the reaction, the compound [I] as produced above is subjected to ordinary post-treatments such as extraction, concentration and filtration, and it may be then purified, as appropriate, by known means such as recrystallization or various types of chromatography, as necessary.

When the thus produced compound [I] is a terminal alkyne ($R^1$=H; compound I-1), a Sonogashira reaction or the like may be utilized to introduce a substituent.

[Formula 5]

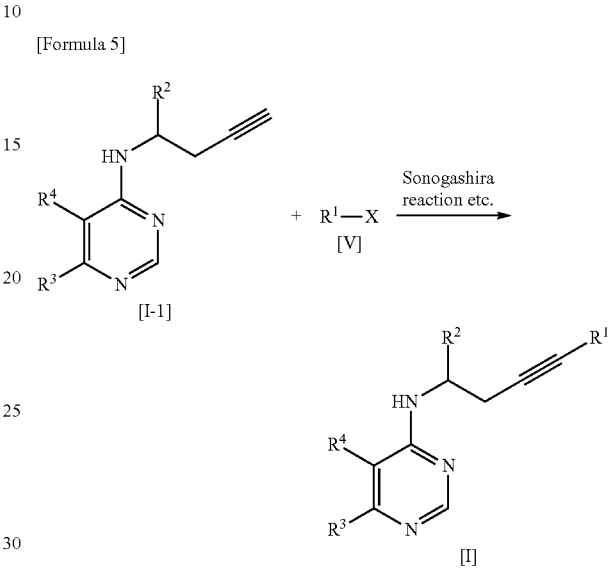

(wherein $R^1$ represents phenyl, heteroaryl or alkenyl, and $R^2$, $R^3$ and $R^4$ have the same definitions as those described above).

The compound [II] used in the present synthesis method can be produced, for example, by the method shown in the following formula, according to the method described in Non Patent Document 1.

[Formula 6]

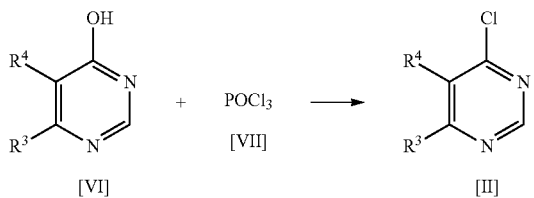

(wherein $R^3$ and $R^4$ have the same definitions as those described above).

Moreover, a commercially available product can be used as a 3-butynylamine derivative [III] in the present synthesis. If necessary, it can be produced by the method as described below. However, the following method is not intended to limit the scope of the present invention.

(Synthesis Method 1)

The Sonogashira reaction is carried out between an N-(3-butynyl)phthalimide derivative [VIII] and phenyl iodide or bromide, heteroaryl bromide or chloride, or alkenyl iodide or bromide [V]. Thereafter, a product [IX] is deprotected by hydrazine or a base, so as to produce a 3-butynylamine derivative [III].

[Formula 7]

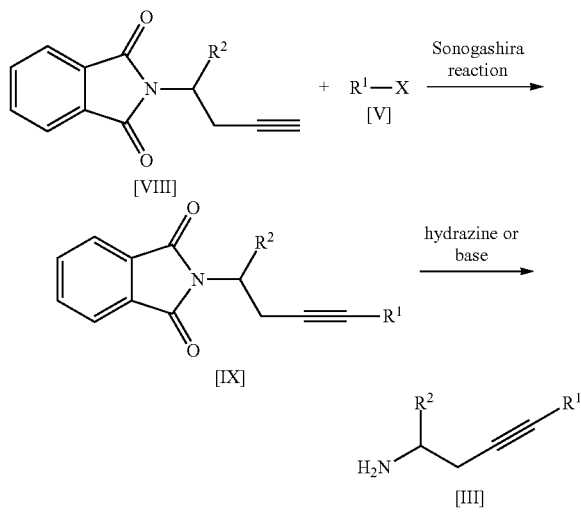

(wherein X represents iodine, bromine or chlorine, R¹ represents phenyl, heteroaryl or alkenyl, and R² has the same definitions as those described above).

(Synthesis Method 2)

Substituted butynyl alcohol [X] and phthalimide [XI] are subjected to a Mitsunobu reaction to synthesize a product [XII], and the thus synthesized product [XII] is then subjected to the Sonogashira reaction and then to deprotection in the same manner as in Synthesis method 1, so as to produce a 3-butynylamine derivative [III].

[Formula 8]

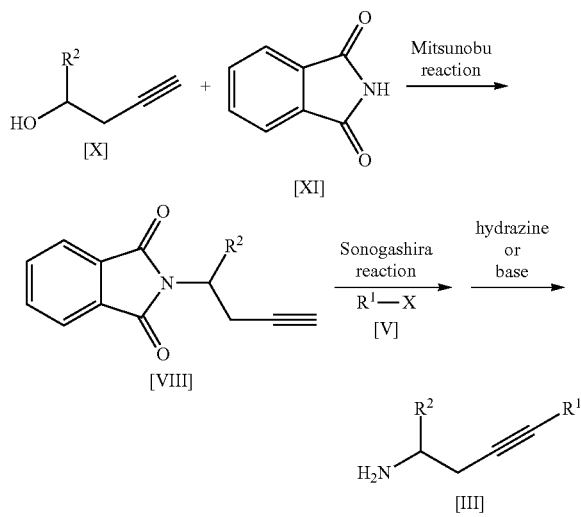

(wherein X represents iodine, bromine or chlorine, R¹ represents phenyl, heteroaryl or alkenyl, and R² has the same definitions as those described above).

(Synthesis Method 3)

Terminal alkyne [XII] is reacted with a Grignard reagent and is then reacted with ethylene oxide [XIII], so as to synthesize a 3-butynyl alcohol derivative [XIV]. Thereafter, this alcohol is subjected to the Mitsunobu reaction and then to deprotection, so as to produce a 3-butynylamine derivative [III].

[Formula 9]

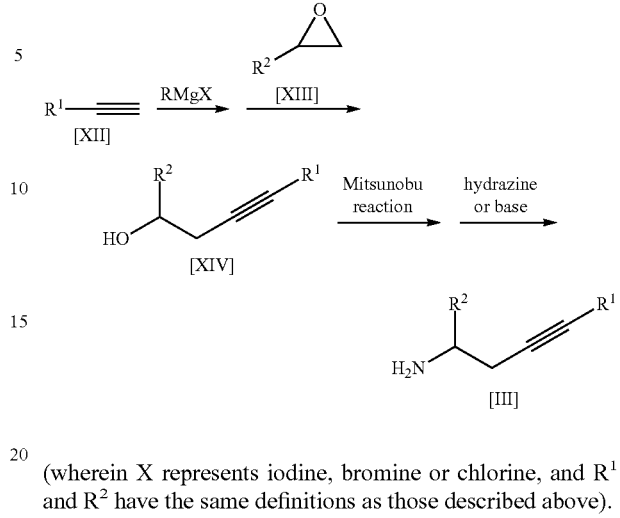

(wherein X represents iodine, bromine or chlorine, and R¹ and R² have the same definitions as those described above).

(Synthesis Method 4)

Substituted butynyl alcohol (X) is protected by a tosyl group, and thereafter, alkyl lithium is added so that terminal alkyne carbon is allowed to generate anion. A substituent is introduced into the terminal alkyne carbon by a nucleophilic substitution reaction, so as to produce a product [XVI]. Thereafter, the product [XVI] is reacted with potassium phthalimide [XVII] in the presence of potassium iodide, so as to produce a product [IX]. Thereafter, the product [IX] is deprotected, so as to produce a 3-butynylamine derivative [III].

[Formula 10]

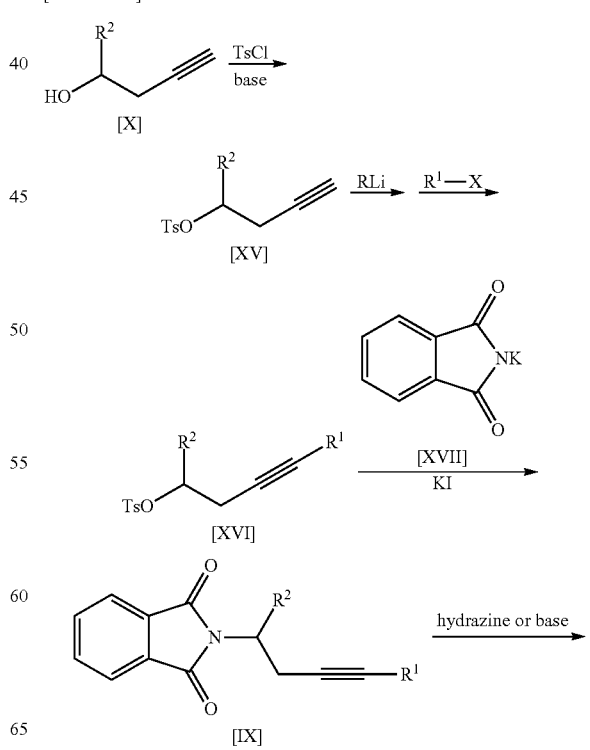

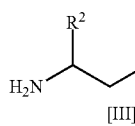

(wherein X represents iodine, bromine or chlorine, $R^1$ represents trialkylsilyl, and $R^2$ has the same definitions as those described above).

(Synthesis Method 5)

Sodium azide is reacted with a compound [XVIII] formed by protecting substituted butynyl alcohol [XIV] by a tosyl group, so as to produce an azide compound [XIV]. Thereafter, this azide compound [XIV] is reduced by lithium aluminum hydride, so as to produce a 3-butynylamine derivative [III].

[Formula 11]

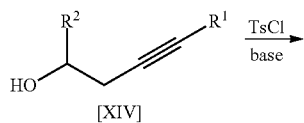

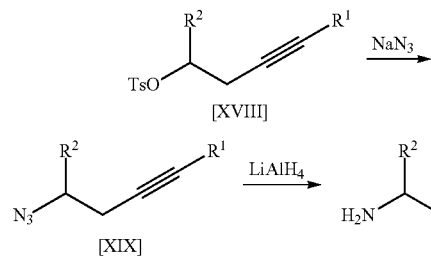

(wherein $R^1$ and $R^2$ have the same definitions as those described above).

(Synthesis Method 6)

A 3-butynylamine derivative [III] can be produced from 4-pentylamide [XX] by a Hofmann rearrangement.

[Formula 12]

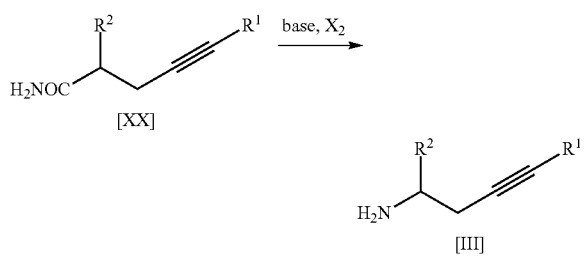

(wherein $R^1$ and $R^2$ have the same definitions as those described above).

(Synthesis Method 7)

A 3-butynylamine derivative [III] can be produced from acyl azide [XXI] by a Curtius rearrangement.

[Formula 13]

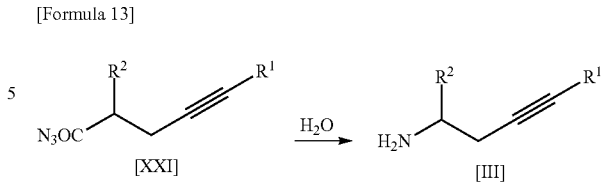

(wherein $R^1$ and $R^2$ have the same definitions as those described above).

[Control Effect]

The term "pest" is used in the invention of the present application to include all pests that affect agricultural and horticultural plants, and all pathogens that affect agricultural and horticultural plants.

Examples of agricultural and horticultural pests, on which the compound (I) of the present invention exhibits a control effect, will be given below.

Examples of such agricultural and horticultural pests include: pests belonging to Lepidoptera, such as *Plutella xylostella, Agrotis ipsilon, Agrotis segetum, Helicoverpa armigera, Helicoverpa assulta, Helicoverpa zea, Heliothis virescens, Mamestra brassicae, Naranga aenescens, Plusia nigrisigna, Pseudaletia separata, Spodoptera exigua, Spodoptera litura, Spodoptera littoralis, Spodoptera frugiperda, Spodoptera eridania, Manduca sexta, Endopiza viteana, Lyonetia prunifoliella malinella, Phyllonorycter ringoneella, Phyllocnistis citrella, Pectinophora gossypiella, Carposina niponensis, Adoxophyes orana faciata, Adoxophyes honmai, Homona magnamina, Cydla pomonella, Grapholita molesta, Chilosuppressalis, Cnaphalocrocis medinalis, Hellula undalis, Ostrinia nubilalis, Pseudoplusia includens, Trichoplusia ni, Hyphantria cunea, Pieris rapaecrucivora*, and *Parnara guttata*; pests belonging to Coleoptera, such as *Anomala cuprea, Anomala rufocuprea, Popillia japonica, Lepinotarsa decemlineata, Epilachna varivestis, Melanotus tamsuyensis, Lasioderma serricorne, Epuraea domina, Henosepilachna vigintioctopunctata, Tenebrio molitor, Tribolium castaneum, Anoplophora malasiaca, Monochamus alternatus, Callosobruchus chinensis, Aulacophora femoralis, Oulema oryzae, Phyllotreta striolata, Cylasformicarius, Anthonomus grandis, Ethinocnemus squameus, Hypera postica, Lissorhoptrus oryzophilus, Sitophilus zeamais, Sphenophrus venatus vestius, Sitophilus granarius, Diabrotica undecimpunctata, Diabrotica virgifera, Diabrotica barberi*, and *Paederus fuscipes*; pests belonging to Hemiptera, such as *Eurydema rugosa, Eysarcoris ventralis, Halyomorpha mista, Nezara viridula, Leptocorisa chinensis, Riptortus clavatus, Togo hemipterus, Stephanitis pyrioides, Epiacanthus stramineus, Empoasca onukii, Empoasca fabae, Nephotettix cinctinceps, Laodelphax striatellus, Nilaparvata lugens, Sogatella furcifera, Trioza erytreae, Psylla pyrisuga, Bemisia tabaci, Bemisia argentifolii, Dialeuro descitri, Trialeurodes vaporariorum, Aphis gossypii, Aphis pomi, Myzus persicae, Drosicha corpulenta, Icerya purchasi, Planococcus citri, Pseudococcus comstocki, Ceroplastes rubens, Unaspis yanonensis*, and *Cimex lectularius*; pests belonging to Thysanoptera, such as *Frankliniella occidentalis, Frankliniella intonsa, Scirtothrips dorsalis, Thrips palmi*, and *Thrips tabaci*; pests belonging to Diptera, such as *Dacus dorsalis, Dacus cucurbitae, Ceratitis capitata, Hydrellia griseola, Liriomyza bryoniae, Liriomyza trifolii, Hylemya platura, Rhagoletis pomonella, Mayetiola destructor, Musca domestica, Stomoxys calcitrans, Melophagus ovinus, Hypoderma lineatum, Hypoderma bovis, Oestrus ovis,*

*Glossina palpalis, Glossina morsitans, Prosimulium yezoensis, Tabanus trigonus, Telmatoscopus albipunctatus, Leptoconops nipponensis, Culex pipiens pallens, Aedes albopictus, Aedes aegypti,* and *Anopheles hyracanus sinesis*; pests belonging to Hymenoptera, such as *Apethymus kuri, Athalia rosae japonensis, Neodiprion sertifer, Eciton burchelli, Eciton schmitti, Camponotus japonicus, Vespa mandarina, Myrmecia* spp., *Solenopsis* spp., and *Monomorium pharaonic*; pests belonging to Dictyoptera, such as *Periplaneta fuliginosa, Periplaneta japonica,* and *Blattella germanica*; pests belonging to Orthoptera, such as *Teleogryllus emma, Gryllotalpa africana, Locusta migratoria, Oxya yezoensis,* and *Schistocerca gregaria*; pests belonging to Isoptera, such as *Coptotermes formosanus, Reticulitermes speratus,* and *Odontotermes formosanus*; pests belonging to Isoptera, such as *Ctenocephalidae felis, Pulex irritans,* and *Xenopsylla cheopis*; pests belonging to Mallophaga, such as *Menacanthus stramineus* and *Bovicola bovis*; pests belonging to Anoplura, such as *Haematopinus eurysternus, Haematopinus suis, Linognathus vituli,* and *Solenopotes capillatus*; Tetranychidae such as *Panonychus citri, Panonychus ulmi, Tetranychus kanzawai,* and *Tetranychus urticae*; Eriophyidae such as *Acaphylla theae, Aculops pelekassi, Eriophyes chibaensis,* and *Aceria tulipae*; Tarsonemidae such as *Polyphaotarsonemus latus* and *Steneotarsonemus pallidus*; Acaridae such as *Tyrophagus putrescentiae* and *Rhizoglyphus robini; Varroa* such as *Varroa jacobsoni*; Ixodidae such as *Boophilus microplus* and *Haemaphysalis longicornis*; Psoroptidae such as *Psoroptes ovis*; Sarcoptidae such as *Sarcoptes scabiei*; Crustacea such as *Armadillidium vulgare*; Nematoda such as *Prathylenchus penetrans, Prathylenchus vulnus, Globodera rostochiensis, Heterodera glycines, Meloidogyne hapla, Meloidogyne incognita,* and *Bursaphelenchus lignicolus*; and Mollusca such as *Ponacea canaliculata, Incilaria bilineata, Acusta despecta sieboldiana,* and *Euhadra peliomphala.*

Examples of agricultural and horticultural pathogens include *Pyricularia oryzae, Cochliobolus miyabeanus, Rhizoctonia solani, Gibberella fujikuroi, Erysiphe graminis* f.sp. *tritici, Erysiphe graminis* f.sp. *hordei, Pseudocercosporella herpotrichoides, puccinia graminis, Colletotrichum graminicola, Septoria tritici, Phynchosporium secalis* f.sp. *hordei, Phytophthora infestans, Alternari solani, Colletotrichum atramentarium, Thanatephorus cucumeris, Botrytis cinerea, Erisiphe pisi, Cercospora canescens, Sclerotinia sclerotiorum, Colletotrichum phaseolorum, Colletotrichum lindemuthiamum, Colletotrichum truncatum, Cercospora kikuchii, Phakopsora pachyrhizi, Gloeosporium conjac, Septoria perillae, Colletotrichum theae-sinensis, Cercospora beticola, Colletotrichum spinaciae, Peronospora effusa, Alternaria brassicae, Alternaria brassicicola, Colletotrichum higginsianum, Alternaria cucumerina, Pseudoperonospora cubensis, Sphaerotheca fuliginea, Phytophthora melonis, Corynespora cassiicola, Colletotrichum lagenarium, Fusarium oxysporum* f.sp. *cucumerinum, Phythium cucurbitacearum, Rhyzoctonia solani, Phomopsis* sp., *Phytophthora cryptogea, Colletotrichum orbiculare, Fusarium oxysporum* f.sp. *melonis, Fusarium oxysporum, Puccinia cnici-oleracei, Gloeosporium chrysanthemi, Gloeosporium carthami, Erysiphe heraclei, Sclerotinia intermedia, Alternaria dauci, Alternaria radicina, Oidiopsis sicula, Phytophthora capsici, Colletotrichum gloeosporioides, Fusarium oxysporum* f.sp. *lycopersici, Fulvia fulva, Alternaria solani, Verticillium dahliae, Sphaerotheca humuli, Phytophthora nicotianae, Phytophthora nicotianae* var. *parasitica, Pythium ultimum* var. *ultimum, Alternaria alternata, Mycosphaerella fragariae, Colletotrichum acutatum, Glomerella cingulata, Cercospora asparagi, Phomopsis asparagi, Puccinia asparagi-lucidi, Cladosporium allii-cepae, Fusarium oxysporum* f.sp. *cerae, Septoria alliacea, Alternaria porri, Puccinia allii, Botrytis squamosa, Phytophthora parri, Colletotrichum circinans, Alternaria* sp., *Botrytis allii, Pleospora herbarum, Peronospora destructor, Botrytis byssoidea, Mycosphaerella allicina, Septria alliacea, Sclerotinia allii, Phythoththora parri, Phyllactinia kakikola, Colletotrichum* ssp., *Glomerella* sp., *Cercospora kakivora, Cercosporakaki, Macrophoma kaki, Fusicladium levieri, Phomopsis kakivora, Pseudocercospora fuliginosa, Physalospora kaki, Aureobasidium pullulans, Capnophaeum fuliginodes, Cladosporium herbarum, Microxyphium* sp., *Scorias communis, Tripospermum juglandis, Zygophiala jamaicensis, Gloeosporium kaki, Pestalotia diospyri, Mycosphaerella nawae, Podosphaera tridactyla, Sphaerotheca pannosa, Botryosphaeria dothidea, Cladosporium carpophilum, Leucotelium pruni-persicae, Rosellinia necatrix, Fusarium lateritium,* Japanese apricot *Pseudocercospora circumscissa, Sphaceloma pruni-domesticae, Monilinia fructicola, Monilinia laxa, Glomerella mume, Rhizopus nigricans, Phyllactinia mali, Phytophthora cactorum, phytophthora syringae, Venturia pirina, Gymnosporangium asiaticum, Phyllactinia pyri, Venturia nashicola, Alternaria kikuchiana, Leptothyrium pomi, Monilinia fructigena, Physalospora piricola, Gibberella zeae, Stenella* sp., *Phyllosticta persicae, Gloeosporium laeticolor, Phomopsis* sp., *Gymnosporangium yamadae, Podosphaera leucotricha, phytophthora cambivola, Diplocarpon mali, Cristulariella moricola, Venturia inaequalis, Uncinula necator, Pseudocercospora vitis, Briosia ampelophaga, Elsinoe ampelina, Phyllosticta ampelicida, Phomopsis viticola, Plasmopara viticola, Capnodium salicinum, Morenoella quercina, Microsphaera alphitoides, Monochaetia monochaeta, Phytophthora citrophthora, Diaporthe citri, Mycosphaerella citri, Mycosphaerella horii, Elsinoe fawcettii* and *Mycosphaerella pinodes.*

[Pest Control Agents]

The pest control agent for agricultural and horticultural use of the present invention particularly has significant fungicidal effect and insecticidal effect. The present pest control agent comprises one or two or more of the compound(s) represented by the general formula [I] as active ingredient(s).

The compound represented by the general formula [I] of the present invention can be applied by treating plants via spraying, dispersion or coating of the active ingredient thereof, or by treating plant seeds, soil surrounding the plants or soil on which seeds are disseminated, paddy field, and water from water culture, with the active ingredient thereof. When the compound of the present invention is used as a fungicide, it can be applied before or after infection of plants with pathogens. When the compound of the present invention is used as an insecticide, it can be applied before pests and the like are generated, or after such pests are generated.

The present compound can be used as an agent that is suitable as a pest control agent for agricultural and horticultural use, such as a granule, a dust-granule mixture, a water-soluble powder, an oil solution, an emulsion, a microemulsion, a suspoemulsion, a liquid formulation, a wettable powder, an emulsifiable concentrate, a suspension concentrate, a tablet, a water-dispersible granule, a microcapsule, an aerosol, a paste, a jumbo agent, a dustable powder, a smoking agent and a fumigant, which are common formulation forms. Agents having the above described forms can be obtained by an ordinary method comprising mixing at least one of the compound of the present invention with a suitable solid or liquid carrier, and as desired, also with suitable auxiliary agents (for example, a surfactant, a solvent, and a stabilizer) for the improvement of the dispersibility of the active ingredient and other properties.

Examples of solid carriers and diluents include vegetable substances (e.g. crystalline cellulose, starch, wood flour, cork, waste from coffee processing, etc.), fibrous substances, artificial plastic powders, clay (e.g. kaoline, bentonite, white clay, diatomaceous earth, synthetic hydrous silicon oxide, Fubasami Clay, acid clay, etc.), talc and inorganic materials (e.g. vermiculite, montmorillonite, pumice, sulfur dust, apatite, mica, sericite, quartz powder, activated carbon, calcium carbonate, etc.), polymer compounds (polyvinyl chloride, petroleum resin, etc.), and chemical fertilizers (e.g. ammonium sulfate, ammonium phosphate, ammonium nitrate, ammonium chloride, calcium chloride, urea, etc.). Examples of liquid carriers and diluents include water, alcohols (e.g. methanol, ethanol, isopropanol, cyclohexanol, etc.), ketones (e.g. acetone, methyl ethyl ketone, cyclohexanone, etc.), ethers (e.g. ethyl cellosolve, butyl cellosolve, dioxane, etc.), aromatic hydrocarbons (e.g. benzene, toluene, xylene, ethyl benzene, methyl naphthalene, etc.), aliphatic hydrocarbons (e.g. kerosine, paraffin, etc.), esters (e.g. isopropyl acetate, benzyl acetate, etc.), nitriles, amides (e.g. N,N-dimethylformamide, dimethyl sulfoxide, etc.), and halogenated hydrocarbons (e.g. chlorobenzene, trichloroethylene, etc.).

Examples of a gaseous carrier, namely, a propellant, include carbon dioxide, butane gas, and fluorocarbon.

Examples of a surfactant include various anionic surfactants and nonionic surfactants, which have conventionally been used in the field of agricultural chemicals. Examples of such an anionic surfactant include: sulfonate surfactants and salts thereof, such as alkyl sulfonate, α-olefin sulfonate, lignin sulfonate, alkylbenzene sulfonate, alkylnaphthalene sulfonate, a naphthalene sulfonate formalin condensate, and dialkyl sulfosuccinate; sulfate surfactants and salts thereof, such as polyoxyethylene alkyl ether sulfate, polyoxyethylene alkyl allyl ether sulfate, polyoxyethylene styryl phenyl ether sulfate, polyoxyethylene phenyl alkyl allyl ether sulfate, polyoxyalkylene glycol sulfate, higher alcohol sulfate, fatty acid ester sulfate, and phenyl phenol (EO) sulfate; phosphate surfactants and salts thereof, such as polyoxyethylene alkyl ether phosphate, polyoxyethylenealkyl allyl phosphate, phenyl phenol (EO) phosphate, polyoxyethylene phenyl alkyl allyl ether phosphate, higher alcohol phosphate, and polyoxyethylene tribenzyl phenol phosphate; higher fatty acid salts; and polycarboxylate surfactants and salts thereof. Examples of the salts of the above described surfactants include the salts of sodium, potassium, magnesium, calcium, ammonium, ethanolamine, diethanolamine, triethanolamine, and various amines. Examples of such a nonionic surfactant include polyoxyethylene alkyl allyl ether, polyoxyethylene styryl phenyl ether, polyoxyethylene alkyl ether, polyoxyethylene phenyl alkyl allyl ether, polyoxyethylene sorbitan fatty acid ester, polyoxyethylene glycol, polyoxyethylene alkyl ester, a polyoxyethylene polyoxypropylene block copolymer, polyoxyalkylene glycol, alkyne diol (acetylene glycol), alkynylene polyoxyethylene diol, sorbitan fatty acid ester, and an alkylaryl ether formalin condensate.

Examples of a stabilizer include an isopropyl phosphate mixture, tricresyl phosphate, tall oil, epoxy oil, surfactants, fatty acids, and esters thereof. In addition to the aforementioned ingredients, the compound of the present invention can be processed into a pharmaceutical agent by mixing it with another fungicide, insecticide, herbicide, or fertilizer.

In general, the aforementioned pharmaceutical agent comprises 1% to 95% by weight of, and preferably 1% to 50% by weight of at least one of the compound [I] of the present invention. Such a pharmaceutical agent can be used singly or by being diluted. Approximately 1 g to 5 kg/hectare, and preferably approximately 2 g to 100 g/hectare of the compound [I] of the present invention can be used in a concentration of generally approximately 1 to 50000 ppm, and preferably approximately 50 to 1000 ppm.

The compound represented by general formula [I] of the present invention can be used singly or in the form of a pharmaceutical agent comprising the same. Alternatively, a pharmaceutical agent, which consists of a mixture of the present compound with a microbicide, a fungicide, an antibacterial agent, an acaricide, a nematicide, an insecticide, a biotic pesticide, a herbicide, a plant hormone agent, a plant growth modulator, a synergist, an attractant, a repellent, a pigment, a fertilizer and the like, or a mixture formed by combining one or two or more selected from such active ingredients, can be used as a pest control agent. It can be anticipated that, using such a pest control agent, expansion of action, diseases and pests as control targets and application period, and reduction in the drug amount, and an increase in multiplier effect can be achieved, or that the development of resistance can be prevented. In many cases, the activity of a mixture is higher than the activity of a single agent, and thus, cooperative effects of combined ingredients can be achieved.

Examples of combined ingredients in a mixture include the following compounds and the like.

Examples of the fungicide include azaconazole, bitertanol, bromuconazole, cyproconazole, difenoconazole, epoxiconazole, fenbuconazole, furconazole, hexaconazole, imibenconazole, metoconazole, myclobutanil, penconazole, propiconazole, simeconazole, tebuconazole, triadimefon, triadimenol, triticonazole, imazalil, triflumizole, pefurazoate, prochloraz, fenarimol, fenhexamid, fenpropimorph, piperalin, spiroxamine, iprodione, myclozolin, procymidone, vinclozolin, quinoxyfen, fludioxonil, chlorothalonil, dithianon, captan, folpet, iminoctadine-albesilate, iminoctadine-triacetate, ferbam, nabam, maneb, mancozeb, metiram, propineb, polycarbamate, thiram, ziram, zineb, Cupric oxide, Copper hydroxide, Copper oxychloride, Copper sulfate (anhydride), copper sulfate, Sulfur, benomyl, carbendazim, diethofencarb, zoxamide, pencycuron, fluopicolide, furametpyr, penthiopyrad, thifluzamide, boscalid, oxycarboxin, carboxin, fluopyram, flutolanil, mepronil, azoxystrobin, picoxystrobin, kresoximmethyl, trifloxystrobin, orysastrobin, metominostrobin, pyraclostrobin, famoxadone, fenamidone, pyribencarb, diflumetorim, cyazofamid, amisulbrom, meptyl dinocap, fluazinam, ferimzone, iprobenfos, isoprothiolane, quintozene, propamocarb, prothicarb, dimethomorph, iprovalicarb, benthiavalicarb, mandipropamid, pyroquion, tricyclazole, carpropamid, diclocymet, fenoxanil, balidamycin, polyoxin B, acibenzolar-S-methyl, probenazole, isotianil, laminarin, cymoxanil, fosetyl-Al, triazoxide, methasulfocarb, flusulfamide, ethaboxam, cyflufenamid, metrafenone, cyprodinil, mepanipyrim, pyrimethanil, blastcidin-S, streptomycin, kasugamycin, metalaxyl, metalaxyl-M, oxadixyl, bupirimate, hymexazol, and oxolinic acid.

Examples of the insecticide, acaricide and nematicide include aldicarb, benfuracarb, carbaryl, carbofuran, carbosulfan, fenobcarb, methiocarb, methomyl, oxamyl, thiodicarb, azephate, chlorpyrifos, diazinon, dimethoate, malathion, methamidophos, monocrotophos, parathion-methyl, profenofos, terbufos, endosulfan, ethiprole, fipronil, bifenthrin, cypermethrin, esfenvalerate, ethofenprox, lambda-cyhalothrin, tefluthrin, DDT, methoxychlor, acetamiprid, clothianidin, dinotefuran, imidacloprid, nitenpyram, thiacloprid, thiamethoxam, Spinosyn, spinetoram, abamectin, emamectin-benzoate, milbemectin, kinoprene, methoprene, fenoxycarb, pyriproxyfen, Methyl bromide, chloropicrin, pymetrozine, flonicamid, clofentezine, hexythiazox, etoxazole, diafenthiuron, azocyclotin, cyhexatin, fenbutatin oxide, propargite, tetradifon, chlorfenapyr, bensultap, cartap, thiocyclam, chlorfluazuron, diflubenzuron, flufenoxuron, hexaflumuron, lufenuron, novaluron, teflubenzuron, triflumuron, buprofezin, cyromazine, chromafenozide, halofenozide, methoxyfenozide, tebufenozide, amitraz, hydramethylnon, acequinocyl, fenazaquin, fenpyroximate, pyrimidifen, pyridaben, tebufenpyrad, tolfenpyrad, rotenone, indoxacarb, metaflumizone, spirodiclofen, spiromesifen, spirotetramat, Aluminium phosphide, chlorantraniliprole, flubendiamide, azadirachtin, benzoximate, bifenazate, chinomethionat, dicofol, and pyridalyl.

Examples of the herbicide include bensulfuron-methyl, azimsulfuron, cinosulfuron, cyclosulfamuron, pyrazosulfuron-ethyl, imazosulfuron, indanofan, cyhalofop-butyl, thenylchlor, esprocarb, etobenzanid, cafenstrole, clomeprop, dimethametryn, daimuron, bifenox, pyributicarb, pyriminobac-methyl, pretilachlor, bromobutide, benzofenap, benthiocarb, bentoxazone, benfuresate, mefenacet, fenoxaprop-P-ethyl, phenmedipham, diclofop-methyl, desmedipham, ethofumesate, isoproturon, amidosulfuron, anilofos, benfuresate, ethoxysulfuron, iodosulfuron, isoxadifen, foramsulfuron, pyraclonil, mesosulfuron, diuron, neburon, dinoterb, carbetamide, bromoxynil, oxadiazon, dimefuron, diflufenican, aclonifen, benzofenap, oxaziclomefone, isoxaflutole, oxadiargyl, flurtamone, metribuzin, methabenzthiazuron, tribufos, metamitron, ethiozin, flufenacet, sulcotrion, fentrazamide, propoxycarbazone, flucarbazone, metosulam, amicarbazone, glyphosate-isopropyl amine, glyphosate-trimesium, glufosinate-ammonium, bialaphos, butamifos, prosulfocarb, asulam, linuron, calcium peroxide, alachlor, pendimethalin, acifluofen-sodium, lactofen, ioxynil, alloxydim, sethoxydim, napropamide, pyrazolate, pyraflufen-ethyl, imazapyr, sulfentrazone, oxadiazon, paraquat, diquat, simazine, atrazine, fluthiacet-methyl, quizalofop-ethyl, bentazone, triaziflam, thidiazuron, mefenpyr, ethephon, and cyclanilide.

Examples of the biotic pesticide include Nuclear polyhedrosis virus (NPV), Granulosis virus (GV), Cytoplasmic polyhedrosis virus (CPV), *Steinernema carpocapsae, Steinernema glaseri, Monacrosporium phymatophagum, Steinernema kushidai, Pasteuria penetrans, Agrobacterium radiobacter, Bacillus subtilis, Erwinia carotovora, Pseudomonas fluorescens, Talaromyces flavus, Trichoderma atroviride, Bacillus thuringiensis, Beauveria brongniartii, Beauveria bassiana, Paecilomyces fumosoroseus, Verticillium lecanii, Xanthomonas campestris, Encarsia formosa, Eretmocerus eremicus, Eretmocerus mundus, Aphidius colemani, Aphidoletes aphidimyza, Diglyphus isaea, Dacnusa sibirica, Phytoseiulus persimilis, Amblyseius cucumeris, Amblyseius californicus*, and *Orius strigicollis*.

Examples of the pheromone agent include Codlelure ((E, E)-8,10-Dodecadien-1-ol), Beetarmylure-B ((Z)-9-Tetradecen-1-ol), tetradodecenyl acetate ((Z)-11-Tetradecenyl acetate), Pirimalure (14-Methyl-1-octadecene), and Peachflure ((Z)-13-Eicosen-10-one).

Examples of the natural fungicide and natural insecticide include Machine oils, Methylphenyl acetate, α-Pinene, Protein hydrolysate, (Z)-1-Tetradecen-1-ol, and Turpentine.

EXAMPLES

Hereinafter, the present invention will be specifically described in the following examples. These examples are not intended to limit the scope of the present invention.

Example 1

Production Example (1) In the general formula (I), $R^1$=TMS (trimethylsilyl), $R^2$=H, and $R^3$-$R^4$=thiophene (Synthesis of compound No. 2 in Table 1)

Stage A

3-Butynyl p-toluenesulfonate 10.00 g of 3-butyn-1-ol and 40 ml of triethylamine were added to 500 ml of dichloromethane, and the mixed solution was then cooled to 0° C. Then, 30.00 g of paratoluene sulfonyl chloride was slowly added to the solution, and the obtained mixture was then stirred at a room temperature overnight. Thereafter, water was added to the reaction solution, and it was then extracted with 200 ml of dichloromethane twice. The organic layer was washed with 200 ml of water twice, and it was then dried over magnesium sulfate. The magnesium sulfate was filtrated, and the organic layer was then concentrated. The residue was purified by column chromatography (Wako Gel C-200; hexane:ethyl acetate=6:1), so as to obtain 13.52 g of an O-tosyl compound.

Stage B

4-Trimethylsilanyl-3-butynyl p-toluenesulfonate 130 ml of dry tetrahydrofuran and 6.45 g of the O-tosyl compound obtained in the above described stage were added to a nitrogen-substituted flask, and the obtained mixture was then cooled to −78° C. After completion of the cooling, 18.9 ml of a 1.6 M n-butyllithium hexane solution was slowly added dropwise to this solution. After completion of the dropwise addition, the obtained solution was stirred at −78° C. for 2 hours, and 5.5 ml of trimethylsilyl chloride was then slowly added dropwise to the reaction solution. After completion of the dropwise addition, the obtained solution was stirred at −78° C. for 15 minutes, and it was further stirred at a room temperature for 1 hour. After completion of the stirring, 150 ml of water was added to the reaction solution, it was then extracted with 150 ml of dichloromethane twice, and it was then dried over magnesium sulfate. The organic layer was concentrated, and the residue was then dried in a vacuum, so as to obtain 8.37 g of a trimethylsilyl compound.

Stage C 2-(4-Trimethylsilanyl-3-butynyl)isoindol-1,3-dione 8.37 g of the trimethylsilyl compound obtained in the above described stage, 7.85 g of potassium phthalimide, and 0.46 g of potassium iodide were added to 64 ml of N,N-dimethylformamide, and the obtained mixture was then stirred at 140° C. for 2 hours. Thereafter, the reaction solution was cooled to a room temperature, and 100 ml of water was then added to the reaction solution, followed by extraction with 100 ml of ethyl acetate twice. The organic layer was washed with 100 ml of water twice and then with 100 ml of a saturated brine once, and it was dried over magnesium sulfate. The magnesium sulfate was filtrated, and the organic layer was then concentrated. Thereafter, the residue was purified by column chromatography (Wako Gel C-200; toluene:ethyl acetate=4:1), so as to obtain 3.28 g of a phthalimide compound.

Stage D

4-Trimethylsilanyl-3-butynylamine 121 ml of methanol and 2.25 g of hydrazine monohydrate (80%) were added to 3.28 g of the phthalimide compound obtained in the above described stage, and the obtained mixture was then stirred overnight. Thereafter, the reaction solution was concentrated, and the residue was then suspended in 50 ml of chloroform. Insoluble residue were filtrated, and the filtrated was then concentrated. The concentrate was dried under a reduced pressure, so as to obtain 1.72 g of amine.

Stage E

4-(4-Trimethylsilanyl-3-butynylamino)thieno[2,3-d]pyrimidine 1.72 g of the amine obtained in the above described stage, 1.72 g of 4-chlorothieno[2,3-d]pyrimidine, and 1.7 ml of triethylamine were added to 32 ml of N,N-dimethylformamide, and the obtained mixture was then stirred at 80° C. for 4 hours. Thereafter, the reaction solution was cooled, and 50 ml of water was then added thereto. The mixed solution was extracted with 50 ml of ethyl acetate twice. The organic layer was washed with 50 ml of water twice and then with 50 ml of a saturated brine once, and it was then dried over magnesium sulfate. The magnesium sulfate was filtrated, the organic layer was then concentrated, and the residue was then purified by column chromatography (Wako Gel C-200; toluene:ethyl acetate=4:1), so as to obtain 1.83 g of a product of interest.

Compounds Nos. 3 to 5 and 87 shown in Table 1 were synthesized by the same production method as described above.

(2) In the general formula (I), $R^1$=H, $R^2$=H, and $R^3$-$R^4$=thiophene (Synthesis of compound No. 1 in Table 1)

16 ml of tetrahydrofuran, 0.37 g of the 4-(4-trimethylsilanyl-3-butynylamino)thieno[2,3-d]pyrimidine obtained in (1) above, and 2.1 ml of a 1 M tetrabutylammonium fluoride tetrahydrofuran solution were added to a nitrogen-substituted flask, and the obtained mixture was then stirred at a room temperature for 5 hours. After completion of the stirring, 50 ml of a saturated ammonium chloride aqueous solution was added to the reaction solution, and the thus obtained solution was then extracted with 30 ml of dichloromethane twice. The organic layer was washed with 30 ml of a saturated brine, and it was then dried over magnesium sulfate. The magnesium sulfate was filtrated, and the organic layer was then concentrated. Thereafter, the residue was then purified by column chromatography (Wako Gel C-200; toluene:ethyl acetate=4:1), so as to obtain 0.20 g of 4-(3-butynylamino)thieno[2,3-d]pyrimidine.

Compounds No. 86 shown in Table 1 was synthesized by the same production method as described above.

(3) In the general formula (I), $R^1$=isobutyl, $R^2$=H, and $R^3$-$R^4$=thiophene (Synthesis of compound No. 7 in Table 1)

Stage A

6-Methyl-3-heptin-1-ol 22 ml of dry tetrahydrofuran and 25 ml of a 1 Methyl magnesium bromide tetrahydrofuran solution were added to a nitrogen-substituted flask, and thereafter, 2.9 ml of 4-methylpentine was slowly added dropwise to the mixed solution. The obtained solution was stirred at a room temperature for 1 hour, and thereafter, 25 ml of a 1.1 M ethylene oxide tetrahydrofuran solution was slowly added dropwise to the reaction solution at a room temperature. The obtained solution was further stirred at a room temperature overnight. Thereafter, 100 ml of a saturated ammonium chloride aqueous solution was added to the reaction solution, and the obtained solution was then extracted with 100 ml of diethyl ether twice. It was dried over magnesium sulfate. The magnesium sulfate was filtrated, and the organic layer was then concentrated. The generated alcohol was directly used in the subsequent reaction (yield: 3.78 g).

Stage B

2-(6-Methyl-3-heptynyl)isoindol-1,3-dione 168 ml of dry tetrahydrofuran, 3.78 g of the alcohol obtained in the above described stage, 4.06 g of phthalimide, and 7.21 g of triphenylphosphine were added to a nitrogen-substituted flask. To this solution, 13.9 ml of diethyl azodicarboxylate (40% toluene solution) was slowly added dropwise at a room temperature, and the obtained solution was stirred at a room temperature for 1 day. Thereafter, the reaction solution was concentrated, and 200 ml of water was then added to the residue. The obtained solution was extracted with 150 ml of ethyl acetate twice. The organic layer was washed with 200 ml of water and then with 200 ml of a saturated brine, and it was then dried over magnesium sulfate. The magnesium sulfate was filtrated, and the organic layer was then concentrated. Thereafter, the residue was purified by column chromatography (Wako Gel C-200; toluene), so as to obtain 5.08 g of a phthalimide compound.

Stage C

6-Methyl-3-heptynylamine 200 ml of methanol and 3.73 g of hydrazine monohydrate (80%) were added to 5.08 g of the phthalimide compound obtained in the above described stage, and the obtained mixture was then stirred overnight. Thereafter, the reaction solution was concentrated, the residue was then washed with 50 ml of chloroform, and it was then suspended in the washed chloroform. Insoluble residue were filtrated, and the filtrate was then concentrated, followed by drying under a reduced pressure, so as to obtain 1.65 g of amine.

Stage D

4-(6-Methyl-3-heptynylamino)thieno[2,3-d]pyrimidine 1.65 g of the amine obtained in the above described stage, 2.13 g of 4-chlorothieno[2,3-d]pyrimidine, and 1.9 ml of triethylamine were added to 42 ml of DMF, and the obtained mixture was then stirred at 85° C. for 4 hours. Thereafter the reaction solution was cooled, and 100 ml of water was then added thereto, followed by extraction with ethyl acetate twice. The organic layer was washed with 100 ml of water twice and then with 100 ml of a saturated brine once. The resultant and it was then dried over magnesium sulfate. The magnesium sulfate was filtrated, the organic layer was then concentrated, and the residue was then purified by column chromatography (Wako Gel C-200; toluene:ethyl acetate=4:1), so as to obtain 2.14 g of a product of interest.

Compounds Nos. 6, 8, 9, 88-91, and 94 shown in Table 1 were synthesized by the same production method as described above.

(4) In the general formula (I), $R^1$=phenyl, $R^2$=H, and $R^3$-$R^4$=thiophene (Synthesis of compound No. 10 in Table 1)

Stage A 2-(4-Phenyl-3-butynyl)isoindol-1,3-dione

Under a nitrogen atmosphere, 35 ml of tetrahydrofuran, 3.06 g of iodobenzene, and 9.0 ml of triethylamine were added to 535 mg of dichlorobis(triphenylphosphine)palladium, 145 mg of copper iodide, and 3.00 g of N-(3-butynyl)phthalimide. The obtained mixture was stirred under reflux for 4 hours. After completion of the stirring, the reaction solution was cooled to a room temperature, and a solid was then filtrated. The filtrate was concentrated, and the residue was then purified by column chromatography (Wako Gel C-200; toluene:ethyl acetate=4:1), so as to obtain 3.70 g of a phthalimide compound.

Stage B

4-Phenyl-3-butynylamine 135 ml of methanol and 2.52 g of hydrazine monohydrate (80%) were added to 3.70 g of the phthalimide compound obtained in the above described stage, and the obtained mixture was then stirred overnight. After completion of the stirring, the reaction solution was concentrated, and the residue was then suspended in 50 ml of chloroform. Insoluble residue were filtrated, and the filtrate was then concentrated, followed by drying under a reduced pressure, so as to obtain 1.94 g of amine.

Stage C 4-(4-Phenyl-3-butynylamino)thieno[2,3-d]pyrimidine 1.94 g of the amine obtained in the above described stage, 1.90 g of 4-chlorothieno[2,3-d]pyrimidine, and 1.9 ml of triethylamine were added to 31 ml of N,N-dimethylformamide, and the obtained mixture was then stirred at 85° C. for 4 hours. Thereafter, the reaction solution was cooled, 50 ml of water was then added thereto, and the obtained solution was then extracted with 50 ml of ethyl acetate twice. The organic layer was washed with 30 ml of water twice and then with 30 ml of a saturated brine once. The resultant was dried over magnesium sulfate. The magnesium sulfate was filtrated, and the organic layer was then concentrated. The residue was then purified by column chromatography (Wako Gel C-200; toluene:ethyl ethyl acetate=4:1), so as to obtain 1.68 g of a product of interest.

Compounds Nos. 11-28, 32-54, 64-67, 84, 85, 96-100, 102-126, 128, 130-209, 211-214, 306-342, and 355-380 shown in Table 1 were synthesized by the same production method as described above.

(5) In the general formula (I), $R^1$=phenyl, $R^2$=methyl, and $R^3$-$R^4$=thiophene (Synthesis of compound No. 229 in Table 1)

Stage A 2-(1-Methyl-3-butynyl)isoindol-1,3-dione 400 ml of dry tetrahydrofuran, 5.00 g of 4-pentin-2-ol, 9.65 g of phthalimide, and 17.13 g of triphenylphosphine were added to a nitrogen-substituted flask. Thereafter, 30 ml of diethyl azodicarboxylate (40% toluene solution) was slowly added dropwise to the obtained solution at a room temperature, and the obtained mixture was then stirred at a room temperature for 1 day. Thereafter, the reaction solution was concentrated, and 300 ml of water was then added to the residue, followed by extraction with 250 ml of ethyl acetate twice. The organic layer was washed with 200 ml of water and then with 200 ml of a saturated brine. The resultant was dried over magnesium sulfate. The magnesium sulfate was filtrated, and the organic layer was then concentrated. The residue was then purified by column chromatography (Wako Gel C-200; toluene), so as to obtain 2.20 g of a phthalimide compound.

Stage B 2-(1-Methyl-4-phenyl-3-butynyl)isoindol-1,3-dione

Under a nitrogen atmosphere, 24 ml of tetrahydrofuran, 2.11 g of iodobenzene, and 6.2 ml of triethylamine were added to 367 mg of dichlorobis(triphenylphosphine)palladium, 100 mg of copper iodide, and 2.20 g of the phthalimide compound obtained in the above described stage. The obtained mixture was stirred under reflux for 8 hours. After completion of the stirring, the reaction solution was cooled to a room temperature, and a solid was then filtrated. The filtrate was concentrated, and the residue was then purified by column chromatography (Wako Gel C-200; toluene:ethyl acetate=9:1), so as to obtain 1.82 g of a phthalimide compound.

Stage C

1-Methyl-4-phenyl-3-butynylamine 63 ml of methanol and 1.18 g of hydrazine monohydrate (80%) were added to 1.82 g of the phthalimide compound obtained in the above described stage, and the obtained mixture was then stirred overnight. After completion of the stirring, the reaction solution was concentrated, and the residue was then suspended in 30 ml of chloroform. Insoluble residue were filtrated, and the filtrate was then concentrated, followed by drying under a reduced pressure, so as to quantitatively obtain amine.

Stage D 4-(1-Methyl-4-phenyl-3-butynylamino)thieno[2,3-d]pyrimidine

The above obtained amine, 1.02 g of 4-chlorothieno[2,3-d]pyrimidine, and 0.9 ml of triethylamine were added to 20 ml of N,N-dimethylformamide, and the obtained mixture was then stirred at 80° C. for 4 hours. Thereafter, the reaction solution was cooled, and 30 ml of water was then added thereto, followed by extraction with 50 ml of ethyl acetate twice. The organic layer was washed with 30 ml of water twice and then with 30 ml of a saturated brine once. The resultant was dried over magnesium sulfate. The magnesium sulfate was filtrated, and the organic layer was then concentrated. The residue was then purified by column chromatography (Wako Gel C-200; toluene:ethyl acetate=9:1), so as to obtain 0.46 g of a product of interest.

Compounds Nos. 230-295, 298, 343-354, and 381-389 shown in Table 1 were synthesized by the same production method as described above.

(6) In the general formula (I), $R^1$=4-methoxycarbonylphenyl, $R^2$=H, and $R^3$-$R^4$=thiophene (Synthesis of compound No. 29 in Table 1)

Under a nitrogen atmosphere, 11 ml of tetrahydrofuran, 1.25 g of methyl 4-iodobenzoate, and 2.9 ml of triethylamine were added to 170 mg of dichlorobis(triphenylphosphine) palladium, 46 mg of copper iodide, and 0.97 g of the 4-[(3-butynyl)amino]thieno[2,3-d]pyrimidine obtained in (2) above. The obtained mixture was stirred under reflux for 4 hours. After completion of the stirring, the reaction solution was cooled to a room temperature, and a solid was then filtered. The filtrate was concentrated, and the residue was then purified by column chromatography (Wako Gel C-200; toluene:ethyl acetate=1:1), so as to obtain 1.09 g of 4-[4-(thieno[2,3-d]pyrimidin-4-ylamino)-1-butynyl]benzoate.

Compounds Nos. 30, 31, 92, 93, 95, 127, and 129 shown in Table 1 were synthesized by the same production method as described above.

(7) In the general formula (I), $R^1$=2-phenyl-4-thiazolyl, $R^2$=H, and $R^3$-$R^4$=thiophene (Synthesis of compound No. 76 in Table 1)

Stage A

4-Bromo-2-phenylthiazole

A flask containing 238 mg of tetrakis(triphenylphosphine) palladium, 0.55 g of phenyl boronic acid and 1.00 g of 2,4-dibromothiazole was subjected to nitrogen substitution. To this flask, 30 ml of toluene, 6.1 ml of ethanol, and 9.1 ml of a 2 M sodium carbonate aqueous solution were added, and the obtained mixture was then stirred under reflux for 6 hours. Thereafter, the reaction solution was cooled to a room temperature, and 50 ml of water was then added thereto, followed by extraction with 50 ml of ethyl acetate twice. The organic layer was washed with 30 ml of a saturated brine, and it was then dried over magnesium sulfate. The magnesium sulfate was filtrated, and the organic layer was then concentrated. The residue was then purified by column chromatography (Wako Gel C-200; hexane:ethyl acetate=14:1), so as to obtain 0.71 g of 2-phenyl-4-bromothiazole.

Stage B

2-[4-(2-Phenylthiazol-4-yl)-3-butynyl]isoindol-1,3-dione

Under a nitrogen atmosphere, 15 ml of tetrahydrofuran, 1.50 g of the 2-phenyl-4-bromothiazole obtained in the above described stage, and 3.8 ml of triethylamine were added to 221 mg of dichlorobis(triphenylphosphine)palladium, 60 mg of copper iodide, and 1.24 g of N-(3-butynyl)phthalimide. The obtained mixture was stirred under reflux for 4 hours. After completion of the stirring, the reaction solution was cooled to a room temperature, and a solid was then filtrated. The filtrate was concentrated, and the residue was then purified by column chromatography (Wako Gel C-200; toluene:ethyl acetate=9:1), so as to obtain 1.24 g of a phthalimide compound.

Stage C 4-(2-Phenylthiazol-4-yl)-3-butynylamine 35 ml of methanol and 0.65 g of hydrazine monohydrate (80%) were added to 1.24 g of the phthalimide compound obtained in the above described stage, and the obtained mixture was then stirred overnight. After completion of the stirring, the reaction solution was concentrated, and the residue was then suspended in 20 ml of chloroform. Insoluble residue were filtrated, and the filtrate was then concentrated, followed by drying under a reduced pressure, so as to obtain 0.96 g of amine.

Stage D

4-[4-(2-Phenylthiazol-4-yl)-3-butynylamino]thieno[2,3-d]pyrimidine 0.96 g of the amine obtained in the above described stage, 0.68 g of 4-chlorothieno[2,3-d]pyrimidine, and 0.6 ml of triethylamine were added to 13 ml of N,N-dimethylformamide. The obtained mixture was stirred at 85° C. for 4 hours. Thereafter, the reaction solution was cooled, and 25 ml of water was then added thereto, followed by extraction with 30 ml of ethyl acetate twice. The organic layer was washed with 30 ml of water twice and then with 30 ml of a saturated brine once. The resultant was dried over magnesium sulfate. The magnesium sulfate was filtrated, and the organic layer was then concentrated. The residue was purified by column chromatography (Wako Gel C-200; toluene:ethyl acetate=2:1), so as to obtain 0.70 g of a product of interest.

Compounds Nos. 77-82 shown in Table 1 were synthesized by the same production method as described above.

(8) In the general formula (I), $R^1$=(2-benzyl)-4-thiazolyl, $R^2$=H, and $R^3$-$R^4$=thiophene (Synthesis of compound No. 75 in Table 1)

Stage A

2-Benzyl-4-bromothiazole

A flask containing 267 mg of tetrakis(triphenylphosphine) palladium and 1.00 g of 2,4-dibromothiazole was subjected to nitrogen substitution. To this flask, 9 ml of dry tetrahydrofuran and 9.9 ml of a 0.5 M benzylzinc bromide tetrahydrofuran solution were added. The obtained mixture was stirred at 70° C. for 6 hours. Thereafter, the reaction solution was cooled to a room temperature, and 30 ml of water was then added thereto, followed by extraction with 30 ml of ethyl acetate twice. The organic layer was washed with 30 ml of water twice and then with 30 ml of a saturated brine once. The resultant was dried over magnesium sulfate. The magnesium sulfate was filtrated, and the organic layer was then concentrated. The residue was then purified by column chromatography (Wako Gel C-200; hexane:ethyl acetate=14:1), so as to obtain 0.36 g of 2-benzyl-4-bromothiazole.

Stage B

2-[4-(2-Benzylthiazol-4-yl)-3-butynyl]isoindol-1,3-dione

Under a nitrogen atmosphere, 9 ml of tetrahydrofuran, 1.02 g of the 2-benzyl-4-bromothiazole obtained in the above described stage, and 2.3 ml of triethylamine were added to 143 mg of dichlorobis(triphenylphosphine)palladium, 38 mg of copper iodide, and 0.80 g of N-(3-butynyl)phthalimide. The obtained mixture was stirred under reflux for 4 hours. After completion of the stirring, the reaction solution was cooled to a room temperature, and a solid was then filtrated. The filtrate was concentrated, and the residue was then purified by column chromatography (Wako Gel C-200; toluene: ethyl acetate=9:1), so as to obtain 1.00 g of a phthalimide compound.

Stage C 4-(2-Benzylthiazol-4-yl)-3-butynylamine 26 ml of methanol and 0.50 g of hydrazine monohydrate (80%) were added to 1.00 g of the phthalimide compound obtained in the above described stage, and the obtained mixture was then stirred overnight. After completion of the stirring, the reaction solution was concentrated, and the residue was then suspended in 25 ml of chloroform. Insoluble residue were filtrated, and the filtrate was then concentrated, followed by drying under a reduced pressure, so as to obtain 0.12 g amine.

Stage D

4-[4-(2-Benzylthiazol-4-yl)-3-butynylamino]thieno[2,3-d]pyrimidine 0.12 g of the amine obtained in the above described stage, 0.08 g of 4-chlorothieno[2,3-d]pyrimidine, and 0.1 ml of triethylamine were added to 1.5 ml of N,N-dimethylformamide, and the obtained mixture was then stirred at 85° C. for 4 hours. Thereafter, the reaction solution was cooled, and 15 ml of water was then added thereto, followed by extraction with 20 ml of ethyl acetate twice. The organic layer was washed with 20 ml of water twice and then with 20 ml of a saturated brine once. The resultant was dried over magnesium sulfate. The magnesium sulfate was filtrated, and the organic layer was then concentrated. The residue was purified by column chromatography (Wako Gel C-200; toluene:ethyl acetate=1:1), so as to obtain 0.07 g of a product of interest.

(9) In the general formula (I), $R^1$=2-phenoxy-4-thiazolyl, $R^2$=H, and $R^3$-$R^4$=thiophene (Synthesis of compound No. 83 in Table 1)

Stage A

4-Bromo-2-phenoxythiazole 3.00 g of 2,4-dibromothiazole, 1.74 g of phenol, and 3.44 g of potassium carbonate were added to 75 ml of N,N-dimethylformamide, and the obtained mixture was then stirred at 140° C. for 6 hours. Thereafter, the reaction solution was cooled to a room temperature, and 100 ml of water was then added thereto, followed by extraction with 100 ml of ethyl acetate twice. The organic layer was washed with 100 ml of water twice and then with 50 ml of a saturated brine once. The resultant was dried over magnesium sulfate. The magnesium sulfate was filtrated, and the organic layer was then concentrated. The residue was then purified by column chromatography (Wako Gel C-200; hexane:ethyl acetate=9:1), so as to obtain 2.86 g of an ether compound.

Stage B

2-[4-(2-Phenoxythiazol-4-yl)-3-butynyl]isoindol-1,3-dione

Under a nitrogen atmosphere, 26 ml of tetrahydrofuran, 2.86 g of the ether compound obtained in the above described stage, and 6.9 ml of triethylamine were added to 399 mg of dichlorobis(triphenylphosphine)palladium, 109 mg of copper iodide, and 2.24 g of N-(3-butynyl)phthalimide. The obtained mixture was stirred under reflux for 4 hours. After completion of the stirring, the reaction solution was cooled to a room temperature, and a solid was then filtrated. The filtrate was concentrated, and the residue was then purified by column chromatography (Wako Gel C-200; toluene:ethyl acetate=9:1), so as to obtain 3.50 g of a phthalimide compound.

Stage C 4-(2-Phenoxythiazol-4-yl)-3-butynylamine 90 ml of methanol and 1.76 g of hydrazine monohydrate (80%) were added to 3.50 g of the phthalimide compound obtained in the above described stage, and the obtained mixture was then stirred overnight. After completion of the stirring, the reaction solution was concentrated, and the residue was then suspended in 40 ml of chloroform. Insoluble residue were filtrated, and the filtrate was then concentrated, followed by drying under a reduced pressure, so as to obtain 2.24 g of amine.

Stage D

4-[4-(2-Phenoxythiazol-4-yl)-3-butynylamino]thieno[2,3-d]pyrimidine 2.24 g of the amine obtained in the above described stage, 1.45 g of 4-chlorothieno[2,3-d]pyrimidine, and 1.3 ml of triethylamine were added to 27 ml of N,N-dimethylformamide, and the obtained mixture was then stirred at 85° C. for 4 hours. Thereafter, the reaction solution was cooled, and 50 ml of water was then added thereto, followed by extraction with 50 ml of ethyl acetate twice. The organic layer was washed with 50 ml of water twice and then with 30 ml of a saturated brine once. The resultant was dried over magnesium sulfate. The magnesium sulfate was filtrated, and the organic layer was then concentrated. The residue was purified by column chromatography (Wako Gel C-200; toluene:ethyl acetate=1:1), so as to obtain 2.79 g of a product of interest.

Compounds Nos. 215-228 shown in Table 1 were synthesized by the same production method as described above.

(10) In the general formula (I), $R^1$=4-thiazolyl, $R^2$=H, and $R^3$-$R^4$=thiophene (Synthesis of compound No. 61 in Table 1)

Stage A 2-(4-Thiazolyl-3-butynyl)isoindol-1,3-dione

Under a nitrogen atmosphere, 78 ml of tetrahydrofuran, 5.49 g of 4-bromothiazole, and 20.3 ml of triethylamine were added to 1184 mg of dichlorobis(triphenylphosphine)palladium, 322 mg of copper iodide, and 6.64 g of N-(3-butynyl)phthalimide. The obtained mixture was stirred under reflux for 5 hours. After completion of the stirring, the reaction solution was cooled to a room temperature, and a solid was then filtrated. The filtrate was concentrated, and the residue was then purified by column chromatography (Wako Gel C-200; toluene:ethyl acetate=4:1), so as to obtain 6.35 g of a phthalimide compound.

Stage B

4-Thiazolyl-3-butynylamine 115 ml of ethanol, 115 ml of water, and 115 ml of an ion exchange resin (Diaion WA21J Resin) were added to 6.35 g of the phthalimide compound obtained in the above described stage, and the obtained mixture was then stirred at 90° C. for 2 hours. Thereafter, the reaction solution was cooled to a room temperature, and the ion exchange resin was then filtrated. The reaction solution was concentrated under a reduced pressure, so as to obtain 2.48 g of amine.

Stage C

4-[(4-Thiazolyl-3-butynyl)amino]thieno[2,3-d]pyrimidine 2.48 g of the amine obtained in the above described stage, 2.60 g of 4-chlorothieno[2,3-d]pyrimidine, and 2.3 ml of triethylamine were added to 50 ml of N,N-dimethylformamide, and the obtained mixture was then stirred at 85° C. for 2.5 hours. Thereafter, the reaction solution was cooled, and 1 L of water was then added thereto. The precipitated solid was filtrated, and the filtrate was then washed with 100 ml of water twice, followed by vacuum drying, so as to obtain 3.00 g of a product of interest.

Compounds Nos. 55-60, 62, 63, 68-74, 101, and 210 shown in Table 1 were synthesized by the same production method as described above.

(11) In the general formula (I), $R^1$=H, $R^2$=phenyl, and $R^3$-$R^4$=benzene (Synthesis of compound No. 300 in Table 1)

Stage A

1-Phenyl-3-butynylamine

Under a nitrogen atmosphere, a 1 M lithium bistrimethylsilylamide-tetrahydrofuran solution was added dropwise at 0° C. to a solution prepared by adding 2.97 g of benzaldehyde to 4 ml of tetrahydrofuran. The obtained solution was stirred at 0° C. for 15 minutes and then at a room temperature for 1 hour. This solution is defined as solution A.

Under a nitrogen atmosphere, 4 ml of tetrahydrofuran and 0.63 g of 1,2-dibromoethane were added to 6.03 g of zinc powders, and the obtained mixture was then stirred under reflux for 1 hour. After completion of the stirring, the reaction solution was cooled to a room temperature. Thereafter, a tetrahydrofuran solution of chlorotrimethylsilane (0.37 g of chlorotrimethylsilane+8 ml of tetrahydrofuran) was added to the reaction solution at a room temperature. The obtained solution was cooled to –10° C., and a tetrahydrofuran solution of propargyl bromide (10.00 g of propargyl bromide+8 ml of tetrahydrofuran) was then added dropwise thereto. The obtained mixture was further stirred at –10° C. for 1.5 hours. After completion of the stirring, solution A was added dropwise to this solution at –10° C. After completion of the dropwise addition, the temperature of the reaction solution was gradually increased to a room temperature, and the solution was then stirred at a room temperature overnight. Thereafter, the reaction solution was cooled to 0° C., and 20 ml of a saturated potassium carbonate solution was then added thereto. Then, 65 ml of water and 30 ml of methyl t-butyl ether were added thereto. The organic layer was subjected to liquid separation, and the water layer was further extracted with 30 ml of methyl t-butyl ether five times. The gathered organic layers were concentrated, and the residue was then dried in a vacuum. Water was added to this residue, and the obtained solution was then extracted with 30 ml of methyl t-butyl ether twice. The organic layer was washed with 30 ml of water twice and then with 30 ml of a saturated brine. The resultant was dried over magnesium sulfate. The magnesium sulfate was filtrated, and the filtrate was then concentrated, followed by vacuum drying, so as to obtain 3.38 g of amine.

Stage B

4-[(1-Phenyl-3-butynyl)amino]quinazoline 0.49 g of the amine obtained in the above described stage, 0.50 g of 4-chloroquinazoline, and 0.7 ml of triethylamine were added to 11 ml of N,N-dimethylformamide, and the obtained mixture was then stirred at 85° C. for 3 hours. Thereafter, the reaction solution was cooled, and 50 ml of water was then added thereto, followed by extraction with 20 ml of ethyl acetate twice. The organic layer was washed with 20 ml of water twice and then with 20 ml of a saturated brine once. The resultant was dried over magnesium sulfate. The magnesium sulfate was filtrated, and the organic layer was then concentrated. The residue was then purified by column chromatography (Wako Gel C-200; toluene:ethyl acetate=1:1), so as to obtain 0.69 g of a product of interest.

(12) In the general formula (I), $R^1$=phenyl, $R^2$=phenyl, and $R^3$-$R^4$=benzene (Synthesis of compound No. 301 in Table 1)

Under a nitrogen atmosphere, 17 ml of tetrahydrofuran, 1.49 g of iodobenzene, and 4.5 ml of triethylamine were added to 278 mg of dichlorobis(triphenylphosphine)palladium, 71 mg of copper iodide, and 2.00 g of the 4-[(1-phenyl-3-butynyl)amino]quinazoline obtained in (11) above. The obtained mixture was stirred under reflux for 3 hours. After completion of the stirring, the reaction solution was cooled to a room temperature, and a solid was then filtrated. The filtrate was concentrated, and the residue was then purified by column chromatography (Wako Gel C-200; toluene:ethyl acetate=4:1), so as to obtain 1.03 g of 4-[(1,4-diphenyl-3-butynyl)amino]quinazoline.

Compound No. 302 shown in Table 1 was synthesized by the same production method as described above.

(13) In the general formula (I), $R^1$=phenyl, $R^2$=ethoxycarbonyl, and $R^3$-$R^4$=benzene (Synthesis of compound No. 303 in Table 1)

Stage A

N-(diphenylmethylene)-2-(3-phenyl)propargyl glycine ethyl 50 ml of acetonitrile, 3.00 g of N-(diphenylmethylene) glycine ethyl, 2.60 g of 3-phenylpropargyl bromide, 2.32 g of potassium carbonate, and 381 mg of tetrabutylammonium hydrogen sulfate were added to a nitrogen-substituted flask. The obtained mixture was stirred at 70° C. for 24 hours. Thereafter, the reaction solution was cooled to a room temperature, and 100 ml of ethyl acetate was then added thereto, followed by filtration with Celite. The filtrate was concentrated, and the residue was then purified by flash chromatography (manufactured by Biotage AB; Isolera™), so as to obtain 2.00 g of N-(diphenylmethylene)-2-(3-phenyl)propargyl glycine ethyl.

Stage B 2-(3-Phenyl)propargyl glycine ethyl 20 ml of diethyl ether, 1.80 g of the alcohol obtained in the above described stage, and 20 ml of 1 N hydrochloric acid were added to a nitrogen-substituted flask, and the obtained mixture was then stirred at a room temperature for 1 day. Thereafter, 30 ml of sodium bicarbonate water was added to the reaction solution, and the obtained solution was extracted with 50 ml of ethyl acetate twice and was then dried over sodium sulfate. The sodium sulfate was filtrated, and the organic layer was then concentrated. The residue was purified by flash chromatography (manufactured by Biotage AB; Isolera™), so as to obtain 985 mg of 2-(3-phenyl)propargyl glycine ethyl.

Stage C

4-[2-Ethoxycarbonyl-4-phenyl-3-butynylamino] quinazoline 985 mg of the amine obtained in the above described stage, 720 mg of 4-chloroquinazoline, and 1 ml of triethylamine were added to 15 ml of N,N-dimethylformamide, and the obtained mixture was then stirred at 80° C. for 4 hours. Thereafter, the reaction solution was cooled, and 40 ml of water was then added thereto, followed by extraction with 70 ml of ethyl acetate twice. The organic layer was washed with 40 ml of a saturated brine twice, and it was then dried over sodium sulfate. The sodium sulfate was filtrated, and the organic layer was then concentrated. The residue was purified by flash chromatography (manufactured by Biotage AB; Isolera™), so as to obtain 1.10 g of a product of interest.

Compound No. 304 shown in Table 1 was synthesized by the same production method as described above.

(14) In the general formula (I), $R^1$=phenyl, $R^2$=hydroxymethyl, and $R^3$-$R^4$=benzene (Synthesis of compound No. 299 in Table 1)

200 mg of 4-[2-ethoxycarbonyl-4-phenyl-3-butynylamino]quinazoline and 1 ml of a 1 M tetrahydrofuran solution of lithium dimethylamino borohydride were added to 10 ml of tetrahydrofuran, and the obtained mixture was then stirred at a room temperature for 1 hour. Thereafter, 20 ml of 1 N hydrochloric acid was added to the reaction solution, and the obtained mixture was then stirred for 10 minutes. Thereafter, sodium bicarbonate water was added to the reaction solution for neutralization. The obtained solution was extracted with 40 ml of ethyl acetate twice, and it was then dried over sodium sulfate. The sodium sulfate was filtrated, and the organic layer was then concentrated. The residue was then purified by flash chromatography (manufactured by Biotage AB; Isolera™), so as to obtain 37 mg of 4-[2-hydroxymethyl-4-phenyl-3-butynylamino]quinazoline.

(15) In the general formula (I), $R^1$=phenyl, $R^2$=methylaminocarbonyl, and $R^3$-$R^4$=benzene (Synthesis of compound No. 305 in Table 1)

130 mg of 4-[2-ethoxycarbonyl-4-phenyl-3-butynylamino]quinazoline and 3 ml of a 40% methylamine methanol solution were added to 5 ml of tetrahydrofuran, and the obtained mixture was stirred at 60° C. for 1 hour, and then at a room temperature over day and night. Thereafter, the reaction solution was concentrated, and the residue was then purified by flash chromatography (manufactured by Biotage AB; Isolera™), so as to obtain 113 mg of 4-[2-methylaminocarbonyl-4-phenyl-3-butynylamino]quinazoline.

(16) In the general formula (I), $R^1$=phenyl, $R^2$=vinyl, and $R^3$-$R^4$=benzene (Synthesis of compound No. 296 in Table 1)

Stage A

2-Vinyl-4-phenyl-3-butyn-ol 40 ml of dry tetrahydrofuran and 20 ml of a 1.6 M n-butyl lithium solution were added to a nitrogen-substituted flask at −78° C., and the obtained mixture was then stirred for 30 minutes. Thereafter, 3.5 ml of a trifluoroborane tetrahydrofuran complex was slowly added dropwise to the reaction solution. The obtained solution was further stirred at −78° C. for 15 minutes, and 2.00 g of 1,3-butadiene monoepoxide was slowly added dropwise thereto. The thus obtained mixture was further stirred at −78° C. for 3 hours. Thereafter, 50 ml of a saturated ammonium chloride aqueous solution was added to the reaction solution, and the obtained solution was extracted with 100 ml of ethyl acetate once and was then dried over sodium sulfate. The sodium sulfate was filtrated, and the organic layer was then concentrated. The residue was purified by flash chromatography (manufactured by Biotage AB; Isolera™), so as to obtain 1.80 g of 2-vinyl-4-phenyl-3-butyn-ol.

Stage B 2-(2-Vinyl-4-phenyl-3-butynyl)isoindol-1,3-dione 55 ml of toluene, 1.80 g of 2-vinyl-4-phenyl-3-butyn-ol, 1.93 g of phthalimide, and 3.45 g of triphenylphosphine were added to a nitrogen-substituted flask. Then, 5.30 g of diethyl azodicarboxylate (40% toluene solution) was slowly added dropwise to the above obtained solution under cooling on ice. The temperature was increased to a room temperature, and the obtained mixture was then stirred for 1 day. Thereafter, the reaction solution was concentrated, and 200 ml of diethyl ether was then added to the residue. The appearing solid was removed by filtration. The residue was concentrated, and it was then purified by flash chromatography (manufactured by Biotage AB; Isolera™), so as to obtain 1.00 g of 2-(2-vinyl-4-phenyl-3-butynyl)isoindol-1,3-dione.

Stage C

2-Vinyl-4-phenyl-3-butynylamine 20 ml of methanol and 10 ml of a methylamine solution (40% methanol solution) were added to 1.00 g of 2-(2-vinyl-4-phenyl-3-butynyl)isoindol-1,3-dione, and the obtained mixture was then stirred at 60° C. for 1 hour. Thereafter, the reaction solution was concentrated, and it was then successively washed with 50 ml of ethyl acetate and 50 ml of diethyl ether. Thereafter, the filtrate was concentrated, so as to obtain 550 mg of amine as a crude product.

Stage D

4-[2-Vinyl-4-phenyl-3-butynylamino]quinazoline 550 mg of 2-vinyl-4-phenyl-3-butynylamine, 500 mg of 4-chloroquinazoline, and 636 μl of triethylamine were added to 15 ml of DMF, and the obtained mixture was then stirred at 80° C. for 5 hours. Thereafter, the reaction solution was cooled, and 20 ml of water was then added thereto, followed by extraction with 50 ml of ethyl acetate twice. The organic layer was washed with 50 ml of a saturated brine twice, and it was then dried over sodium sulfate. The sodium sulfate was filtrated, and the organic layer was then concentrated. The residue was purified using an automated flash chromatography instrument (manufactured by Biotage AB; Isolera™), so as to obtain 750 mg of a product of interest.

Compound No. 297 shown in Table 1 was synthesized by the same production method as described above.

It is to be noted that commercially available products were used as 4-chlorothieno[2,3-d]pyrimidine, 4-chlorothieno[3,2-d]pyrimidine, 4-chloro-7-methylthieno[3,2-d]pyrimidine, 4-chloroquinazoline, 4,6-dichloro-5-methylpyrimidine, 6-chloropurine, 6-chloro-7-deazapurine, 4,6-dichloropyrimidine, 4-chloro-6-methylpyrimidine and 4,6-dichloro-5-nitropyrimidine, and that 4,6-dichloro-5-phenylpyrimidine, 4,5-dichloro-6-(1-fluoroethyl)pyrimidine and 4-chloro-5-iodo-6-(1-fluoroethyl)pyrimidine were produced in accordance with the methods described in WO2006/138734, Japanese Patent Laid-Open No. 2000-7662 and Japanese Patent Laid-Open No. 2002-275164, respectively.

The thus synthesized compounds [I] and the physical properties thereof are shown in Table 1 (Table 1-1 to Table 1-71). In addition, the NMR data of the compounds [I] are shown in Table 2 (Table 2-1 to Table 2-25). It is to be noted that, in the present specification, the term "Table 1" is used as a generic name (comprehensive name) of Table 1-1 to Table 1-71, and the term "Table 2" is used as a generic name (comprehensive name) of Table 2-1 to Table 2-25.

TABLE 1-1

| Compound No. | Structure | Physical property |
|---|---|---|
| 1 | 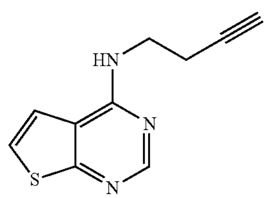 | m.p. 117~119° C. |
| 2 | 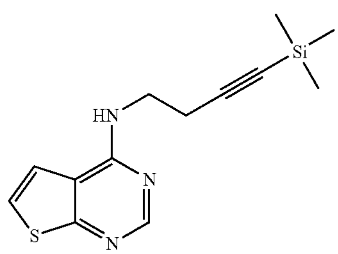 [SMILES: C[Si](C)(C)C#CCCNc1ncnc2sccc12] | m.p. 144~146° C. |
| 3 | 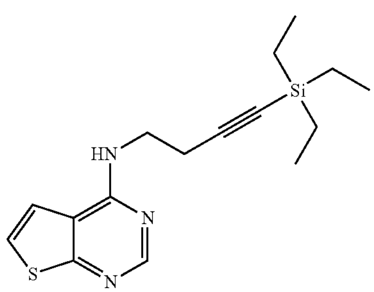 [SMILES: CC[Si](C#CCCNc1ncnc2sccc12)(CC)CC] | m.p. 152~154° C. |
| 4 | 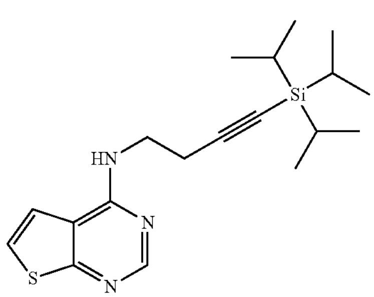 [SMILES: CC(C)[Si](C#CCCNc1ncnc2sccc12)(C(C)C)C(C)C] | m.p. 196~198° C. |

TABLE 1-1-continued

| Compound No. | Structure | Physical property |
|---|---|---|
| 5 | 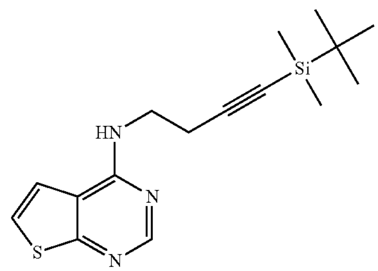 [SMILES: CC(C)(C)[Si](C)(C)C#CCCNc1ncnc2sccc12] | m.p. 190~192° C. |
| 6 | 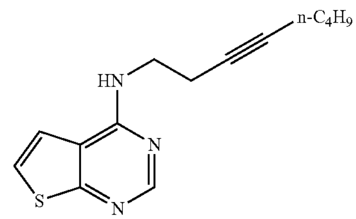 | m.p. 66~68° C. |

TABLE 1-2

| Compound No. | Structure | Physical property |
|---|---|---|
| 7 | 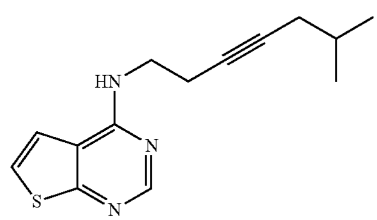 [SMILES: CC(C)CC#CCCNc1ncnc2sccc12] | m.p. 94~95° C. |
| 8 | 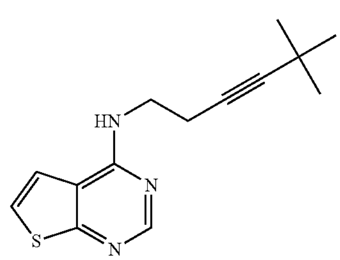 [SMILES: CC(C)(C)C#CCCNc1ncnc2sccc12] | m.p. 146~147° C. |
| 9 | 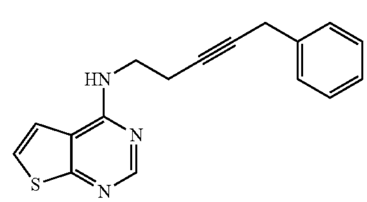 [SMILES: C(#CCc1ccccc1)CCNc1ncnc2sccc12] | m.p. 90~92° C. |

TABLE 1-2-continued

| Compound No. | Structure | Physical property |
|---|---|---|
| 10 | (thieno[2,3-d]pyrimidin-4-yl)NH-CH2CH2-C≡C-phenyl | m.p. 129~132° C. |
| 11 | (thieno[2,3-d]pyrimidin-4-yl)NH-CH2CH2-C≡C-(2-F-phenyl) | m.p. 141~144° C. |
| 12 | (thieno[2,3-d]pyrimidin-4-yl)NH-CH2CH2-C≡C-(3-F-phenyl) | m.p. 118~122° C. |

TABLE 1-3

| Compound No. | Structure | Physical property |
|---|---|---|
| 13 | (thieno[2,3-d]pyrimidin-4-yl)NH-CH2CH2-C≡C-(4-F-phenyl) | m.p. 147~149° C. |
| 14 | (thieno[2,3-d]pyrimidin-4-yl)NH-CH2CH2-C≡C-(2-Cl-phenyl) | m.p. 145~147° C. |
| 15 | (thieno[2,3-d]pyrimidin-4-yl)NH-CH2CH2-C≡C-(3-Cl-phenyl) | m.p. 131~135° C. |
| 16 | (thieno[2,3-d]pyrimidin-4-yl)NH-CH2CH2-C≡C-(4-Cl-phenyl) | m.p. 130~132° C. |
| 17 | (thieno[2,3-d]pyrimidin-4-yl)NH-CH2CH2-C≡C-(2-CH3-phenyl) | Oily product |
| 18 | (thieno[2,3-d]pyrimidin-4-yl)NH-CH2CH2-C≡C-(3-CH3-phenyl) | m.p. 120~123° C. |

TABLE 1-4

| Compound No. | Structure | Physical property |
|---|---|---|
| 19 | (thieno[2,3-d]pyrimidin-4-yl)NH-CH2CH2-C≡C-(4-CH3-phenyl) | m.p. 125~127° C. |

TABLE 1-4-continued

| Compound No. | Structure | Physical property |
|---|---|---|
| 20 | thieno[2,3-d]pyrimidin-4-yl-NH-CH₂CH₂-C≡C-(4-tert-butylphenyl) | Resinoid product |
| 21 | thieno[2,3-d]pyrimidin-4-yl-NH-CH₂CH₂-C≡C-(2-OMe-phenyl) | m.p. 127~129° C. |
| 22 | thieno[2,3-d]pyrimidin-4-yl-NH-CH₂CH₂-C≡C-(3-OMe-phenyl) | m.p. 141~143° C. |
| 23 | thieno[2,3-d]pyrimidin-4-yl-NH-CH₂CH₂-C≡C-(4-OMe-phenyl) | Resinoid product |
| 24 | thieno[2,3-d]pyrimidin-4-yl-NH-CH₂CH₂-C≡C-(3,4-diOMe-phenyl) | m.p. 182~184° C. |

TABLE 1-5

| Compound No. | Structure | Physical property |
|---|---|---|
| 25 | thieno[2,3-d]pyrimidin-4-yl-NH-CH₂CH₂-C≡C-(2-CF₃-phenyl) | m.p. 116~117° C. |
| 26 | thieno[2,3-d]pyrimidin-4-yl-NH-CH₂CH₂-C≡C-(3-CF₃-phenyl) | m.p. 123~125° C. |
| 27 | thieno[2,3-d]pyrimidin-4-yl-NH-CH₂CH₂-C≡C-(4-CF₃-phenyl) | m.p. 129~134° C. |
| 28 | thieno[2,3-d]pyrimidin-4-yl-NH-CH₂CH₂-C≡C-(3,5-diCF₃-phenyl) | m.p. 163~166° C. |
| 29 | thieno[2,3-d]pyrimidin-4-yl-NH-CH₂CH₂-C≡C-(2-CO₂Me-phenyl) | m.p. 113~114° C. |
| 30 | thieno[2,3-d]pyrimidin-4-yl-NH-CH₂CH₂-C≡C-(3-CO₂Me-phenyl) | m.p. 163~166° C. |

TABLE 1-6

| Compound No. | Structure | Physical property |
|---|---|---|
| 31 | 4-(CO2Me)C6H4-C≡C-CH2CH2-NH-thieno[2,3-d]pyrimidin-4-yl | m.p. 145~146° C. |
| 32 | 2-(OCF3)C6H4-C≡C-CH2CH2-NH-thieno[2,3-d]pyrimidin-4-yl | m.p. 81~83° C. |
| 33 | 3-(OCF3)C6H4-C≡C-CH2CH2-NH-thieno[2,3-d]pyrimidin-4-yl | m.p. 98~101° C. |
| 34 | 4-(OCF3)C6H4-C≡C-CH2CH2-NH-thieno[2,3-d]pyrimidin-4-yl | m.p. 96~99° C. |
| 35 | 2-(CN)C6H4-C≡C-CH2CH2-NH-thieno[2,3-d]pyrimidin-4-yl | m.p. 197~198° C. |
| 36 | 3-(CN)C6H4-C≡C-CH2CH2-NH-thieno[2,3-d]pyrimidin-4-yl | m.p. 187~188° C. |

TABLE 1-7

| Compound No. | Structure | Physical property |
|---|---|---|
| 37 | 4-(CN)C6H4-C≡C-CH2CH2-NH-thieno[2,3-d]pyrimidin-4-yl | m.p. 173~174° C. |
| 38 | 2-(NO2)C6H4-C≡C-CH2CH2-NH-thieno[2,3-d]pyrimidin-4-yl | m.p. 162~163° C. |
| 39 | 3-(NO2)C6H4-C≡C-CH2CH2-NH-thieno[2,3-d]pyrimidin-4-yl | m.p. 171~172° C. |
| 40 | 4-(NO2)C6H4-C≡C-CH2CH2-NH-thieno[2,3-d]pyrimidin-4-yl | m.p. 184~185° C. |
| 41 | 2,4-F2C6H3-C≡C-CH2CH2-NH-thieno[2,3-d]pyrimidin-4-yl | m.p. 177~178° C. |
| 42 | 2,6-F2C6H3-C≡C-CH2CH2-NH-thieno[2,3-d]pyrimidin-4-yl | m.p. 179~181° C. |

TABLE 1-8

| Compound No. | Structure | Physical property |
|---|---|---|
| 43 | (thieno[2,3-d]pyrimidin-4-yl)NH-CH2CH2-C≡C-(3,4,5-trifluorophenyl) | m.p. 158~159° C. |
| 44 | (thieno[2,3-d]pyrimidin-4-yl)NH-CH2CH2-C≡C-(2-(hydroxymethyl)phenyl) | m.p. 131~132° C. |
| 45 | (thieno[2,3-d]pyrimidin-4-yl)NH-CH2CH2-C≡C-(2-(methoxymethyl)phenyl) | Resinoid product |
| 46 | (thieno[2,3-d]pyrimidin-4-yl)NH-CH2CH2-C≡C-(2-(ethoxymethyl)phenyl) | Oily product |
| 47 | (thieno[2,3-d]pyrimidin-4-yl)NH-CH2CH2-C≡C-(2-(fluoromethyl)phenyl) | Oily product |

TABLE 1-9

| Compound No. | Structure | Physical property |
|---|---|---|
| 48 | (thieno[3,2-d]pyrimidin-4-yl)NH-CH2CH2-C≡C-(2-formylphenyl) | m.p. 162~163° C. |
| 49 | (thieno[3,2-d]pyrimidin-4-yl)NH-CH2CH2-C≡C-(2-(methoxymethyl)phenyl) | Oily product |
| 50 | (7-methylthieno[3,2-d]pyrimidin-4-yl)NH-CH2CH2-C≡C-(2-(methoxymethyl)phenyl) | Oily product |
| 51 | (6-methylthieno[3,2-d]pyrimidin-4-yl)NH-CH2CH2-C≡C-(2-(methoxymethyl)phenyl) | Oily product |
| 52 | (thieno[2,3-d]pyrimidin-4-yl)NH-CH2CH2-C≡C-(furan-3-yl) | m.p. 117~118° C. |

TABLE 1-9-continued

| Compound No. | Structure | Physical property |
|---|---|---|
| 53 | (thiophen-2-yl connected via butynyl-NH to thieno[2,3-d]pyrimidin-4-yl) | m.p. 127~128° C. |

TABLE 1-10

| Compound No. | Structure | Physical property |
|---|---|---|
| 54 | (thiophen-3-yl connected via butynyl-NH to thieno[2,3-d]pyrimidin-4-yl) | m.p. 153~155° C. |
| 55 | (pyridin-2-yl connected via butynyl-NH to thieno[2,3-d]pyrimidin-4-yl) | m.p. 178~180° C. |
| 56 | (pyridin-3-yl connected via butynyl-NH to thieno[2,3-d]pyrimidin-4-yl) | m.p. 138~140° C. |
| 57 | (pyridin-4-yl connected via butynyl-NH to thieno[2,3-d]pyrimidin-4-yl) | m.p. 140~141° C. |

TABLE 1-10-continued

| Compound No. | Structure | Physical property |
|---|---|---|
| 58 | (pyrimidin-2-yl connected via butynyl-NH to thieno[2,3-d]pyrimidin-4-yl) | Resinoid product |
| 59 | (4,6-dimethylpyrimidin-2-yl connected via butynyl-NH to thieno[2,3-d]pyrimidin-4-yl) | m.p. 112~113° C. |

TABLE 1-11

| Compound No. | Structure | Physical property |
|---|---|---|
| 60 | (4,6-dimethoxypyrimidin-2-yl connected via butynyl-NH to thieno[2,3-d]pyrimidin-4-yl) | Resinoid product |
| 61 | (thiazol-5-yl connected via butynyl-NH to thieno[2,3-d]pyrimidin-4-yl) | m.p. 156~158° C. |
| 62 | (thiazol-2-yl connected via butynyl-NH to thieno[2,3-d]pyrimidin-4-yl) | m.p. 128~129° C. |

TABLE 1-11-continued

| Compound No. | Structure | Physical property |
|---|---|---|
| 63 | (thieno[2,3-d]pyrimidin-4-yl)-NH-CH2CH2-C≡C-(thiazol-4-yl) | m.p. 174° C. |
| 64 | (thieno[2,3-d]pyrimidin-4-yl)-NH-CH2CH2-C≡C-(4-bromothiazol-2-yl) | m.p. 90~92° C. |

TABLE 1-12

| Compound No. | Structure | Physical property |
|---|---|---|
| 65 | (thieno[2,3-d]pyrimidin-4-yl)-NH-CH2CH2-C≡C-(5-methylthiazol-4-yl) | m.p. 148~150° C. |
| 66 | (thieno[2,3-d]pyrimidin-4-yl)-NH-CH2CH2-C≡C-(2-methylthiazol-4-yl) | m.p. 160~161° C. |
| 67 | (thieno[2,3-d]pyrimidin-4-yl)-NH-CH2CH2-C≡C-(2-methoxythiazol-4-yl) | m.p. 152~153° C. |

TABLE 1-12-continued

| Compound No. | Structure | Physical property |
|---|---|---|
| 68 | (thieno[2,3-d]pyrimidin-4-yl)-NH-CH2CH2-C≡C-(2-fluoromethylthiazol-4-yl) | Resinoid product |
| 69 | (thieno[2,3-d]pyrimidin-4-yl)-NH-CH2CH2-C≡C-(2-formylthiazol-4-yl) | Resinoid product |

TABLE 1-13

| Compound No. | Structure | Physical property |
|---|---|---|
| 70 | (thieno[2,3-d]pyrimidin-4-yl)-NH-CH2CH2-C≡C-(2-hydroxymethylthiazol-4-yl) | m.p. 193° C. |
| 71 | (thieno[2,3-d]pyrimidin-4-yl)-NH-CH2CH2-C≡C-(2-(tert-butyldimethylsilyloxymethyl)thiazol-4-yl) | Resinoid product |
| 72 | (thieno[2,3-d]pyrimidin-4-yl)-NH-CH2CH2-C≡C-(2-methoxymethylthiazol-4-yl) | Resinoid product |

TABLE 1-13-continued

| Compound No. | Structure | Physical property |
|---|---|---|
| 73 | 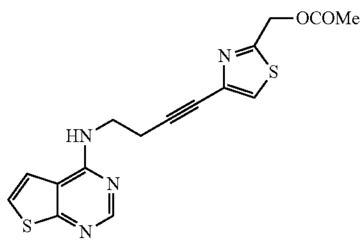 | m.p. 128~129° C. |
| 74 | 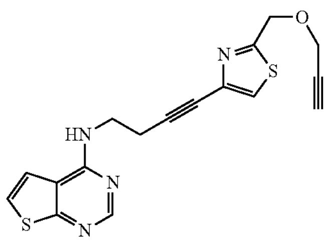 [SMILES: C#CCOCc1nc(C#CCCNc2ncnc3sccc23)cs1] | Oily product |

TABLE 1-14

| Compound No. | Structure | Physical property |
|---|---|---|
| 75 | 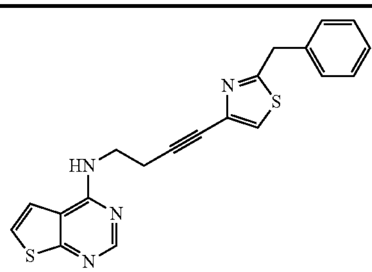 | Resinoid product |
| 76 | 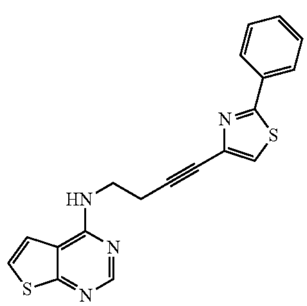 [SMILES: C(#Cc1csc(-c2ccccc2)n1)CCNc1ncnc2sccc12] | m.p. 134~136° C. |
| 77 | 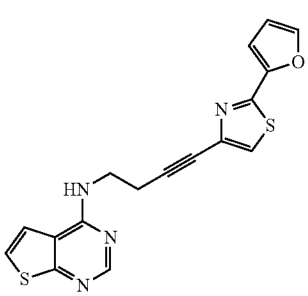 [SMILES: C(#Cc1csc(-c2ccco2)n1)CCNc1ncnc2sccc12] | m.p. 53~55° C. |

TABLE 1-14-continued

| Compound No. | Structure | Physical property |
|---|---|---|
| 78 | 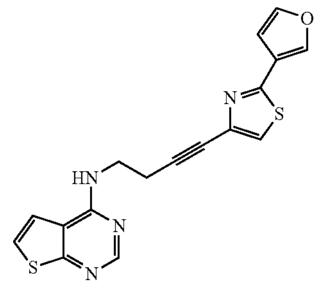 [SMILES: C(#Cc1csc(-c2ccoc2)n1)CCNc1ncnc2sccc12] | m.p. 140~142° C. |

TABLE 1-15

| Compound No. | Structure | Physical property |
|---|---|---|
| 79 | 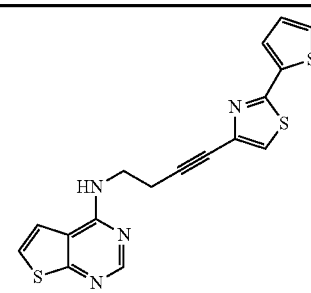 | Resinoid product |
| 80 | 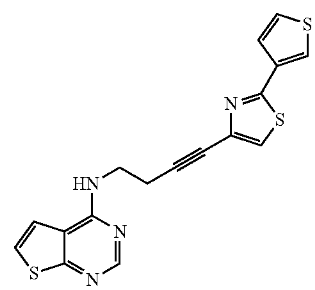 [SMILES: C(#Cc1csc(-c2ccsc2)n1)CCNc1ncnc2sccc12] | m.p. 55~56° C. |
| 81 | 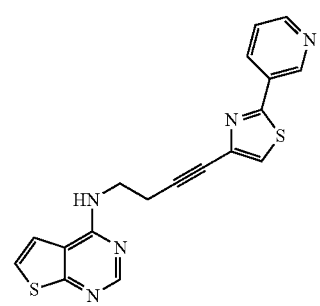 [SMILES: C(#Cc1csc(-c2cccnc2)n1)CCNc1ncnc2sccc12] | m.p. 175~177° C. |
| 82 | 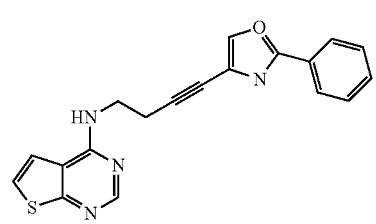 | m.p. 79~80° C. |

TABLE 1-15-continued

| Compound No. | Structure | Physical property |
|---|---|---|
| 83 | (thieno[2,3-d]pyrimidin-4-yl)-NH-CH2-C≡C-(thiazol-4-yl)-2-O-phenyl | Resinoid product |

TABLE 1-16

| Compound No. | Structure | Physical property |
|---|---|---|
| 84 | (thieno[2,3-d]pyrimidin-4-yl)-NH-CH2CH2-C≡C-(N-methylphthalimid-5-yl) | m.p. 193~195° C. |
| 85 | (thieno[2,3-d]pyrimidin-4-yl)-NH-CH2CH2-C≡C-(6-methoxybenzothiazol-2-yl) | Resinoid product |
| 86 | (quinazolin-4-yl)-NH-CH2CH2-C≡CH | m.p. 160~162° C. |
| 87 | (quinazolin-4-yl)-NH-CH2CH2-C≡C-Si(CH3)3 | m.p. 159~161° C. |
| 88 | (quinazolin-4-yl)-NH-CH2CH2-C≡C-n-C4H9 | m.p. 99~101° C. |

TABLE 1-16-continued

| Compound No. | Structure | Physical property |
|---|---|---|
| 89 | (quinazolin-4-yl)-NH-CH2CH2-C≡C-n-C6H13 | m.p. 82~84° C. |

TABLE 1-17

| Compound No. | Structure | Physical property |
|---|---|---|
| 90 | (quinazolin-4-yl)-NH-CH2CH2-C≡C-cyclopropyl | m.p. 107~109° C. |
| 91 | (quinazolin-4-yl)-NH-CH2CH2-C≡C-cyclohexyl | m.p. 155~157° C. |
| 92 | (quinazolin-4-yl)-NH-CH2CH2-C≡C-C(=CH2)-CH2OH | m.p. 139° C. |
| 93 | (quinazolin-4-yl)-NH-CH2CH2-C≡C-C(CH3)=CH-CN | m.p. 84~86° C. |
| 94 | (quinazolin-4-yl)-NH-CH2CH2-C≡C-(cyclohex-1-en-1-yl) | m.p. 160~162° C. |
| 95 | (quinazolin-4-yl)-NH-CH2CH2-C≡C-C(=CH2)-phenyl | Oily product |

TABLE 1-18

| Compound No. | Structure | Physical property |
|---|---|---|
| 96 | quinazolin-4-yl-NH-CH2CH2-C≡C-phenyl | m.p. 120~122° C. |
| 97 | quinazolin-4-yl-NH-CH2CH2-C≡C-(2-Cl-phenyl) | Resinoid product |
| 98 | quinazolin-4-yl-NH-CH2CH2-C≡C-(4-I-phenyl) | m.p. 183~184° C. |
| 99 | quinazolin-4-yl-NH-CH2CH2-C≡C-(2-CH2F-phenyl) | Oily product |
| 100 | quinazolin-4-yl-NH-CH2CH2-C≡C-(2-CHF2-phenyl) | Oily product |
| 101 | quinazolin-4-yl-NH-CH2CH2-C≡C-(2-CF3-phenyl) | m.p. 136~138° C. |

TABLE 1-19

| Compound No. | Structure | Physical property |
|---|---|---|
| 102 | quinazolin-4-yl-NH-CH2CH2-C≡C-(2-CN-phenyl) | m.p. 150~151° C. |
| 103 | quinazolin-4-yl-NH-CH2CH2-C≡C-(2-Et-phenyl) | m.p. 106~107° C. |
| 104 | quinazolin-4-yl-NH-CH2CH2-C≡C-(2-iPr-phenyl) | m.p. 90~91° C. |
| 105 | quinazolin-4-yl-NH-CH2CH2-C≡C-(2-(3-methylbut-3-enyl)-phenyl) | m.p. 92~94° C. |
| 106 | quinazolin-4-yl-NH-CH2CH2-C≡C-(4-n-C$_4$H$_9$-phenyl) | m.p. 102~105° C. |
| 107 | quinazolin-4-yl-NH-CH2CH2-C≡C-(4-n-C$_6$H$_{12}$-phenyl) | m.p. 100~102° C. |

TABLE 1-20

| Compound No. | Structure | Physical property |
|---|---|---|
| 108 | (quinazolin-4-yl)NH-CH2CH2-C≡C-C6H4-n-C8H17 | Resinoid product |
| 109 | (quinazolin-4-yl)NH-CH2CH2-C≡C-C6H4-cyclohexyl | m.p. 152~154° C. |
| 110 | (quinazolin-4-yl)NH-CH2CH2-C≡C-C6H4-CH=CH2 | Resinoid product |
| 111 | (quinazolin-4-yl)NH-CH2CH2-C≡C-C6H4-Si(CH3)3 | Resinoid product |
| 112 | (quinazolin-4-yl)NH-CH2CH2-C≡C-C6H4-C6H4-n-C7H15 | m.p. 144~146° C. |

TABLE 1-21

| Compound No. | Structure | Physical property |
|---|---|---|
| 113 | 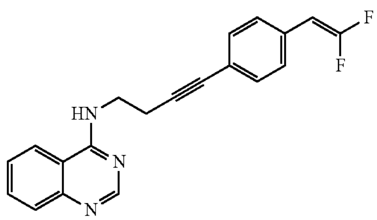 [SMILES: FC(F)=Cc1ccc(C#CCCNc2ncnc3ccccc23)cc1] | Oily product |
| 114 | 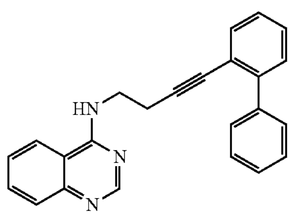 [SMILES: C(#Cc1ccccc1-c1ccccc1)CCNc1ncnc2ccccc12] | Oily product |
| 115 | 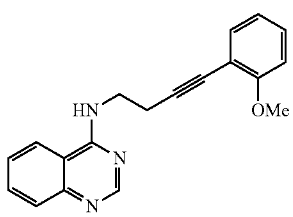 [SMILES: COc1ccccc1C#CCCNc1ncnc2ccccc12] | Oily product |
| 116 | 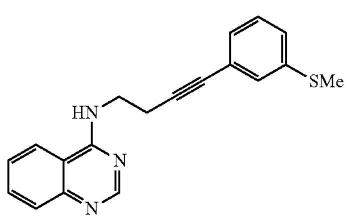 [SMILES: CSc1cccc(C#CCCNc2ncnc3ccccc23)c1] | m.p. 141~142° C. |
| 117 | 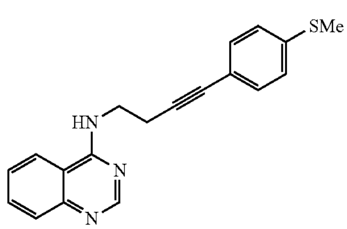 [SMILES: CSc1ccc(C#CCCNc2ncnc3ccccc23)cc1] | m.p. 147~148° C. |
| 118 | 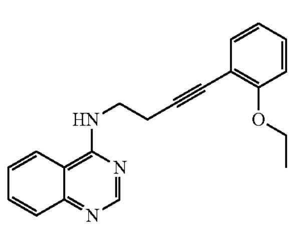 [SMILES: CCOc1ccccc1C#CCCNc1ncnc2ccccc12] | m.p. 119~120° C. |

TABLE 1-22

| Compound No. | Structure | Physical property |
|---|---|---|
| 119 | 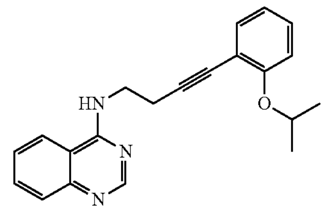 [SMILES: CC(C)Oc1ccccc1C#CCCNc1ncnc2ccccc12] | Resinoid product |
| 120 | 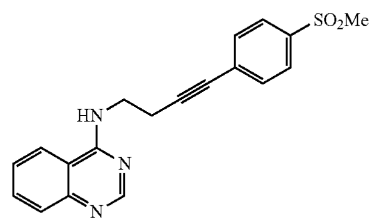 [SMILES: CS(=O)(=O)c1ccc(C#CCCNc2ncnc3ccccc23)cc1] | m.p. 164~165° C. |
| 121 | 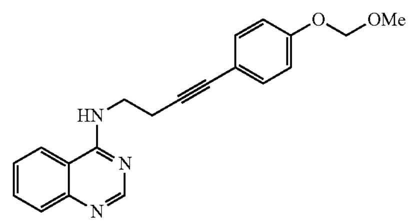 [SMILES: COCOc1ccc(C#CCCNc2ncnc3ccccc23)cc1] | m.p. 108~110° C. |
| 122 | 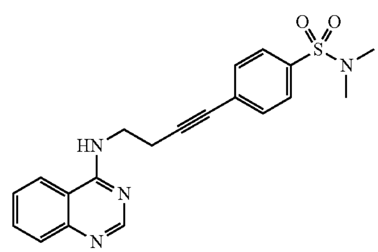 [SMILES: CN(C)S(=O)(=O)c1ccc(C#CCCNc2ncnc3ccccc23)cc1] | m.p. 175~176° C. |
| 123 | 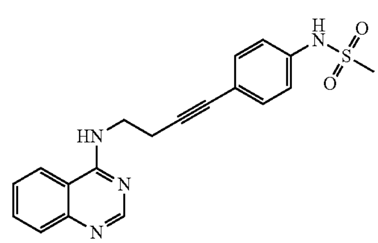 [SMILES: CS(=O)(=O)Nc1ccc(C#CCCNc2ncnc3ccccc23)cc1] | Oily product |

TABLE 1-23

| Compound No. | Structure | Physical property |
|---|---|---|
| 124 | 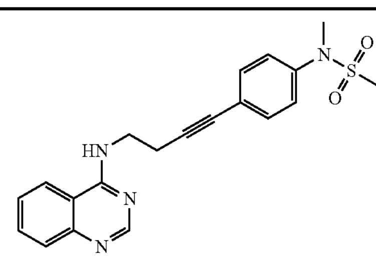 | Oily product |

TABLE 1-23-continued

| Compound No. | Structure | Physical property |
|---|---|---|
| 125 | quinazolin-4-yl-NH-CH2-C≡C-CH2- attached to 2-(N(OMe)C(O)OMe)phenyl | Resinoid product |
| 126 | quinazolin-4-yl-NH-CH2-C≡C-CH2- attached to 4-C(O)NHMe phenyl | m.p. 212~214° C. |
| 127 | quinazolin-4-yl-NH-CH2-C≡C-CH2- attached to 4-CO2H phenyl | Resinoid product |
| 128 | quinazolin-4-yl-NH-CH2-C≡C-CH2- attached to 4-COMe phenyl | Resinoid product |

TABLE 1-24

| No. | Structure | Physical property |
|---|---|---|
| 129 | quinazolin-4-yl-NH-CH2-C≡C-CH2- attached to 4-CO2C2H5 phenyl | m.p. 137~138° C. |
| 130 | quinazolin-4-yl-NH-CH2-C≡C-CH2- attached to 2-CH2OH phenyl | m.p. 156~157° C. |

TABLE 1-24-continued

| No. | Structure | Physical property |
|---|---|---|
| 131 | quinazolin-4-yl-NH-CH2-C≡C-CH2- attached to 3-CH2OH phenyl | m.p. 113~115° C. |
| 132 | quinazolin-4-yl-NH-CH2-C≡C-CH2- attached to 4-CH2OH phenyl | m.p. 69~71° C. |
| 133 | quinazolin-4-yl-NH-CH2-C≡C-CH2- attached to 2-CH2OMe phenyl | m.p. 108~110° C. |

TABLE 1-25

| Compound No. | Structure | Physical property |
|---|---|---|
| 134 | quinazolin-4-yl-NH-CH2-C≡C-CH2- attached to 2-CH2OCHF2 phenyl | Resinoid product |
| 135 | quinazolin-4-yl-NH-CH2-C≡C-CH2- attached to 3-CH2OMe phenyl | Resinoid product |
| 136 | quinazolin-4-yl-NH-CH2-C≡C-CH2- attached to 4-CH2OMe phenyl | m.p. 107~109° C. |

TABLE 1-25-continued
| Compound No. | Structure | Physical property |
|---|---|---|
| 137 | 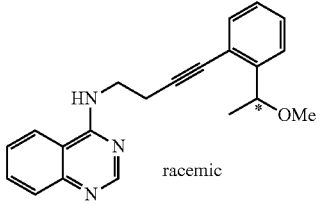 [SMILES: COC(C)c1ccccc1C#CCCNc1ncnc2ccccc12] racemic | Oily product |
| 138 | 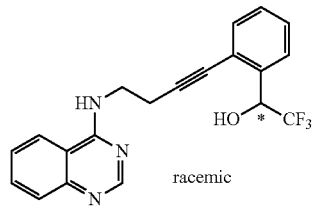 [SMILES: OC(c1ccccc1C#CCCNc1ncnc2ccccc12)C(F)(F)F] racemic | m.p. 183~187° C. |
TABLE 1-26
| Compound No. | Structure | Physical property |
|---|---|---|
| 139 | 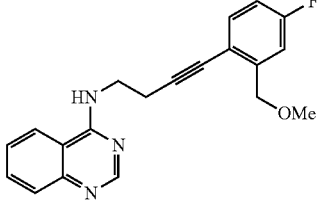 [SMILES: COCc1cc(C)ccc1C#CCCNc1ncnc2ccccc12] | m.p. 121~122° C. |
| 140 | 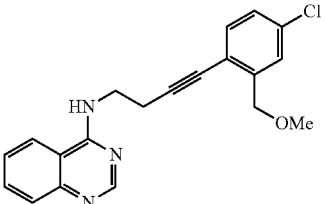 | m.p. 122~124° C. |
| 141 | 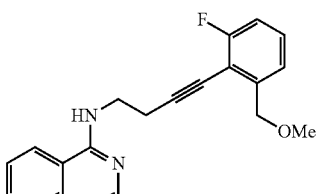 | Oily product |
| 142 | 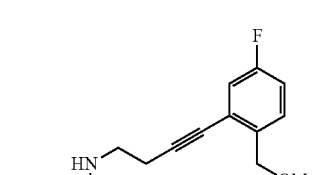 | m.p. 124~125° C. |
TABLE 1-26-continued
| Compound No. | Structure | Physical property |
|---|---|---|
| 143 | 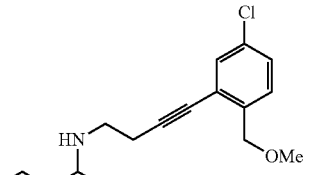 | Oily product |
TABLE 1-27
| Compound No. | Structure | Physical property |
|---|---|---|
| 144 | 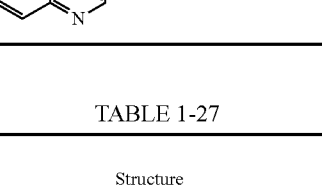 | Oily product |
| 145 | 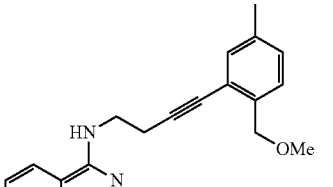 | m.p. 102~105° C. |
| 146 | 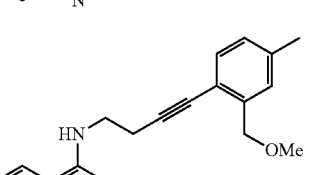 | m.p. 121~125° C. |
| 147 | 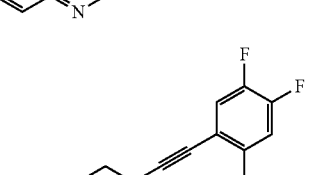 | m.p. 146~147° C. |
| 148 | 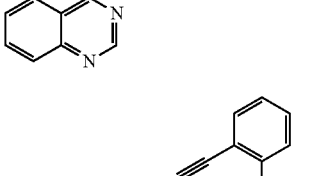 | Oily product |

TABLE 1-28

| Compound No. | Structure | Physical property |
|---|---|---|
| 149 | 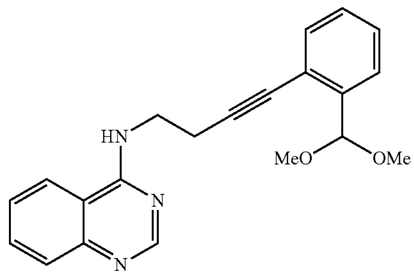 [SMILES: COC(OC)c1ccccc1C#CCCNc1ncnc2ccccc12] | Oily product |
| 150 | 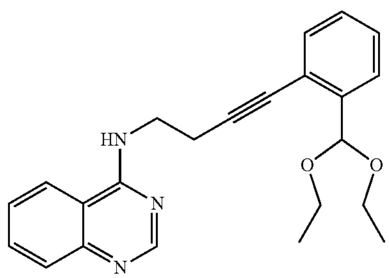 [SMILES: CCOC(OCC)c1ccccc1C#CCCNc1ncnc2ccccc12] | Oily product |
| 151 | 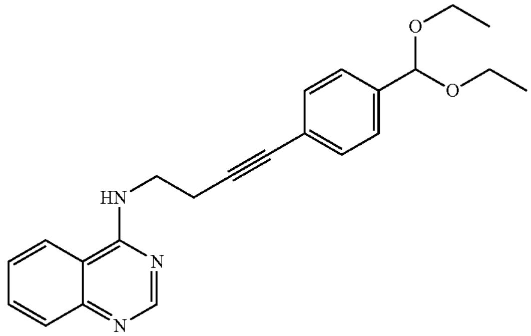 [SMILES: CCOC(OCC)c1ccc(C#CCCNc2ncnc3ccccc23)cc1] | m.p. 143~144° C. |
| 152 | 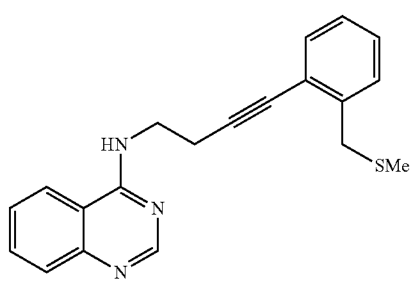 [SMILES: CSCc1ccccc1C#CCCNc1ncnc2ccccc12] | m.p. 131~133° C. |
| 153 | 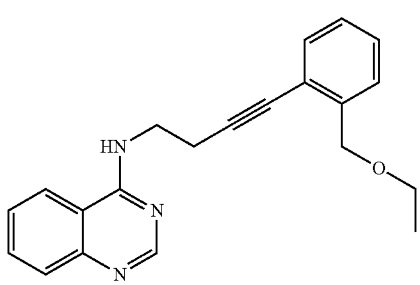 [SMILES: CCOCc1ccccc1C#CCCNc1ncnc2ccccc12] | Oily product |

TABLE 1-29

| Compound No. | Structure | Physical property |
| --- | --- | --- |
| 154 | 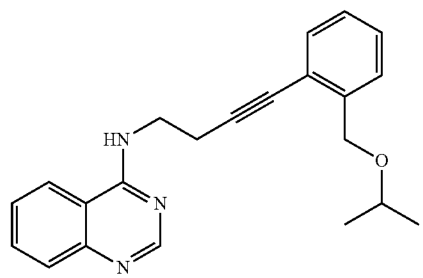 [SMILES: CC(C)OCc1ccccc1C#CCCNc1ncnc2ccccc12] | Resinoid product |
| 155 | 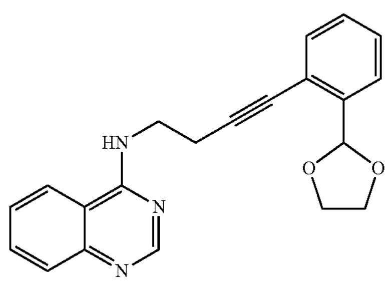 [SMILES: C(#Cc1ccccc1C1OCCO1)CCNc1ncnc2ccccc12] | Oily product |
| 156 | 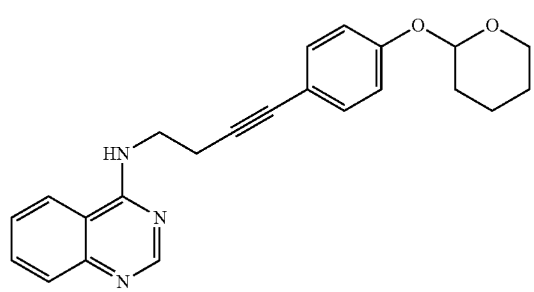 [SMILES: C(#Cc1ccc(OC2CCCCO2)cc1)CCNc1ncnc2ccccc12] | m.p. 163~165° C. |
| 157 | 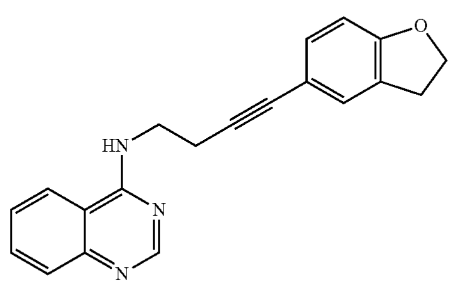 [SMILES: C(#Cc1ccc2c(c1)CCO2)CCNc1ncnc2ccccc12] | Resinoid product |
| 158 | 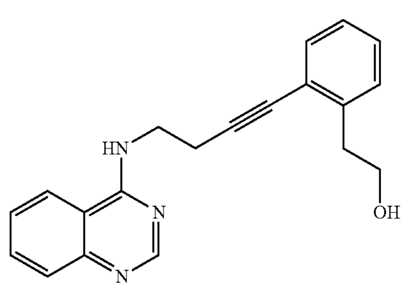 [SMILES: OCCc1ccccc1C#CCCNc1ncnc2ccccc12] | Resinoid product |

TABLE 1-30

| Compound No. | Structure | Physical property |
|---|---|---|
| 159 | quinazolin-4-yl-NH-CH2-CH2-C≡C-C6H4-N(CH3)2 (para) | Resinoid product |
| 160 | quinazolin-4-yl-NH-CH2-CH2-C≡C-C6H4-NHC(O)CH3 (ortho) | m.p. 177~178° C. |
| 161 | quinazolin-4-yl-NH-CH2-CH2-C≡C-C6H4-SO2N(CH3)2 (ortho) | m.p. 146~148° C. |
| 162 | quinazolin-4-yl-NH-CH2-CH2-C≡C-C6H4-CH2S(O)2CH3 (ortho) | Resinoid product |
| 163 | quinazolin-4-yl-NH-CH2-CH2-C≡C-C6H3-2,5-F2 | m.p. 176~177° C. |

TABLE 1-31

| Compound No. | Structure | Physical property |
|---|---|---|
| 164 | quinazolin-4-yl-NH-CH2-CH2-C≡C-C6H3(2-F)(4-Cl) | m.p. 198~199° C. |

TABLE 1-31-continued

| Compound No. | Structure | Physical property |
|---|---|---|
| 165 | quinazolin-4-yl-NH-CH2-CH2-C≡C-C6H3(CN)(F) | m.p. 163~164° C. |
| 166 | quinazolin-4-yl-NH-CH2-CH2-C≡C-C6H3-3,4-F2 | m.p. 161~162° C. |
| 167 | quinazolin-4-yl-NH-CH2-CH2-C≡C-C6H3(F)(CH3) | Resinoid product |
| 168 | quinazolin-4-yl-NH-CH2-CH2-C≡C-C6H3(F)(CF3) | m.p. 147~148° C. |

TABLE 1-32

| Compound No. | Structure | Physical property |
|---|---|---|
| 169 | quinazolin-4-yl-NH-CH2-CH2-C≡C-C6H3(F)(CF3) | m.p. 134~135° C. |
| 170 | quinazolin-4-yl-NH-CH2-CH2-C≡C-C6H3(F)(CN) | m.p. 142~143° C. |

TABLE 1-32-continued

| Compound No. | Structure | Physical property |
|---|---|---|
| 171 | (quinazolin-4-yl)NH-CH2-C≡C-(2,3-dichlorophenyl) | m.p. 175~176° C. |
| 172 | (quinazolin-4-yl)NH-CH2-C≡C-(2,4-dichlorophenyl) | m.p. 182~183° C. |
| 173 | (quinazolin-4-yl)NH-CH2CH2-C≡C-(2,5-dichlorophenyl) | m.p. 176~177° C. |

TABLE 1-33

| Compound No. | Structure | Physical property |
|---|---|---|
| 174 | (quinazolin-4-yl)NH-CH2-C≡C-(2,6-dichlorophenyl) | m.p. 153~155° C. |
| 175 | (quinazolin-4-yl)NH-CH2CH2-C≡C-(3,4-dichlorophenyl) | m.p. 147~148° C. |
| 176 | (quinazolin-4-yl)NH-CH2CH2-C≡C-(2-chloro-5-trifluoromethylphenyl) | m.p. 144~145° C. |
| 177 | (quinazolin-4-yl)NH-CH2-C≡C-(3-chloro-4-trifluoromethylphenyl) | m.p. 139~140° C. |
| 178 | (quinazolin-4-yl)NH-CH2-C≡C-(4-chloro-2-trifluoromethylphenyl) | m.p. 161~163° C. |

TABLE 1-34

| Compound No. | Structure | Physical property |
|---|---|---|
| 179 | (quinazolin-4-yl)NH-CH2CH2-C≡C-(5-chloro-2-methoxyphenyl) | m.p. 147~149° C. |

TABLE 1-34-continued

| Compound No. | Structure | Physical property |
|---|---|---|
| 180 | (quinazolin-4-yl)NH-CH₂CH₂-C≡C-(2,4-dimethylphenyl) | m.p. 153~155° C. |
| 181 | (quinazolin-4-yl)NH-CH₂CH₂-C≡C-(2,4,6-trimethylphenyl) | Oily product |
| 182 | (quinazolin-4-yl)NH-CH₂CH₂-C≡C-(2-chloro-4-trifluoromethylphenyl) | m.p. 135~139° C. |
| 183 | (quinazolin-4-yl)NH-CH₂CH₂-C≡C-(naphthalen-2-yl) | m.p. 159~160° C. |
| 184 | (quinazolin-4-yl)NH-CH₂CH₂-C≡C-(6-methoxynaphthalen-2-yl) | m.p. 191~192° C. |

TABLE 1-35

| Compound No. | Structure | Physical property |
|---|---|---|
| 185 | 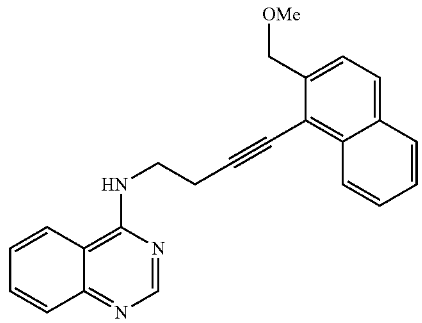 [SMILES: COCc1ccc2ccccc2c1C#CCCNc1ncnc2ccccc12] | Oily product |
| 186 | 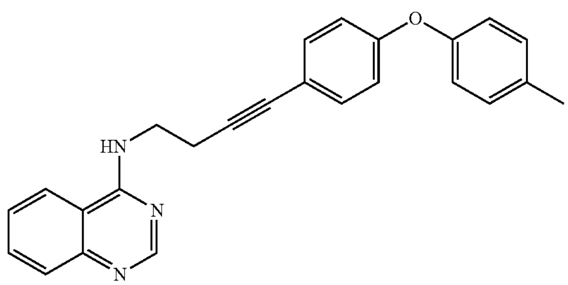 [SMILES: Cc1ccc(Oc2ccc(C#CCCNc3ncnc4ccccc34)cc2)cc1] | Oily product |
| 187 | 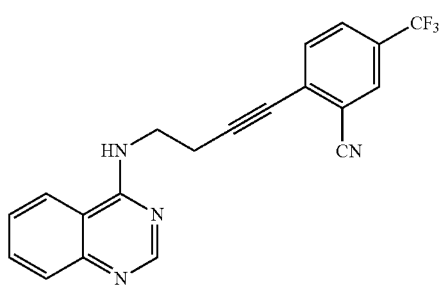 [SMILES: N#Cc1cc(C(F)(F)F)ccc1C#CCCNc1ncnc2ccccc12] | m.p. 181~182° C. |
| 188 | 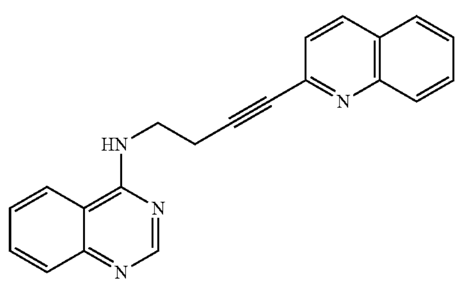 | Resinoid product |
| 189 | 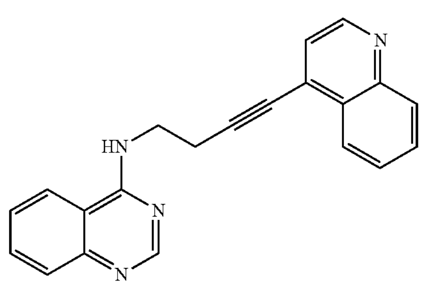 [SMILES: C(#Cc1ccnc2ccccc12)CCNc1ncnc2ccccc12] | Resinoid product |

TABLE 1-35-continued

| Compound No. | Structure | Physical property |
|---|---|---|
| 190 | 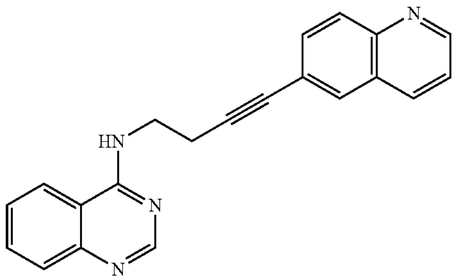 [SMILES: C(#Cc1ccc2ncccc2c1)CCNc1ncnc2ccccc12] | m.p. 183~186° C. |

TABLE 1-36

| Compound No. | Structure | Physical property |
|---|---|---|
| 191 | 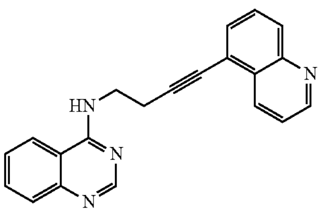 [SMILES: C(#Cc1cccc2ncccc12)CCNc1ncnc2ccccc12] | Resinoid product |
| 192 | 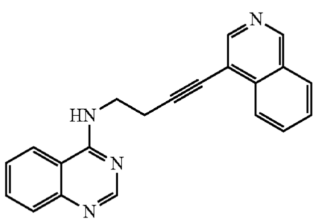 [SMILES: C(#Cc1cncc2ccccc12)CCNc1ncnc2ccccc12] | Resinoid product |
| 193 | 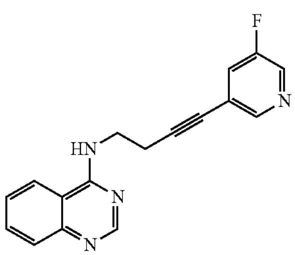 [SMILES: Fc1cncc(C#CCCNc2ncnc3ccccc23)c1] | m.p. 145~150° C. |
| 194 | 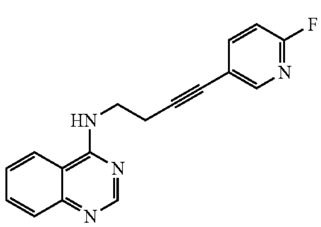 [SMILES: Fc1ccc(C#CCCNc2ncnc3ccccc23)cn1] | m.p. 157~158° C. |
| 195 | 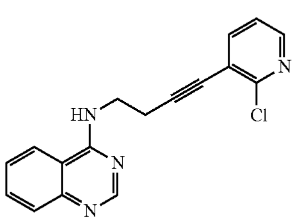 [SMILES: Clc1ncccc1C#CCCNc1ncnc2ccccc12] | m.p. 168~170° C. |

TABLE 1-37

| Compound No. | Structure | Physical property |
|---|---|---|
| 196 | 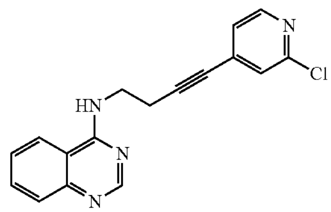 [SMILES: Clc1cc(C#CCCNc2ncnc3ccccc23)ccn1] | Resinoid product |
| 197 | 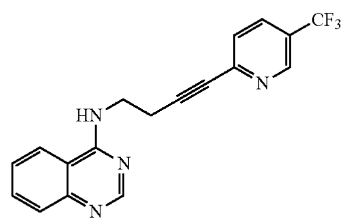 [SMILES: FC(F)(F)c1ccc(C#CCCNc2ncnc3ccccc23)nc1] | Resinoid product |
| 198 | 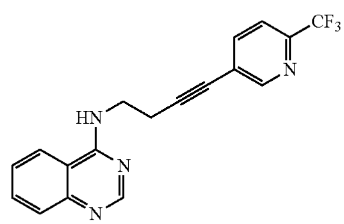 [SMILES: FC(F)(F)c1ccc(C#CCCNc2ncnc3ccccc23)cn1] | m.p. 134~139° C. |
| 199 | 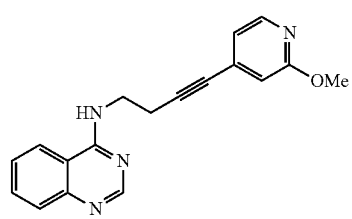 [SMILES: COc1cc(C#CCCNc2ncnc3ccccc23)ccn1] | m.p. 161~163° C. |
| 200 | 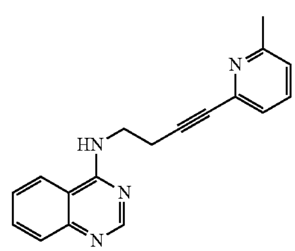 [SMILES: Cc1cccc(C#CCCNc2ncnc3ccccc23)n1] | Resinoid product |

TABLE 1-37-continued

| Compound No. | Structure | Physical property |
|---|---|---|
| 201 | 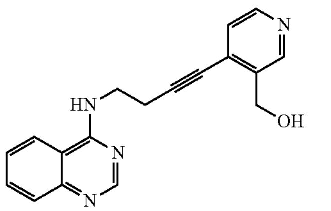 | m.p. 182~186° C. |

TABLE 1-38

| Compound No. | Structure | Physical property |
|---|---|---|
| 202 | 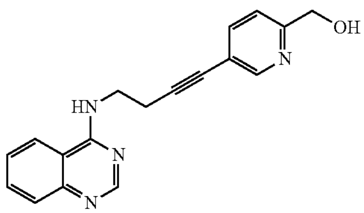 [SMILES: OCc1ccc(C#CCCNc2ncnc3ccccc23)cn1] | m.p. 183~185° C. |
| 203 | 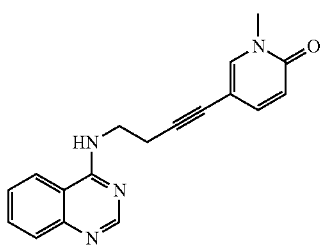 [SMILES: Cn1cc(C#CCCNc2ncnc3ccccc23)ccc1=O] | Oily product |
| 204 | 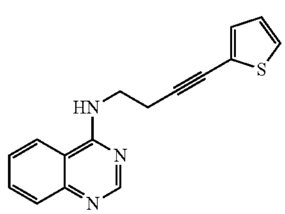 [SMILES: C(#Cc1cccs1)CCNc1ncnc2ccccc12] | m.p. 160~161° C. |
| 205 | 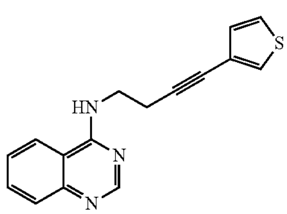 [SMILES: C(#Cc1ccsc1)CCNc1ncnc2ccccc12] | m.p. 180~181° C. |
| 206 | 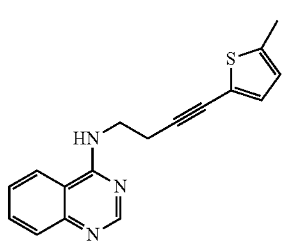 [SMILES: Cc1ccc(C#CCCNc2ncnc3ccccc23)s1] | m.p. 141~142° C. |

TABLE 1-38-continued

| Compound No. | Structure | Physical property |
|---|---|---|
| 207 | 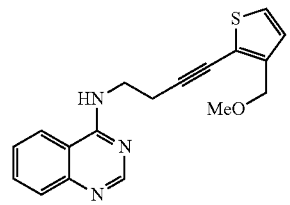 [SMILES: COCc1ccsc1C#CCCNc1ncnc2ccccc12] | Resinoid product |

TABLE 1-39

| Compound No. | Structure | Physical property |
|---|---|---|
| 208 | 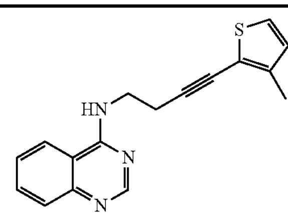 | m.p. 141~143° C. |
| 209 | 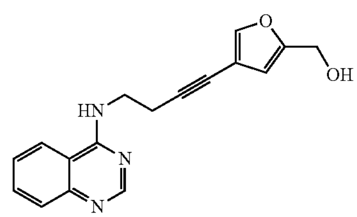 [SMILES: OCc1cc(C#CCCNc2ncnc3ccccc23)co1] | m.p. 135~147° C. |
| 210 | 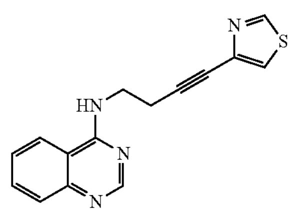 [SMILES: C(#Cc1cscn1)CCNc1ncnc2ccccc12] | m.p. 204~207° C. |
| 211 | 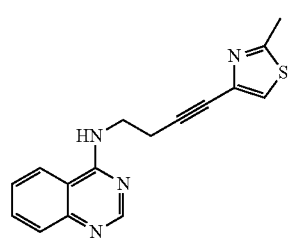 [SMILES: Cc1nc(C#CCCNc2ncnc3ccccc23)cs1] | m.p. 159~160° C. |
| 212 | 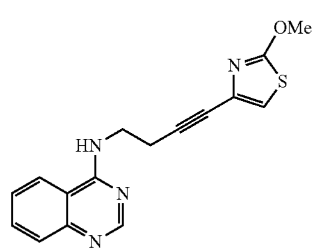 [SMILES: COc1nc(C#CCCNc2ncnc3ccccc23)cs1] | m.p. 145~146° C. |

TABLE 1-40

| Compound No. | Structure | Physical property |
|---|---|---|
| 213 | 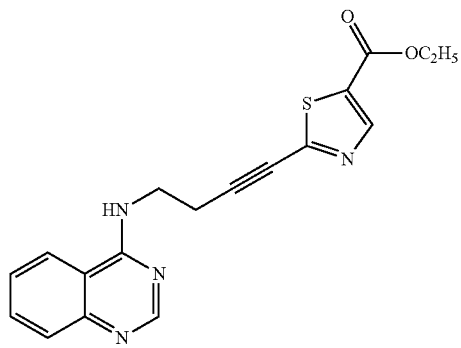 [SMILES: CCOC(=O)c1cnc(C#CCCNc2ncnc3ccccc23)s1] | m.p. 113~114° C. |
| 214 | 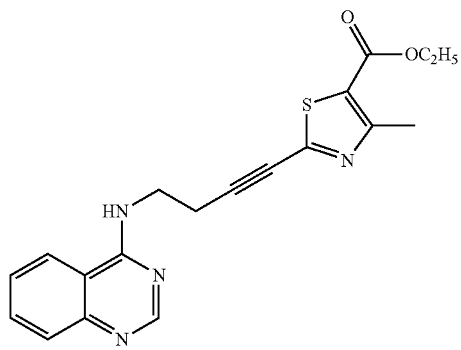 [SMILES: CCOC(=O)c1sc(C#CCCNc2ncnc3ccccc23)nc1C] | m.p. 139~140° C. |
| 215 | 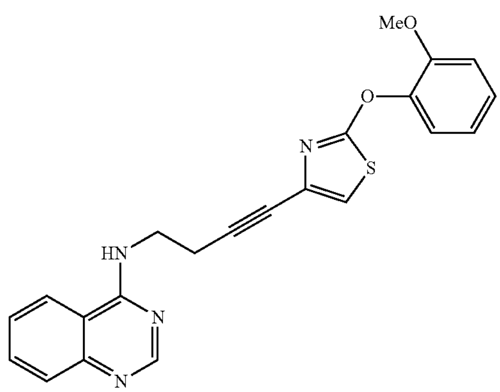 [SMILES: COc1ccccc1Oc1nc(C#CCCNc2ncnc3ccccc23)cs1] | Resinoid product |
| 216 | 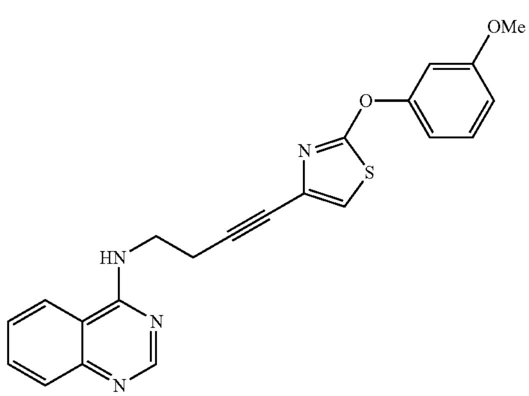 [SMILES: COc1cccc(Oc2nc(C#CCCNc3ncnc4ccccc34)cs2)c1] | m.p. 77~79° C. |

TABLE 1-40-continued
| Compound No. | Structure | Physical property |
|---|---|---|
| 217 | 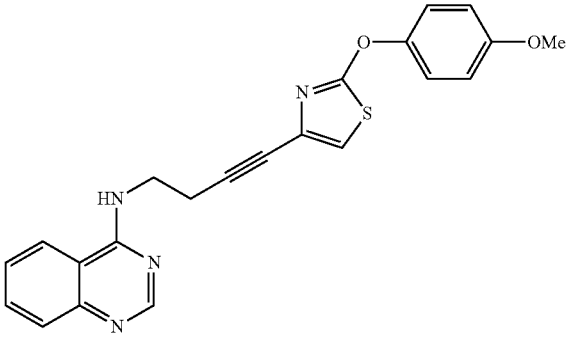 [SMILES: COc1ccc(Oc2nc(C#CCCNc3ncnc4ccccc34)cs2)cc1] | m.p. 150~152° C. |
TABLE 1-41
| Compound No. | Structure | Physical property |
|---|---|---|
| 218 | 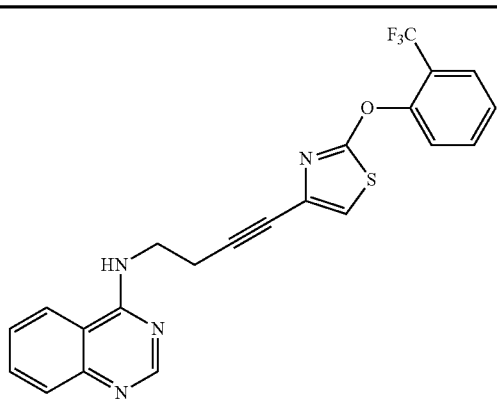 | m.p. 159~161° C. |
| 219 | 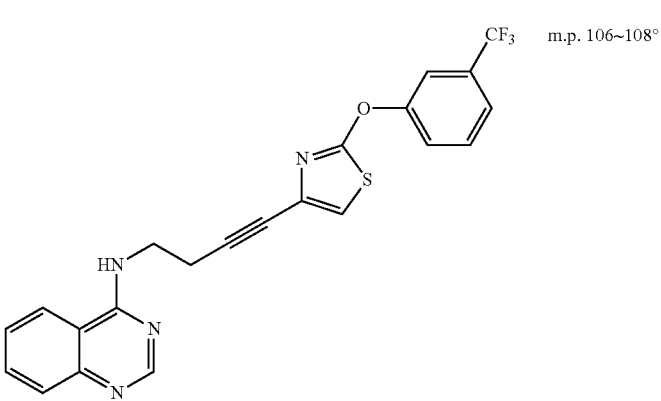 | m.p. 106~108° C. |

TABLE 1-41-continued

| Compound No. | Structure | Physical property |
|---|---|---|
| 220 | 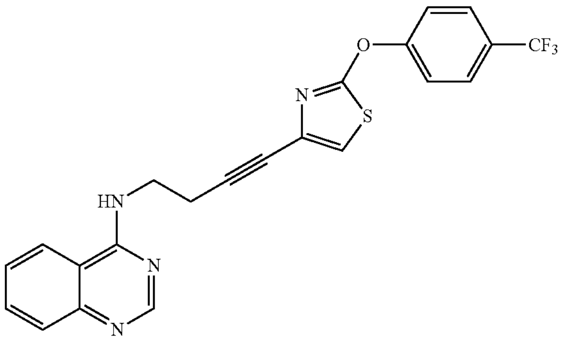 [SMILES: FC(F)(F)c1ccc(Oc2nc(C#CCCNc3ncnc4ccccc34)cs2)cc1] | m.p. 137~139° C. |
| 221 | 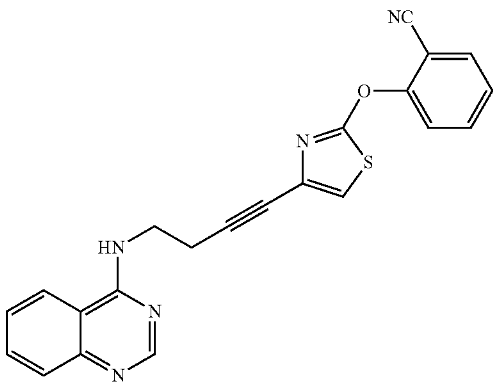 [SMILES: N#Cc1ccccc1Oc1nc(C#CCCNc2ncnc3ccccc23)cs1] | m.p. 185~186° C. |
| 222 | 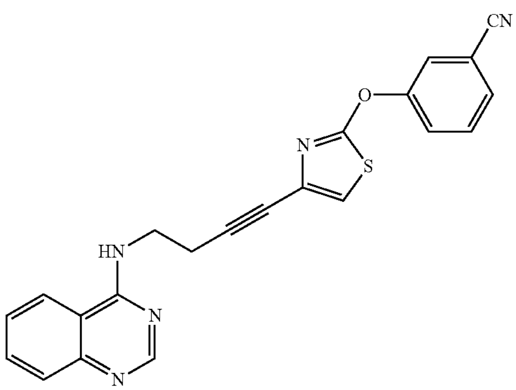 [SMILES: N#Cc1cccc(Oc2nc(C#CCCNc3ncnc4ccccc34)cs2)c1] | m.p. 137~139° C. |

TABLE 1-42

| Compound No. | Structure | Physical property |
|---|---|---|
| 223 | 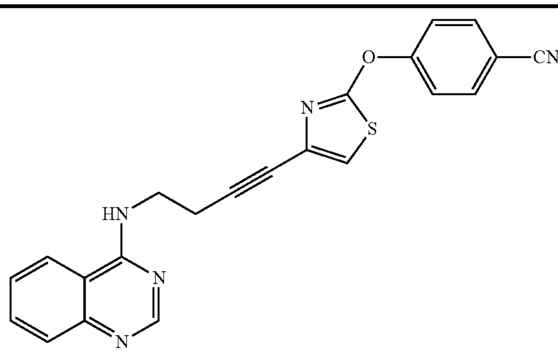 | m.p. 55~57° C. |

TABLE 1-42-continued
| Compound No. | Structure | Physical property |
|---|---|---|
| 224 | 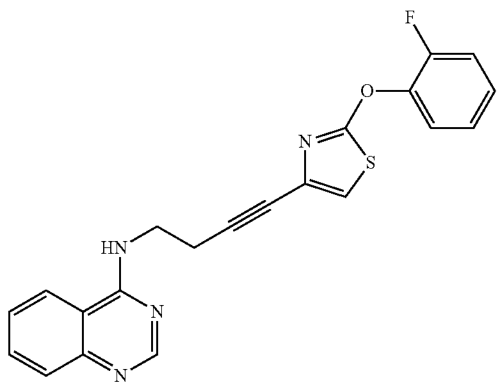 [SMILES: Fc1ccccc1Oc1nc(C#CCCNc2ncnc3ccccc23)cs1] | m.p. 136~138° C. |
| 225 | 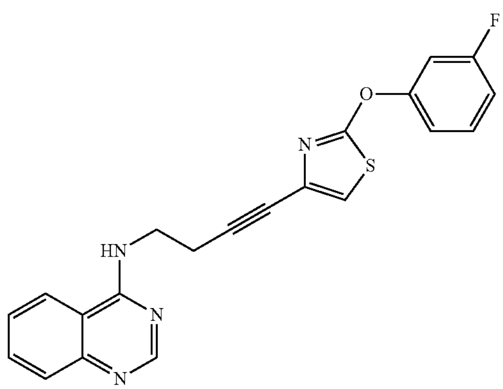 [SMILES: Fc1cccc(Oc2nc(C#CCCNc3ncnc4ccccc34)cs2)c1] | m.p. 134~136° C. |
| 226 | 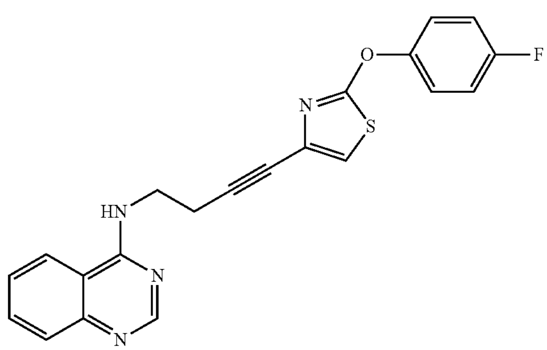 [SMILES: Fc1ccc(Oc2nc(C#CCCNc3ncnc4ccccc34)cs2)cc1] | m.p. 116~118° C. |
| 227 | 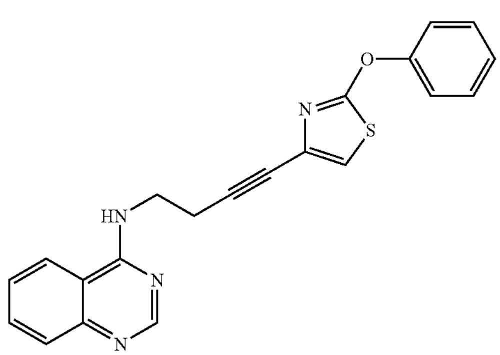 [SMILES: C(#Cc1csc(Oc2ccccc2)n1)CCNc1ncnc2ccccc12] | Resinoid product |

TABLE 1-43

| Compound No. | Structure | Physical property |
|---|---|---|
| 228 | *[thiazole-piperidine alkyne linked to quinazoline-NH]* | Oily product |
| 229 | *[phenyl alkyne-CH(CH3)-NH-thieno[2,3-d]pyrimidine]*, racemic | Resinoid product |
| 230 | *[4-fluorophenyl alkyne-CH(CH3)-NH-thieno[2,3-d]pyrimidine]*, racemic | m.p. 126~128° C. |
| 231 | *[2-chlorophenyl alkyne-CH(CH3)-NH-thieno[2,3-d]pyrimidine]*, racemic | Oily product |

TABLE 1-43-continued

| Compound No. | Structure | Physical property |
|---|---|---|
| 232 | *[4-chlorophenyl alkyne-CH(CH3)-NH-thieno[2,3-d]pyrimidine]*, racemic | m.p. 110~115° C. |

TABLE 1-44

| Compound No. | Structure | Physical property |
|---|---|---|
| 233 | *[2-CF3-phenyl alkyne-CH(CH3)-NH-thieno[2,3-d]pyrimidine]*, racemic | Oily product |
| 234 | *[3-CF3-phenyl alkyne-CH(CH3)-NH-thieno[2,3-d]pyrimidine]*, racemic | Oily product |

TABLE 1-44-continued
| Compound No. | Structure | Physical property |
|---|---|---|
| 235 | 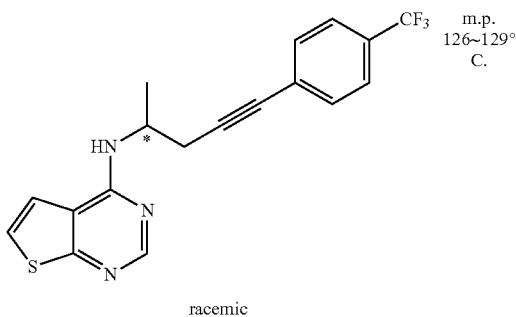 racemic | m.p. 126~129° C. |
| 236 | 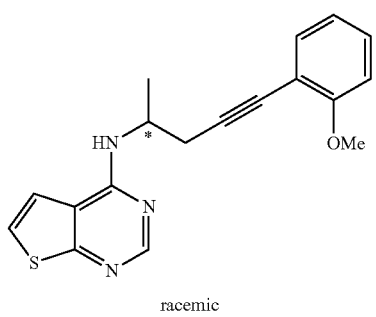 racemic | Resinoid product |
| 237 | 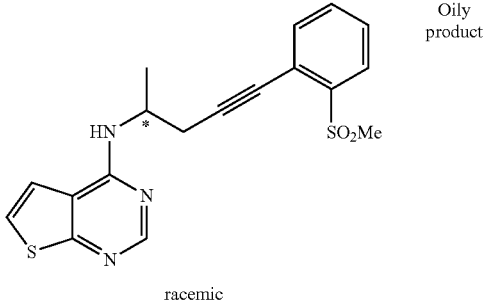 racemic | Oily product |
| 238 | 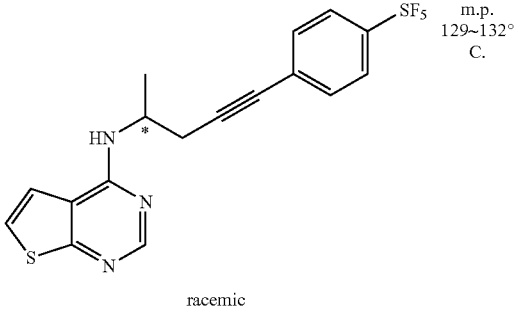 racemic | m.p. 129~132° C. |
TABLE 1-45
| Compound No. | Structure | Physical property |
|---|---|---|
| 239 | 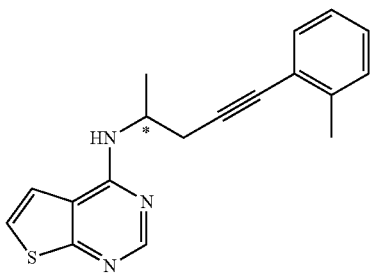 racemic | Oily product |
| 240 | 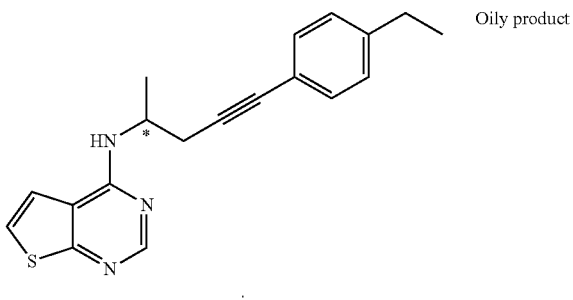 racemic | Oily product |

TABLE 1-45-continued

| Compound No. | Structure | Physical property |
| --- | --- | --- |
| 241 | (thieno[2,3-d]pyrimidin-4-yl)NH-CH(CH₃)-C≡C-(4-isopropylphenyl), racemic | Oily product |
| 242 | (thieno[2,3-d]pyrimidin-4-yl)NH-CH(CH₃)-C≡C-(2-isopropoxyphenyl), racemic | Oily product |
| 243 | (thieno[2,3-d]pyrimidin-4-yl)NH-CH(CH₃)-C≡C-(2-(hydroxymethyl)phenyl), racemic | m.p. 141~142° C. |
| 244 | (thieno[2,3-d]pyrimidin-4-yl)NH-CH(CH₃)-C≡C-(4-fluoro-2-(hydroxymethyl)phenyl), racemic | m.p. 138~139° C. |

TABLE 1-46

| Compound No. | Structure | Physical property |
|---|---|---|
| 245 | (thieno[2,3-d]pyrimidin-4-yl-NH-CH(CH3)-C≡C-phenyl with 5-Cl, 2-CH2OH); racemic | m.p. 125~126° C. |
| 246 | (thieno[2,3-d]pyrimidin-4-yl-NH-CH(CH3)-C≡C-phenyl with 4-F, 2-CH3); racemic | Resinoid product |
| 247 | (thieno[2,3-d]pyrimidin-4-yl-NH-CH(CH3)-C≡C-phenyl with 4-F, 2-Cl); racemic | Resinoid product |
| 248 | (thieno[2,3-d]pyrimidin-4-yl-NH-CH(CH3)-C≡C-phenyl with 5-F, 2-CF3); racemic | m.p. 118~120° C. |

TABLE 1-46-continued

| Compound No. | Structure | Physical property |
|---|---|---|
| 249 | (thieno[2,3-d]pyrimidin-4-yl-NH-CH(CH3)-C≡C-phenyl with 4-F, 2-CF3); racemic | Oily product |

TABLE 1-47

| Compound No. | Structure | Physical property |
|---|---|---|
| 250 | (thieno[2,3-d]pyrimidin-4-yl-NH-CH(CH3)-C≡C-phenyl with 4-Cl, 2-CH3); racemic | Oily product |
| 251 | (thieno[2,3-d]pyrimidin-4-yl-NH-CH(CH3)-C≡C-phenyl with 2,6-di-Cl); racemic | Oily product |

TABLE 1-47-continued
| Compound No. | Structure | Physical property |
|---|---|---|
| 252 | 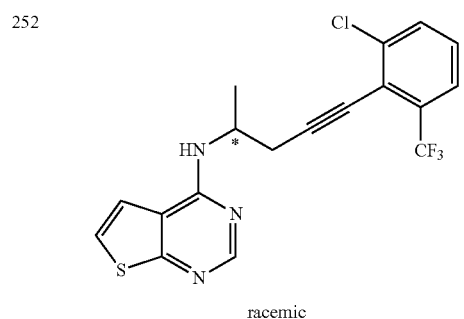 racemic | Resinoid product |
| 253 | 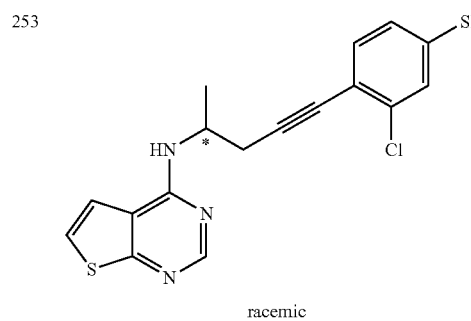 racemic | Oily product |
| 254 | 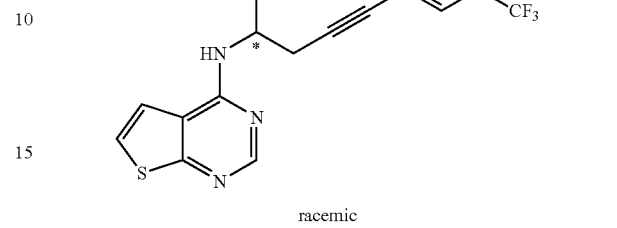 racemic | Resinoid product |
| 255 | 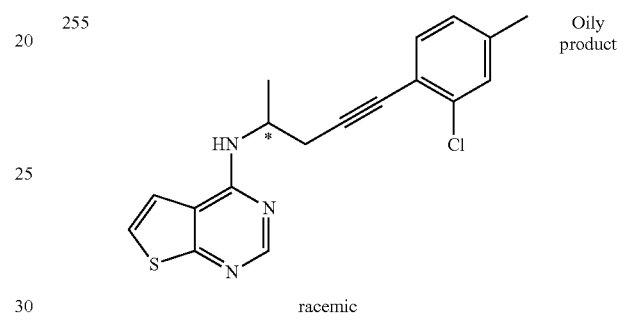 racemic | Oily product |
TABLE 1-48
| Compound No. | Structure | Physical property |
|---|---|---|
| 256 | 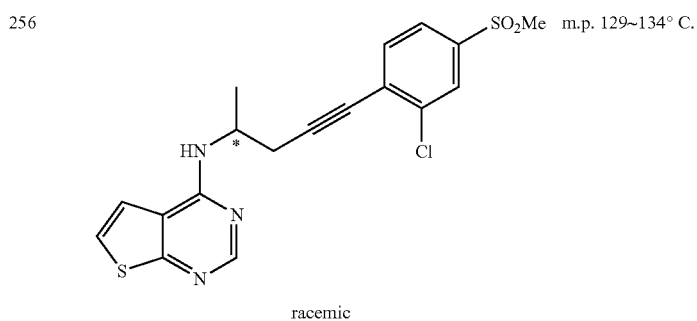 racemic | m.p. 129~134° C. |
| 257 | 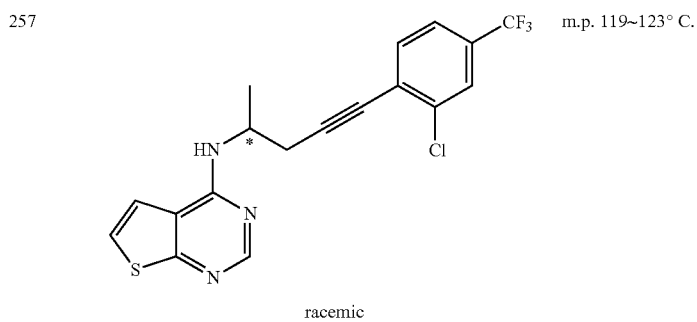 racemic | m.p. 119~123° C. |

TABLE 1-48-continued
| Compound No. | Structure | Physical property |
|---|---|---|
| 258 | 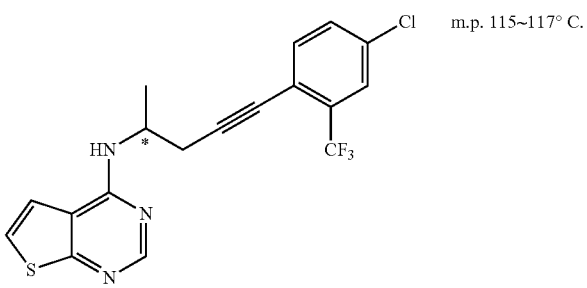 racemic | m.p. 115~117° C. |
| 259 | 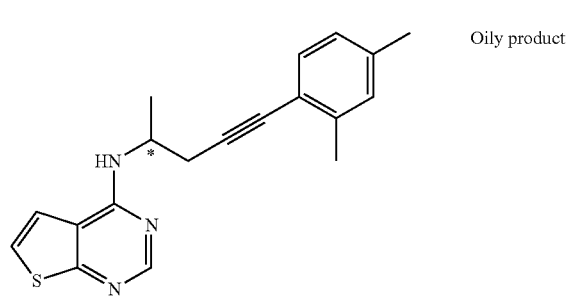 racemic | Oily product |
| 260 | 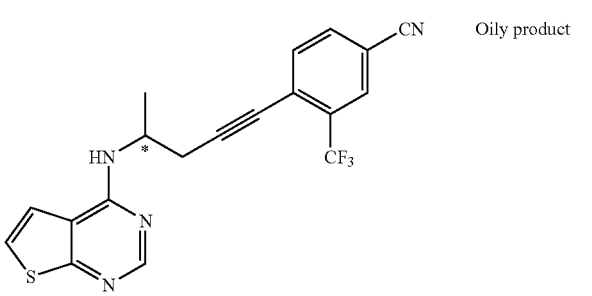 racemic | Oily product |
| 261 | 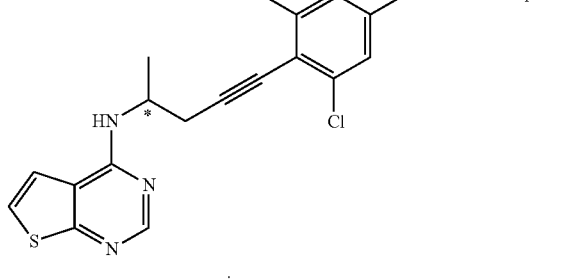 racemic | Resinoid product |

TABLE 1-49
| Compound No. | Structure | Physical property |
|---|---|---|
| 262 | 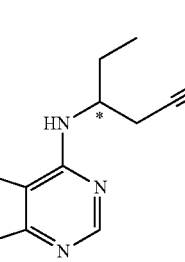 racemic | Oily product |
| 263 | racemic | Oily product |
| 264 | racemic | Oily product |
| 265 | racemic | Resinoid product |
| 266 | racemic | Resinoid product |
TABLE 1-49-continued
| Compound No. | Structure | Physical property |
|---|---|---|
| 267 | 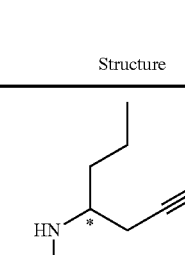 racemic | Oily product |
TABLE 1-50
| Compound No. | Structure | Physical property |
|---|---|---|
| 268 | 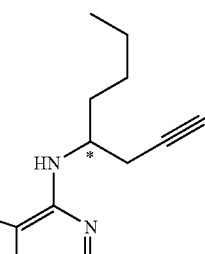 racemic | Oily product |
| 269 | racemic | Oily product |
| 270 | 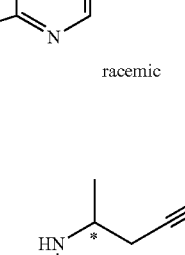 racemic | m.p. 158~160° C. |

TABLE 1-50-continued

| Compound No. | Structure | Physical property |
|---|---|---|
| 271 | 4-F-C6H4-C≡C-CH2-CH(CH3)-NH-quinazolin-4-yl (racemic) | m.p. 154~157° C. |
| 272 | 2-Cl-C6H4-C≡C-CH2-CH(CH3)-NH-quinazolin-4-yl (racemic) | m.p. 158~159° C. |
| 273 | 4-Cl-C6H4-C≡C-CH2-CH(CH3)-NH-quinazolin-4-yl (racemic) | Resinoid product |

TABLE 1-51

| Compound No. | Structure | Physical property |
|---|---|---|
| 274 | 2-CF3-C6H4-C≡C-CH2-CH(CH3)-NH-quinazolin-4-yl (racemic) | Resinoid product |

TABLE 1-51-continued

| Compound No. | Structure | Physical property |
|---|---|---|
| 275 | 4-CF3-C6H4-C≡C-CH2-CH(CH3)-NH-quinazolin-4-yl (racemic) | m.p. 138~141° C. |
| 276 | 2-OMe-C6H4-C≡C-CH2-CH(CH3)-NH-quinazolin-4-yl (racemic) | Oily product |
| 277 | 4-SF5-C6H4-C≡C-CH2-CH(CH3)-NH-quinazolin-4-yl (racemic) | Oily product |

TABLE 1-51-continued
| Compound No. | Structure | Physical property |
|---|---|---|
| 278 | (racemic) | Oily product |
| 279 | (racemic) | m.p. 164~166° C. |
TABLE 1-52
| Compound No. | Structure | Physical property |
|---|---|---|
| 280 | 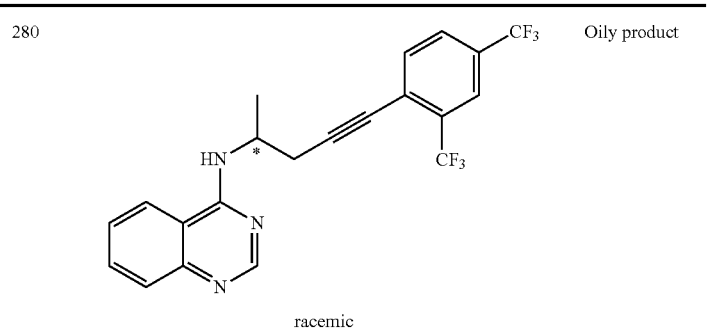 (racemic) | Oily product |
| 281 | 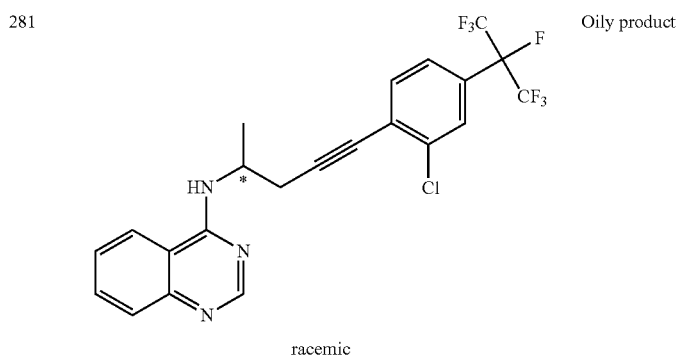 (racemic) | Oily product |
| 282 | 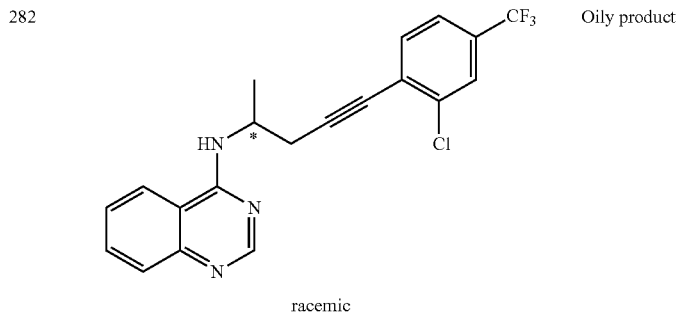 (racemic) | Oily product |

TABLE 1-52-continued
| Compound No. | Structure | Physical property |
|---|---|---|
| 283 | 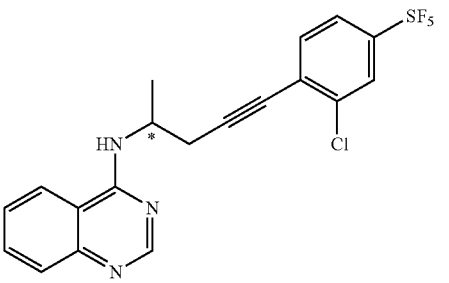 racemic | Oily product |
| 284 | 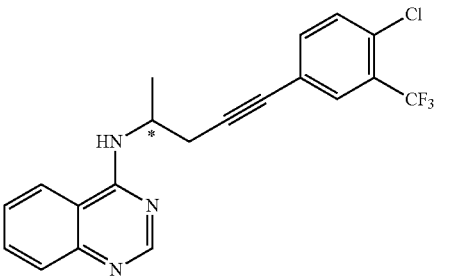 racemic | Resinoid product |
TABLE 1-53
| Compound No. | Structure | Physical property |
|---|---|---|
| 285 | 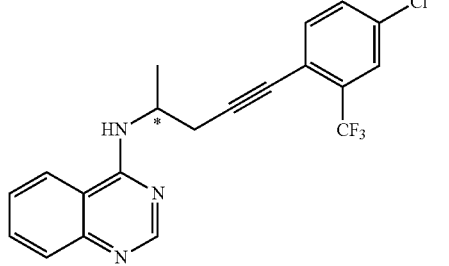 racemic | m.p. 130~131° C. |
| 286 | 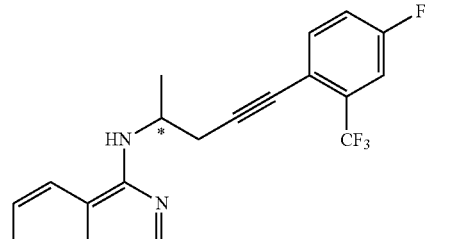 racemic | m.p. 104~105° C. |

TABLE 1-53-continued
| Compound No. | Structure | Physical property |
|---|---|---|
| 287 | 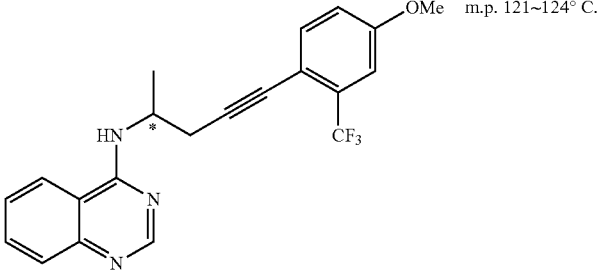 racemic | m.p. 121~124° C. |
| 288 | 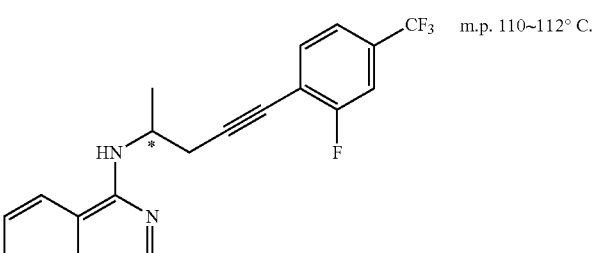 racemic | m.p. 110~112° C. |
| 289 | 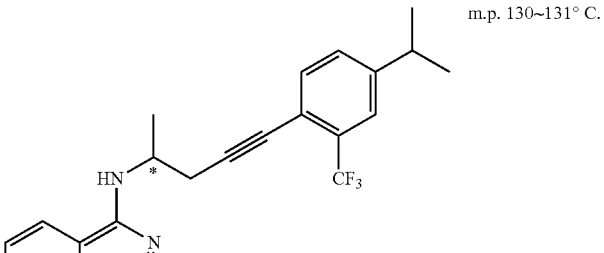 racemic | m.p. 130~131° C. |
TABLE 1-54
| Compound No. | Structure | Physical property |
|---|---|---|
| 290 | 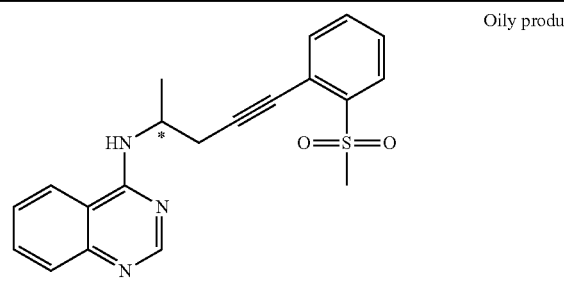 racemic | Oily product |

TABLE 1-54-continued
| Compound No. | Structure | Physical property |
|---|---|---|
| 291 | 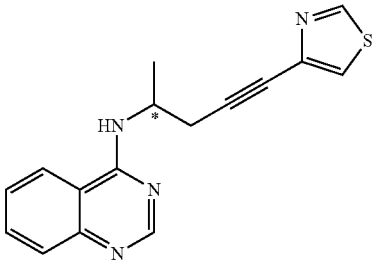 racemic | m.p. 142~145° C. |
| 292 | 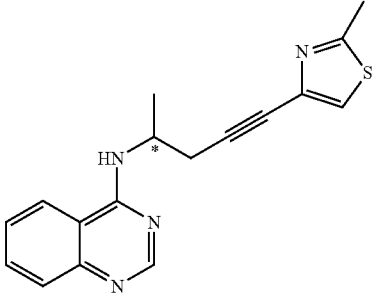 racemic | Resinoid product |
| 293 | 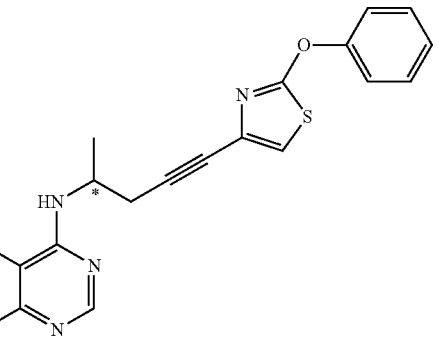 racemic | Resinoid product |
| 294 | 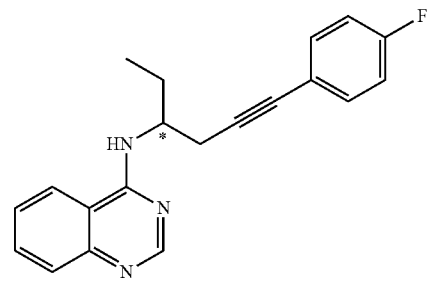 racemic | Oily product |

TABLE 1-55

| Compound No. | Structure | Physical property |
|---|---|---|
| 295 | (quinazolin-4-yl)NH-CH(Et)-C≡C-(2-CF3-4-F-phenyl), racemic | Oily product |
| 296 | (quinazolin-4-yl)NH-CH(vinyl)-CH2-C≡C-phenyl, racemic | Oily product |
| 297 | (quinazolin-4-yl)NH-CH(vinyl)-C≡C-(4-F-phenyl), racemic | Oily product |
| 298 | (quinazolin-4-yl)NH-CH(iPr)-C≡C-phenyl, racemic | Oily product |

TABLE 1-55-continued

| Compound No. | Structure | Physical property |
|---|---|---|
| 299 | (quinazolin-4-yl)NH-CH(CH2OH)-CH2-C≡C-phenyl, racemic | Oily product |
| 300 | (quinazolin-4-yl)NH-CH(phenyl)-CH2-C≡CH, racemic | m.p. 127~129° C. |

TABLE 1-56

| Compound No. | Structure | Physical property |
|---|---|---|
| 301 | (quinazolin-4-yl)NH-CH(phenyl)-C≡C-phenyl, racemic | m.p. 141~143° C. |
| 302 | (quinazolin-4-yl)NH-CH(phenyl)-C≡C-(2-CF3-phenyl), racemic | m.p. 150~152° C. |

TABLE 1-56-continued

| Compound No. | Structure | Physical property |
|---|---|---|
| 303 | (ethyl ester, phenyl alkyne, quinazoline-4-yl-NH, racemic) | Oily product |
| 304 | (ethyl ester, 2-CF₃-phenyl alkyne, quinazoline-4-yl-NH, racemic) | Oily product |
| 305 | (N-methyl amide, phenyl alkyne, quinazoline-4-yl-NH, racemic) | Resinoid product |

TABLE 1-57

| Compound No. | Structure | Physical property |
|---|---|---|
| 306 | 8-F-quinazoline-4-yl-NH-CH₂CH₂-C≡C-(2-CF₃-phenyl) | m.p. 118~124° C. |
| 307 | 8-Cl-quinazoline-4-yl-NH-CH₂CH₂-C≡C-(2-CF₃-phenyl) | m.p. 170~171° C. |
| 308 | 7-Cl-quinazoline-4-yl-NH-CH₂CH₂-C≡C-(2-CF₃-phenyl) | m.p. 153~154° C. |
| 309 | 6-Cl-quinazoline-4-yl-NH-CH₂CH₂-C≡C-(2-CF₃-phenyl) | m.p. 145~146° C. |
| 310 | 5-Cl-quinazoline-4-yl-NH-CH₂CH₂-C≡C-(2-CF₃-phenyl) | m.p. 95~97° C. |
| 311 | 8-Cl-quinazoline-4-yl-NH-CH₂CH₂-C≡C-(2-CH₂OMe-phenyl) | 159° C. |

TABLE 1-58

| Compound No. | Structure | Physical property |
|---|---|---|
| 312 | 7-Cl quinazoline, 4-NH-CH2CH2-C≡C-(2-CH2OMe-phenyl) | m.p. 118~120° C. |
| 313 | 6-Cl quinazoline, 4-NH-CH2CH2-C≡C-(2-CH2OMe-phenyl) | Resinoid product |
| 314 | 5-Cl quinazoline, 4-NH-CH2CH2-C≡C-(2-CH2OMe-phenyl) | Oily product |
| 315 | 8-F quinazoline, 4-NH-CH2CH2-C≡C-(2-CH2OMe-phenyl) | m.p. 143~144° C. |
| 316 | 7-F quinazoline, 4-NH-CH2CH2-C≡C-(2-CH2OMe-phenyl) | m.p. 113~115° C. |
| 317 | 6-F quinazoline, 4-NH-CH2CH2-C≡C-(2-CH2OMe-phenyl) | m.p. 121~122° C. |

TABLE 1-59

| Compound No. | Structure | Physical property |
|---|---|---|
| 318 | 5-F quinazoline, 4-NH-CH2CH2-C≡C-(2-CH2OMe-phenyl) | Resinoid product |
| 319 | 6,7-diF quinazoline, 4-NH-CH2CH2-C≡C-(2-CH2OMe-phenyl) | m.p. 117~119° C. |
| 320 | 7-Br quinazoline, 4-NH-CH2CH2-C≡C-(2-CH2OMe-phenyl) | m.p. 111~114° C. |
| 321 | 6-Br quinazoline, 4-NH-CH2CH2-C≡C-(2-CH2OMe-phenyl) | m.p. 118~120° C. |
| 322 | 6-I quinazoline, 4-NH-CH2CH2-C≡C-(2-CH2OMe-phenyl) | m.p. 121~123° C. |
| 323 | 8-CF3 quinazoline, 4-NH-CH2CH2-C≡C-(2-CH2OMe-phenyl) | Oily product |

TABLE 1-60

| Compound No. | Structure | Physical property |
|---|---|---|
| 324 | 7-CF3-quinazolin-4-yl-NH-CH2CH2-C≡C-(2-(MeOCH2)phenyl) | m.p. 77~79° C. |
| 325 | 8-Me-quinazolin-4-yl-NH-CH2CH2-C≡C-(2-(MeOCH2)phenyl) | Resinoid product |
| 326 | 6-Me-quinazolin-4-yl-NH-CH2CH2-C≡C-(2-(MeOCH2)phenyl) | Oily product |
| 327 | 6-Cl-8-Me-quinazolin-4-yl-NH-CH2CH2-C≡C-(2-(MeOCH2)phenyl) | Oily product |
| 328 | 8-OMe-quinazolin-4-yl-NH-CH2CH2-C≡C-(2-(MeOCH2)phenyl) | Resinoid product |
| 329 | 6-OMe-quinazolin-4-yl-NH-CH2CH2-C≡C-(2-(MeOCH2)phenyl) | Oily product |

TABLE 1-61

| Compound No. | Structure | Phyical property |
|---|---|---|
| 330 | 6-CN-quinazolin-4-yl-NH-CH2CH2-C≡C-(2-(MeOCH2)phenyl) | Oily product |
| 331 | 6-NO2-quinazolin-4-yl-NH-CH2CH2-C≡C-(2-(MeOCH2)phenyl) | Oily product |

TABLE 1-61-continued

| Compound No. | Structure | Phyical property |
|---|---|---|
| 332 | 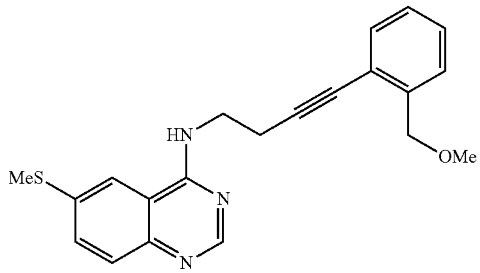 [SMILES: COCc1ccccc1C#CCCNc1ncnc2ccc(SC)cc12] | Oily product |
| 333 | 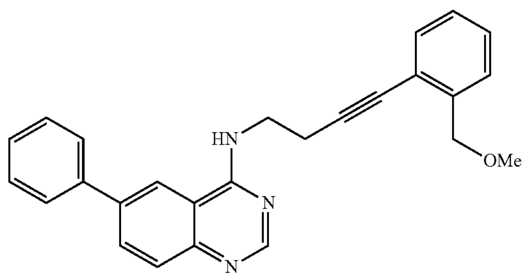 [SMILES: COCc1ccccc1C#CCCNc1ncnc2ccc(-c3ccccc3)cc12] | Resinoid product |
| 334 | 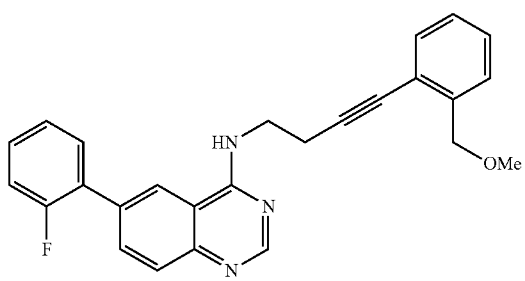 [SMILES: COCc1ccccc1C#CCCNc1ncnc2ccc(-c3ccccc3F)cc12] | Resinoid product |
| 335 | 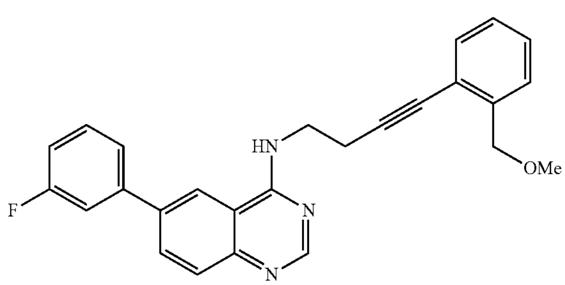 [SMILES: COCc1ccccc1C#CCCNc1ncnc2ccc(-c3cccc(F)c3)cc12] | Resinoid product |

TABLE 1-62

| Compound No. | Structure | Physical property |
|---|---|---|
| 336 | 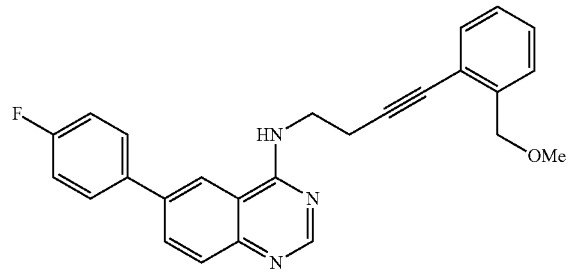 [SMILES: COCc1ccccc1C#CCCNc1ncnc2ccc(-c3ccc(F)cc3)cc12] | m.p. 168~170° C. |
| 337 | 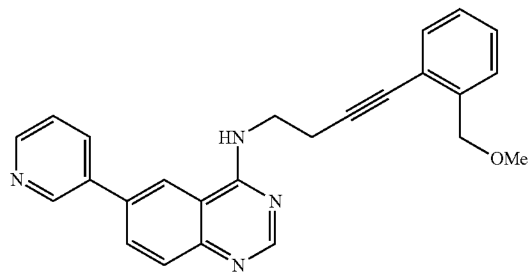 [SMILES: COCc1ccccc1C#CCCNc1ncnc2ccc(-c3cccnc3)cc12] | Resinoid product |
| 338 | 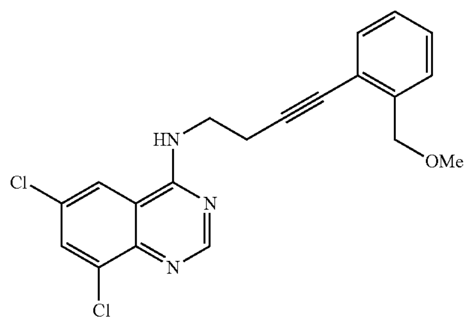 [SMILES: COCc1ccccc1C#CCCNc1ncnc2c(Cl)cc(Cl)cc12] | m.p. 161~162° C. |
| 339 | 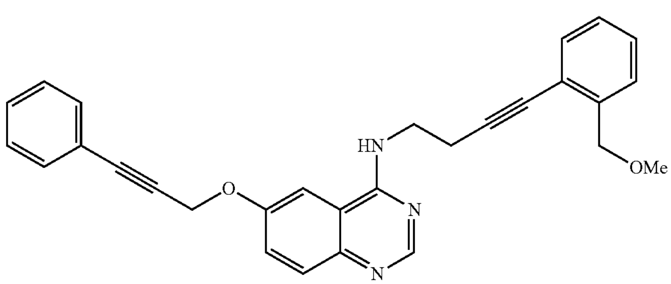 [SMILES: COCc1ccccc1C#CCCNc1ncnc2ccc(OCC#Cc3ccccc3)cc12] | Oily product |
| 340 | 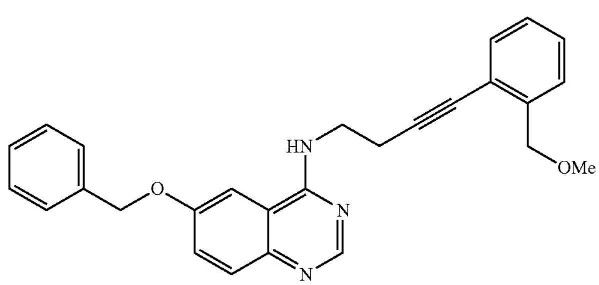 [SMILES: COCc1ccccc1C#CCCNc1ncnc2ccc(OCc3ccccc3)cc12] | Oily product |

TABLE 1-62-continued

| Compound No. | Structure | Physical property |
|---|---|---|
| 341 | (6,8-dimethylquinazolin-4-yl)-NH-CH2CH2-C≡C-(2-(CH2OMe)phenyl) | Oily product |

TABLE 1-63

| Compound No. | Structure | Physical property |
|---|---|---|
| 342 | (benzo[g]quinazolin-4-yl)-NH-CH2CH2-C≡C-(2-CF3-phenyl) | >240° C. |
| 343 | (8-F-quinazolin-4-yl)-NH-CH(*CH3)-CH2-C≡C-(2-CF3-phenyl), racemic | m.p. 105~108° C. |
| 344 | (7-F-quinazolin-4-yl)-NH-CH(*CH3)-CH2-C≡C-(4-Cl-2-CF3-phenyl), racemic | Oily product |
| 345 | (6-F-quinazolin-4-yl)-NH-CH(*CH3)-CH2-C≡C-(4-Cl-2-CF3-phenyl), racemic | Resinoid product |

TABLE 1-63-continued

| Compound No. | Structure | Physical property |
|---|---|---|
| 346 | (5-F-quinazolin-4-yl)-NH-CH(*CH3)-CH2-C≡C-(4-Cl-2-CF3-phenyl), racemic | Oily product |
| 347 | (7-F-quinazolin-4-yl)-NH-CH(*CH3)-CH2-C≡C-(4-F-2-CF3-phenyl), racemic | Oily product |

TABLE 1-64

| Compound No. | Structure | Physical property |
|---|---|---|
| 348 | (8-F-quinazolin-4-yl)-NH-CH(*CH3)-CH2-C≡C-(4-Cl-2-CF3-phenyl), racemic | m.p. 118~121° C. |

TABLE 1-64-continued

| Compound No. | Structure | Physical property |
|---|---|---|
| 349 | 8-Cl quinazolin-4-yl-NH-CH(CH3)-C≡C-(4-Cl,2-CF3-phenyl), racemic | m.p. 129~135° C. |
| 350 | 5-Cl quinazolin-4-yl-NH-CH(CH3)-C≡C-(4-Cl,2-CF3-phenyl), racemic | Oily product |
| 351 | 8-CF3 quinazolin-4-yl-NH-CH(CH3)-C≡C-(4-Cl,2-CF3-phenyl), racemic | Oily product |
| 352 | 8-OMe quinazolin-4-yl-NH-CH(CH3)-C≡C-(4-Cl,2-CF3-phenyl), racemic | m.p. 197~198° C. |

TABLE 1-65

| Compound No. | Structure | Physical property |
|---|---|---|
| 353 | 8-OMe quinazolin-4-yl-NH-CH(CH3)-C≡C-(4-F,2-CF3-phenyl), racemic | m.p. 160~161° C. |
| 354 | 8-Me quinazolin-4-yl-NH-CH(CH3)-C≡C-(4-Cl,2-CF3-phenyl), racemic | Oily product |
| 355 | 6,7-diF quinazolin-4-yl-NH-CH2CH2-C≡C-(4-Cl,2-CF3-phenyl) | Resinoid product |
| 356 | 6-Cl,5-Me pyrimidin-4-yl-NH-CH2CH2-C≡C-phenyl | m.p. 112~114° C. |
| 357 | 5,6-diCl pyrimidin-4-yl-NH-CH2CH2-C≡C-phenyl | m.p. 122~123° C. |

TABLE 1-66

| Compound No. | Structure | Physical property |
|---|---|---|
| 358 | (6-chloropyrimidin-4-yl)-NH-CH2CH2-C≡C-phenyl | m.p. 118~120° C. |
| 359 | (6-methylpyrimidin-4-yl)-NH-CH2CH2-C≡C-(2-CF3,4-Cl-phenyl) | Oily product |
| 360 | (5-chloro-6-methylpyrimidin-4-yl)-NH-CH2CH2-C≡C-(2-CF3,4-Cl-phenyl) | m.p. 91~93° C. |
| 361 | (5-chloro-6-methylpyrimidin-4-yl)-NH-CH2CH2-C≡C-(2-CH2OMe,4-Me-phenyl) | Resinoid product |
| 362 | (5-chloro-6-methylpyrimidin-4-yl)-NH-CH2CH2-C≡C-(2-CH2OMe-phenyl) | Resinoid product |

TABLE 1-66-continued

| Compound No. | Structure | Physical property |
|---|---|---|
| 363 | (6-chloro-5-methylpyrimidin-4-yl)-NH-CH2CH2-C≡C-(2-CH2OMe-phenyl) | Oily product |

TABLE 1-67

| Compound No. | Structure | Physical property |
|---|---|---|
| 364 | (6-chloro-5-methylpyrimidin-4-yl)-NH-CH2CH2-C≡C-(2-CF3-phenyl) | Resinoid product |
| 365 | (5,6-dichloropyrimidin-4-yl)-NH-CH2CH2-C≡C-(2-CH2OMe-phenyl) | Oily product |
| 366 | (5-bromo-6-chloropyrimidin-4-yl)-NH-CH2CH2-C≡C-(2-CH2OMe-phenyl) | Oily product |
| 367 | (5-bromo-6-chloropyrimidin-4-yl)-NH-CH2CH2-C≡C-(2-CF3-phenyl) | m.p. 102~103° C. |

TABLE 1-67-continued

| Compound No. | Structure | Physical property |
|---|---|---|
| 368 | 4-chloro-6-[(4-(2-trifluoromethylphenyl)but-3-yn-1-yl)amino]-5-aminopyrimidine | Oily product |
| 369 | 5-nitro-4-methylsulfonyl-6-[(4-(2-trifluoromethylphenyl)but-3-yn-1-yl)amino]pyrimidine | Resinoid product |

TABLE 1-68

| Compound No. | Structure | Physical property |
|---|---|---|
| 370 | 6-chloro-5-nitro-4-[(4-(2-trifluoromethylphenyl)but-3-yn-1-yl)amino]pyrimidine | Oily product |
| 371 | 5-nitro-6-methylthio-4-[(4-(2-trifluoromethylphenyl)but-3-yn-1-yl)amino]pyrimidine | Resinoid product |
| 372 | 5-benzyl-6-chloro-4-[(4-phenylbut-3-yn-1-yl)amino]pyrimidine | m.p. 157~158° C. |

TABLE 1-68-continued

| Compound No. | Structure | Physical property |
|---|---|---|
| 373 | 6-chloro-5-phenyl-4-[(4-phenylbut-3-yn-1-yl)amino]pyrimidine | Resinoid product |
| 374 | 6-(1-fluoroethyl)-5-iodo-4-[(4-phenylbut-3-yn-1-yl)amino]pyrimidine, racemic | Oily product |
| 375 | 5-bromo-6-(1-fluoroethyl)-4-[(4-phenylbut-3-yn-1-yl)amino]pyrimidine, racemic | Oily product |

TABLE 1-69

| Compound No. | Structure | Physical property |
|---|---|---|
| 376 | 5-chloro-6-(1-fluoroethyl)-4-[(4-phenylbut-3-yn-1-yl)amino]pyrimidine, racemic | m.p. 84~86° C. |

TABLE 1-69-continued

| Compound No. | Structure | Physical property |
|---|---|---|
| 377 | 5-chloro-6-(1-fluoroethyl)-N-[4-(4-chloro-2-trifluoromethylphenyl)-3-butyn-1-yl]pyrimidin-4-amine (racemic) | Oily product |
| 378 | N-(4-phenyl-3-butyn-1-yl)-9H-purin-6-amine | m.p. 207~208° C. |
| 379 | N-(4-phenyl-3-butyn-1-yl)-7H-pyrrolo[2,3-d]pyrimidin-4-amine | Resinoid product |
| 380 | N-[4-(2-methoxymethylphenyl)-3-butyn-1-yl]pyrido[2,3-d]pyrimidin-4-amine | m.p. 158~161° C. |

TABLE 1-70

| Compound No. | Structure | Physical property |
|---|---|---|
| 381 | 5-iodo-6-(1-fluoroethyl)-N-(4-phenyl-3-butyn-2-yl)pyrimidin-4-amine (racemic) | Oily product |
| 382 | 5-chloro-6-(1-fluoroethyl)-N-[4-(4-chloro-2-trifluoromethylphenyl)-3-butyn-2-yl]pyrimidin-4-amine (racemic) | Oily product |
| 383 | 5-chloro-6-(1-chloroethyl)-N-[4-(4-chloro-2-trifluoromethylphenyl)-3-butyn-2-yl]pyrimidin-4-amine (racemic) | Oily product |
| 384 | N-[4-(4-chloro-2-trifluoromethylphenyl)-3-butyn-2-yl]pyrido[2,3-d]pyrimidin-4-amine (racemic) | m.p. 176~180° C. |
| 385 | 5-chloro-6-methyl-N-[4-(4-chloro-2-trifluoromethylphenyl)-3-butyn-2-yl]pyrimidin-4-amine (racemic) | Resinoid product |

TABLE 1-70-continued

| Compound No. | Structure | Physical property |
|---|---|---|
| 386 | 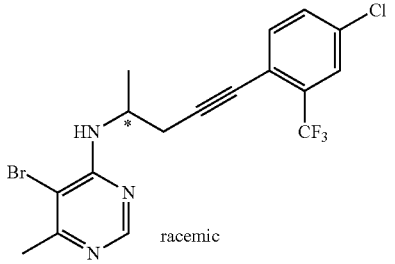 [SMILES: Cc1ncnc(NC(C)CC#Cc2ccc(Cl)cc2C(F)(F)F)c1Br] racemic | Resinoid product |

TABLE 1-71

| Compound No. | Structure | Physical property |
|---|---|---|
| 387 | 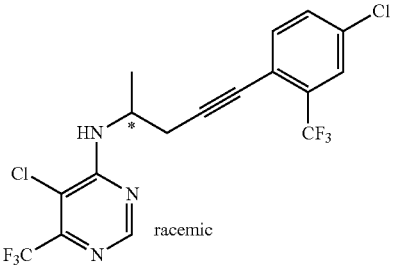 [SMILES: CC(CC#Cc1ccc(Cl)cc1C(F)(F)F)Nc1ncnc(C(F)(F)F)c1Cl] racemic | Resinoid product |
| 388 | (structure with Cl, CF₃, Cl, F₃C, pyrimidine) racemic | m.p. 96~98° C. |
| 389 | 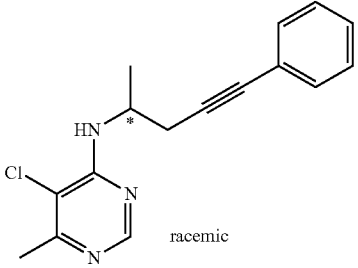 [SMILES: Cc1ncnc(NC(C)CC#Cc2ccccc2)c1Cl] racemic | Resinoid product |

TABLE 2-1

| Compound No. | δ value (ppm, solvent: CDCl₃, internal standard substance: TMS) |
|---|---|
| 1 | 2.05 (t, 1H), 2.60 (dt, 2H), 3.80 (q, 2H), 5.82 (brs, 1H), 7.18 (d, 2H), 7.28 (d, 2H), 8.51 (s, 1H) |
| 2 | 0.05 (s, 9H), 2.47 (t, 2H), 3.63 (q, 2H), 5.52 (brs, 1H), 6.97 (d, 2H), 7.13 (d, 2H), 8.35 (s, 1H) |

TABLE 2-1-continued

| Compound No. | δ value (ppm, solvent: CDCl₃, internal standard substance: TMS) |
|---|---|
| 3 | 0.43-0.71 (m, 6H), 0.91-1.10 (m, 9H), 2.65 (t, 2H), 3.78 (q, 2H), 5.62 (brs, 1H), 7.10 (d, 2H), 7.29 (d, 2H), 8.50 (s, 1H) |
| 4 | 1.06 (s, 21H), 2.67 (t, 2H), 3.81 (q, 1H), 5.51 (brs, 1H), 7.08 (d, 2H), 7.28 (d, 2H), 8.51 (s, 1H) |
| 5 | 0.05 (s, 6H), 0.83 (s, 9H), 2.55 (t, 2H), 3.69 (q, 2H), 5.42 (brs, 1H), 7.00 (d, 2H), 7.19 (d, 2H), 8.41 (s, 1H) |
| 6 | 0.90 (t, 3H), 1.26-1.53 (m, 4H), 2.08-2.24 (m, 2H), 2.46-2.66 (m, 2H), 3.74 (q, 2H), 5.68 (brs, 1H), 7.14 (d, 2H), 7.29 (d, 2H), 8.51 (s, 1H) |
| 7 | 1.02 (d, 6H), 1.70-1.84 (m, 1H), 2.00-2.12 (m, 2H), 2.48-2.67 (m, 2H), 3.75 (q, 2H), 5.76 (brs, 1H), 7.14 (d, 2H), 7.28 (d, 2H), 8.50 (s, 1H) |
| 8 | 1.21 (s, 9H), 2.55 (t, 2H), 3.74 (q, 2H), 5.52 (brs, 1H), 7.12 (d, 2H), 7.29 (d, 2H), 8.51 (s, 1H) |
| 9 | 2.52-2.72 (m, 2H), 3.55-3.67 (m, 2H), 3.80 (q, 2H), 5.74 (brs, 1H), 6.97-7.35 (m, 7H), 8.46 (s, 1H) |
| 10 | 2.79 (t, 2H), 3.90 (q, 2H), 5.67 (brs, 1H), 7.18-7.46 (m, 7H), 8.53 (s, 1H) |
| 11 | 2.86 (t, 2H), 3.88 (q, 2H), 5.53 (brs, 1H), 6.96-7.40 (m, 6H), 8.52 (s, 1H) |
| 12 | 2.83 (t, 2H), 3.87 (q, 2H), 5.53 (brs, 1H), 6.90-7.60 (m, 6H), 8.53 (s, 1H) |
| 13 | 2.82 (t, 2H), 3.87 (q, 2H), 5.58 (brs, 1H), 6.88-7.44 (m, 6H), 8.53 (s, 1H) |
| 14 | 2.85 (t, 2H), 3.91 (q, 2H), 5.72 (brs, 1H), 7.10-7.48 (m, 6H), 8.52 (s, 1H) |
| 15 | 2.83 (t, 2H), 3.82 (q, 2H), 5.51 (brs, 1H), 6.96-7.63 (m, 6H), 8.53 (s, 1H) |

TABLE 2-2

| Compound No. | δ value (ppm, solvent: CDCl₃, internal standard substance: TMS) |
|---|---|
| 16 | 2.83 (t, 2H), 3.86 (q, 2H), 5.59 (brs, 1H), 7.07-7.41 (m, 6H), 8.52 (s, 1H) |
| 17 | 2.39 (s, 3H), 2.81 (d, 2H), 3.89 (q, 2H), 5.60 (brs, 1H), 7.13-7.68 (m, 6H), 8.52 (s, 1H) |
| 18 | 2.27 (s, 3H), 2.80 (t, 2H), 3.85 (q, 2H), 5.56 (brs, 1H), 6.90-7.60 (m, 6H), 8.52 (s, 1H) |
| 19 | 2.31 (s, 3H), 2.80 (t, 2H), 3.86 (q, 2H), 6.07 (t, 1H), 7.01-7.31 (m, 6H), 8.52 (s, 1H) |
| 20 | 1.29 (s, 9H), 2.81 (t, 2H), 3.85 (q, 2H), 5.87 (brs, 1H), 7.11-7.31 (m, 6H), 8.52 (s, 1H) |
| 21 | 2.85 (t, 2H), 3.84 (s, 3H), 3.86 (q, 4H), 6.03 (brs, 1H), 6.79-6.96 (m, 2H), 7.14-7.41 (m, 4H), 8.52 (s, 1H) |
| 22 | 2.83 (t, 2H), 3.78 (s, 3H), 3.88 (q, 2H), 5.58 (brs, 1H), 6.78-7.33 (m, 6H), 8.53 (s, 1H) |
| 23 | 2.80 (t, 2H), 3.78 (s, 3H), 3.82 (q, 2H), 5.82 (t, 1H), 6.83 (d, 2H), 7.11-7.36 (m, 4H), 8.52 (s, 1H) |
| 24 | 2.82 (t, 2H), 3.85 (s, 3H), 3.87 (s, 3H), 3.90 (q, 2H), 5.72 (brs, 1H), 6.72-7.31 (m, 5H), 8.53 (s, 1H) |
| 25 | 2.86 (t, 2H), 3.90 (q, 2H), 5.62 (brs, 1H), 7.18-7.70 (m, 6H), 8.52 (s, 1H) |
| 26 | 2.85 (t, 2H), 3.87 (q, 2H), 5.62 (brs, 1H), 7.11-7.67 (m, 6H), 8.52 (s, 1H) |
| 27 | 2.83 (t, 2H), 3.87 (q, 2H), 7.10-7.62 (m, 6H), 8.53 (s, 1H) |
| 28 | 2.83 (t, 2H), 3.88 (q, 2H), 7.18-7.72 (m, 5H), 8.54 (s, 1H) |
| 29 | 2.80 (t, 2H), 3.88-4.08 (m, 5H), 6.94 (brs, 1H), 7.16-7.67 (m, 5H), 8.02 (d, 1H), 8.49 (s, 1H) |
| 30 | 2.85 (t, 2H), 3.80-4.00 (m, 5H), 7.12-7.54 (m, 4H), 7.92-8.07 (m, 2H), 8.53 (s, 1H) |
| 31 | 2.86 (t, 2H), 3.88 (q, 2H), 3.90 (s, 3H), 5.76 (brs, 1H), 7.13-7.46 (m, 4H), 7.95 (d, 2H), 8.53 (s, 1H) |
| 32 | 2.87 (t, 2H), 3.90 (q, 2H), 5.66 (brs, 1H), 7.06-7.51 (m, 6H), 8.52 (s, 1H) |

TABLE 2-3

| Compound No. | δ value (ppm, solvent: CDCl$_3$, internal standard substance: TMS) |
|---|---|
| 33 | 2.77 (t, 2H), 2.88 (q, 2H), 5.62 (brs, 1H), 7.12-7.33 (m, 6H), 8.53 (s, 1H) |
| 34 | 2.83 (t, 2H), 2.78 (q, 2H), 5.55 (brs, 1H), 7.08-7.45 (m, 6H), 8.52 (s, 1H) |
| 35 | 2.89 (t, 2H), 3.97 (q, 2H), 6.25 (brs, 1H), 7.22-7.61 (m, 6H), 8.50 (s, 1H) |
| 36 | 2.86 (t, 2H), 3.89 (q, 2H), 7.13-7.64 (m, 6H), 8.53 (s, 1H) |
| 37 | 2.88 (t, 2H), 3.88 (q, 2H), 7.17-7.82 (m, 6H), 8.51 (s, 1H) |
| 38 | 2.86 (t, 2H), 3.96 (q, 2H), 7.21-7.61 (m, 5H), 8.04 (d, 1H), 8.50 (s, 1H) |
| 39 | 2.85 (t, 2H), 3.91 (q, 2H), 5.58 (brs, 1H), 7.09-7.71 (m, 5H), 8.11 (d, 1H), 8.54 (s, 1H) |
| 40 | 2.90 (t, 2H), 3.92 (q, 2H), 5.48 (brs, 1H), 7.11-7.57 (m, 5H), 8.12 (d, 1H), 8.54 (s, 1H) |
| 41 | 2.85 (t, 2H), 3.87 (q, 2H), 5.55 (brs, 1H), 6.73-7.34 (m, 5H), 8.52 (s, 1H) |
| 42 | 2.90 (t, 2H), 3.92 (q, 2H), 5.65 (brs, 1H), 6.90-7.34 (m, 5H), 8.52 (s, 1H) |
| 43 | 2.83 (t, 2H), 3.92 (q, 2H), 5.50 (brs, 1H), 6.92-7.32 (m, 5H), 8.51 (s, 1H) |
| 44 | 2.82 (t, 2H), 3.90 (q, 2H), 4.78 (d, 2H), 6.10 (brs, 1H), 7.13-7.41 (m, 6H), 8.50 (s, 1H) |
| 45 | 2.83 (t, 2H), 3.33 (s, 3H), 3.90 (q, 2H), 4.60 (s, 2H), 6.15 (brs, 1H), 7.15-7.45 (m, 6H), 8.51 (s, 1H) |
| 46 | 1.22 (t, 3H), 2.83 (t, 2H), 3.50 (q, 2H), 3.92 (q, 2H), 4.65 (s, 2H), 6.20 (brs, 1H), 7.15-7.45 (m, 6H), 8.51 (s, 1H) |
| 47 | 2.86 (t, 2H), 3.92 (q, 2H), 5.25 (s, 1H), 5.74 (brs, 1H), 5.78 (s, 1H), 7.14-7.44 (m, 6H), 8.52 (s, 1H) |
| 48 | 2.90 (t, 2H), 3.92 (t, 2H), 7.24-7.89 (m, 6H), 8.45 (s, 1H), 10.37 (s, 1H) |
| 49 | 2.85 (t, 2H), 3.37 (s, 3H), 3.90 (q, 2H), 4.60 (s, 2H), 6.00 (brs, 1H), 7.18-7.71 (m, 6H), 8.64 (s, 1H) |

TABLE 2-4

| Compound No. | δ value (ppm, solvent: CDCl$_3$, internal standard substance: TMS) |
|---|---|
| 50 | 2.20 (s, 3H), 2.83 (t, 2H), 3.34 (s, 3H), 3.90 (q, 2H), 4.70 (s, 2H), 6.06 (brs, 1H), 7.10-7.62 (m, 5H), 8.66 (s, 1H) |
| 51 | 2.56 (s, 3H), 2.87 (t, 2H), 3.32 (s, 3H), 3.87 (q, 2H), 4.60 (s, 2H), 5.92 (brs, 1H), 6.80 (s, 1H), 7.17-7.48 (m, 4H), 8.44 (s, 1H) |
| 52 | 2.80 (t, 2H), 3.82 (q, 2H), 6.20 (brs, 1H), 6.34-6.36 (m, 1H), 7.12-7.57 (m, 4H), 8.50 (s, 1H) |
| 53 | 2.82 (t, 2H), 3.84 (q, 2H), 5.88 (brs, 1H), 6.87-7.30 (m, 5H), 8.52 (s, 1H) |
| 54 | 2.80 (t, 2H), 3.85 (q, 2H), 6.23 (brs, 1H), 7.02-7.38 (m, 5H), 8.52 (s, 1H) |
| 55 | 2.85 (t, 2H), 3.90 (q, 2H), 6.24 (brs, 1H), 7.12-7.72 (m, 5H), 8.48-8.57 (m, 2H) |
| 56 | 2.85 (t, 2H), 3.90 (q, 2H), 5.56 (brs, 1H), 7.12-7.34 (m, 4H), 7.58-7.78 (m, 1H), 8.45-8.68 (m, 3H) |
| 57 | 2.87 (t, 2H), 3.90 (q, 2H), 5.62 (brs, 1H), 7.12-7.35 (m, 4H), 8.45-8.58 (m, 3H) |
| 58 | 2.90 (t, 2H), 3.95 (q, 2H), 5.85 (brs, 1H), 7.15-7.27 (m, 3H), 8.50 (s, 1H), 8.75 (d, 2H) |
| 59 | 2.42 (s, 6H), 2.90 (t, 2H), 3.92 (q, 2H), 6.30 (brs, 1H), 6.97 (s, 1H), 7.24-7.32 (m, 4H), 8.50 (s, 1H) |
| 60 | 2.87 (t, 2H), 3.94 (q, 2H), 3.95 (s, 6H), 6.00 (s, 1H), 7.45 (d, 2H), 7.60 (d, 2H), 8.48 (s, 1H), 8.87 (s, 1H) |
| 61 | 2.86 (t, 2H), 3.88 (q, 2H), 5.52 (brs, 1H), 7.15 (d, 2H), 7.30 (d, 2H), 7.89 (s, 1H), 8.52 (s, 1H), 8.68 (s, 1H) |
| 62 | 3.86 (t, 2H), 3.90 (q, 2H), 5.86 (brs, 1H), 7.18-7.28 (m, 3H), 7.77 (d, 2H), 8.48 (s, 1H) |
| 63 | 2.88 (t, 3H), 3.90 (q, 2H), 6.04 (brs, 1H), 7.40 (d, 2H), 7.24 (s, 1H), 8.52 (s, 1H), 8.75 (d, 2H) |
| 64 | 2.90 (t, 2H), 3.82 (q, 2H), 6.16 (brs, 1H), 7.17-7.27 (m, 3H), 8.50 (s, 1H) |

TABLE 2-4-continued

| Compound No. | δ value (ppm, solvent: CDCl$_3$, internal standard substance: TMS) |
|---|---|
| 65 | 2.51 (s, 3H), 2.88 (t, 2H), 3.91 (q, 2H), 5.92 (brs, 1H), 7.16-7.26 (m, 3H), 8.52 (s, 1H) |

TABLE 2-5

| Compound No. | δ value (ppm, solvent: CDCl$_3$, internal standard substance: TMS) |
|---|---|
| 66 | 2.38 (s, 3H), 2.88 (t, 2H), 3.90 (q, 2H), 6.04 (brs, 1H), 7.17-7.25 (m, 3H), 8.51 (s, 1H) |
| 67 | 2.82 (t, 2H), 3.90 (q, 2H), 4.09 (s, 3H), 5.74 (brs, 1H), 6.75 (s, 1H), 7.16 (d, 1H), 7.28 (d, 1H), 8.51 (s, 1H) |
| 68 | 2.85 (t, 3H), 3.88 (q, 2H), 5.33 (s, 1H), 5.85 (brs, 2H), 7.15-7.42 (m, 3H), 8.51 (s, 1H) |
| 69 | 2.90 (t, 3H), 3.91 (q, 2H), 5.75 (brs, 1H), 7.21-7.30 (m, 2H), 7.70 (s, 1H), 8.52 (s, 1H), 9.95 (s, 1H) |
| 70 | 2.79 (t, 2H), 3.70 (q, 2H), 4.67 (d, 2H), 6.00 (t, 1H), 7.51 (s, 2H), 7.65 (s, 1H), 8.37 (s, 1H) |
| 71 | 0.13 (s, 6H), 0.95 (s, 9H), 2.83 (t, 2H), 3.87 (q, 2H), 4.92 (s, 2H), 5.82 (brs, 1H), 7.22-7.31 (m, 3H), 8.51 (s, 1H) |
| 72 | 2.83 (t, 3H), 3.48 (s, 3H), 3.87 (q, 2H), 4.70 (s, 2H), 6.09 (brs, 1H), 7.23-7.41 (m, 3H), 8.51 (s, 1H) |
| 73 | 2.16 (s, 3H), 2.85 (t, 3H), 3.88 (q, 2H), 5.34 (s, 2H), 5.73 (brs, 1H), 7.15-7.36 (m, 3H), 8.51 (s, 1H) |
| 74 | 2.51 (t, 1H), 2.84 (t, 2H), 3.88 (q, 2H), 4.30 (d, 2H), 4.86 (s, 2H), 5.90 (brs, 1H), 7.17-7.35 (m, 3H), 8.51 (s, 1H) |
| 75 | 2.83 (t, 2H), 3.86 (q, 2H), 4.29 (s, 2H), 5.82 (brs, 1H), 7.13-7.30 (m, 8H), 8.51 (s, 1H) |
| 76 | 2.87 (t, 2H), 3.90 (q, 2H), 5.82 (brs, 1H), 7.14-7.51 (m, 6H), 7.90-8.00 (m, 2H), 8.52 (s, 1H) |
| 77 | 2.85 (t, 2H), 3.88 (q, 4H), 5.87 (brs, 1H), 6.83 (d, 1H), 7.16-7.31 (m, 4H), 7.47 (t, 1H), 8.01 (s, 1H), 8.52 (s, 1H) |
| 78 | 2.82 (t, 2H), 3.86 (q, 2H), 5.93 (brs, 1H), 7.16-7.59 (m, 5H), 7.85-7.90 (m, 1H), 8.52 (s, 1H) |
| 79 | 2.81 (t, 2H), 3.85 (q, 2H), 6.22 (t, 1H), 7.00-8.48 (m, 6H), 8.50 (s, 1H) |
| 80 | 2.82 (t, 2H), 3.88 (q, 2H), 5.93 (brs, 1H), 7.16-7.59 (m, 5H), 7.85-7.90 (m, 1H), 8.52 (s, 1H) |
| 81 | 2.89 (t, 2H), 3.92 (q, 2H), 5.77 (brs, 1H), 7.16-7.45 (m, 4H), 8.18-8.31 (m, 1H), 8.53 (s, 1H), 8.64-8.70 (m, 1H), 9.15 (s, 1H) |

TABLE 2-6

| Compound No. | δ value (ppm, solvent: CDCl$_3$, internal standard substance: TMS) |
|---|---|
| 82 | 2.86 (t, 2H), 3.90 (q, 2H), 5.85 (brs, 1H), 7.27 (s, 2H), 7.39-7.48 (m, 3H), 7.76 (s, 1H), 7.99-8.09 (m, 2H), 8.51 (s, 1H) |
| 83 | 2.77 (t, 2H), 3.82 (q, 2H), 5.85 (brs, 1H), 6.85 (s, 1H), 7.11-7.41 (m, 7H), 8.49 (s, 1H) |
| 84 | 2.90 (t, 2H), 3.15 (s, 3H), 3.92 (q, 2H), 7.10-7.80 (m, 5H), 8.52 (s, 1H) |
| 85 | 2.95 (t, 3H), 3.87 (s, 3H), 3.92 (q, 2H), 5.84 (brs, 1H), 7.10-7.92 (m, 5H), 8.50 (s, 1H) |
| 86 | 2.08 (t, 1H), 2.64 (dt, 2H), 3.85 (q, 2H), 6.19 (brs, 1H), 7.44-7.91 (m, 4H), 8.67 (s, 1H) |
| 87 | 0.17 (s, 9H), 2.67 (t, 2H), 3.83 (q, 2H), 6.12 (brs, 1H), 7.45-7.84 (m, 4H), 8.67 (s, 1H) |
| 88 | 0.89 (t, 2H), 1.27-1.54 (m, 4H), 2.12-2.21 (m, 2H), 2.60 (dt, 2H), 3.78 (q, 2H), 6.32 (brs, 1H), 7.28-7.81 (m, 4H), 8.67 (s, 1H) |
| 89 | 0.87 (t, 3H), 1.25-1.57 (m, 8H), 2.11-2.02 (m, 2H), 2.50-2.70 (m, 2H), 3.78 (q, 2H), 6.30 (brs, 1H), 7.19-7.81 (m, 4H), 8.67 (s, 1H) |

TABLE 2-6-continued

| Compound No. | δ value (ppm, solvent: CDCl₃, internal standard substance: TMS) |
|---|---|
| 90 | 0.61-0.87 (m, 4H), 1.13-1.25 (m, 1H), 2.57 (dt, 2H), 3.76 (q, 2H), 6.17 (brs, 1H), 7.19-7.90 (m, 4H), 8.66 (s, 1H) |
| 91 | 1.26-1.79 (m, 10H), 2.39 (brs, 1H), 2.64 (t, 2H), 3.78 (q, 2H), 6.10 (brs, 1H), 7.45-7.90 (m, 4H), 8.66 (s, 1H) |
| 92 | 2.82 (t, 2H), 3.88 (q, 2H), 4.18 (s, 2H), 3.44 (d, 2H), 6.14 (brs, 1H), 7.41-7.82 (m, 4H), 8.66 (s, 1H) |
| 93 | 1.99-2.07 (m, 3H), 2.84-2.99 (m, 2H), 3.78-4.02 (m, 2H), 6.00-6.18 (m, 1H), 6.61 (brs, 1H), 7.10-7.99 (m, 4H), 8.67 (brs, 1H) |
| 94 | 1.53-1.66 (m, 4H), 2.03-2.10 (m, 4H), 2.74 (t, 2H), 3.83 (q, 2H), 6.04-6.16 (m, 2H), 7.19-7.82 (m, 4H), 8.67 (s, 1H) |
| 95 | 3.88 (t, 2H), 3.94 (q, 2H), 5.70 (d, 2H), 7.11-8.02 (m, 9H), 8.68 (s, 1H) |
| 96 | 2.88 (t, 2H), 3.92 (q, 2H), 6.18 (brs, 1H), 7.21-7.82 (m, 9H), 8.65 (s, 1H) |
| 97 | 2.92 (t, 2H), 3.95 (q, 2H), 6.22 (brs, 1H), 7.12-7.91 (m, 8H), 8.68 (s, 1H) |

TABLE 2-7

| Compound No. | δ value (ppm, solvent: CDCl₃, internal standard substance: TMS) |
|---|---|
| 98 | 2.90 (t, 2H), 4.00 (q, 2H), 7.00-8.35 (m, 9H), 8.65 (s, 1H) |
| 99 | 2.89 (t, 2H), 3.94 (q, 2H), 5.24 (s, 1H), 5.77 (s, 1H), 6.46 (brs, 1H), 7.26-7.83 (m, 8H), 8.68 (s, 1H) |
| 100 | 2.91 (t, 2H), 3.95 (q, 2H), 6.33 (brs, 1H), 6.95 (dd, 1H), 7.26-7.82 (m, 8H), 8.69 (s, 1H) |
| 101 | 2.91 (t, 2H), 3.95 (q, 2H), 6.10 (brs, 1H), 7.37-7.80 (m, 8H), 8.65 (s, 1H) |
| 102 | 2.94 (t, 2H), 4.05 (q, 2H), 7.37-7.80 (m, 8H), 8.66 (s, 1H) |
| 103 | 1.94 (t, 3H), 2.65-2.99 (m, 4H), 3.94 (q, 2H), 6.05 (brs, 1H), 7.19-7.83 (m, 8H), 8.69 (s, 1H) |
| 104 | 1.20 (d, 6H), 2.91 (t, 2H), 3.40 (m, 1H), 3.94 (q, 2H), 6.22 (brs, 1H), 6.96-7.80 (8H), 8.68 (s, 1H) |
| 105 | 1.72 (s, 3H), 2.59-2.98 (m, 4H), 2.88 (t, 2H), 3.88 (q, 2H), 4.67 (s, 2H), 6.09 (brs, 1H), 7.06-7.83 (m, 8H), 8.68 (s, 1H) |
| 106 | 0.82 (t, 3H), 1.16-1.68 (m, 4H), 2.55 (t, 2H), 3.84 (t, 2H), 3.88 (q, 2H), 6.11 (brs, 1H), 6.91-7.81 (m, 8H), 8.68 (s, 1H) |
| 107 | 0.85 (t, 3H), 1.13-1.72 (m, 8H), 2.56 (t, 2H), 3.85 (t, 2H), 3.92 (q, 2H), 6.14 (brs, 1H), 6.96-7.81 (m, 8H), 8.67 (s, 1H) |
| 108 | 0.85 (t, 3H), 1.05-1.67 (m, 12H), 2.59 (t, 2H), 2.86 (t, 2H), 3.90 (q, 2H), 6.09 (brs, 1H), 6.98-7.81 (m, 8H), 8.68 (s, 1H) |
| 109 | 1.11-1.88 (m, 12H), 2.22-2.70 (m, 1H), 2.82 (t, 2H), 3.90 (q, 2H), 6.10 (brs, 1H), 7.08-7.81 (m, 8H), 8.67 (s, 1H) |
| 110 | 2.88 (t, 2H), 3.91 (q, 2H), 5.26 (d, 1H), 5.72 (d, 1H), 6.39 (brs, 1H), 6.68 (dd, 2H), 7.26-8.00 (m, 8H), 8.68 (s, 1H) |
| 111 | 0.26 (s, 9H), 2.87 (t, 2H), 3.90 (q, 2H), 7.30-7.84 (m, 8H), 8.68 (s, 1H) |
| 112 | 0.88 (t, 3H), 1.15-1.67 (m, 10H), 2.60 (t, 2H), 2.88 (t, 2H), 3.90 (q, 2H), 6.10 (brs, 1H), 7.20-7.84 (m, 12H), 8.69 (s, 1H) |
| 113 | 2.87 (t, 2H), 3.92 (q, 2H), 5.25 (dd, 1H), 6.24 (brs, 1H), 7.18-7.91 (m, 8H), 8.69 (s, 1H) |
| 114 | 2.73 (t, 2H), 3.75 (q, 2H), 5.83 (brs, 1H), 7.18-7.75 (m, 13H), 8.62 (s, 1H) |

TABLE 2-8

| Compound No. | δ value (ppm, solvent: CDCl₃, internal standard substance: TMS) |
|---|---|
| 115 | 3.70 (t, 2H), 3.55 (q, 2H), 3.92 (s, 3H), 6.10 (brs, 1H), 6.82-7.40 (m, 8H), 8.23 (s, 1H) |
| 116 | 2.45 (s, 3H), 2.86 (t, 2H), 3.92 (q, 2H), 6.27 (brs, 1H), 7.17-7.83 (m, 8H), 8.68 (s, 1H) |
| 117 | 2.47 (s, 3H), 2.86 (t, 2H), 3.91 (q, 2H), 6.18 (brs, 1H), 7.09-7.81 (m, 8H), 8.68 (s, 1H) |
| 118 | 1.40 (t, 3H), 2.84 (t, 2H), 3.87-4.06 (m, 4H), 6.20 (brs, 1H), 6.75-7.80 (m, 8H), 8.68 (s, 1H) |
| 119 | 1.30 (d, 6H), 3.84 (t, 2H), 3.90 (q, 2H), 4.55 (m, 1H), 6.43 (brs, 1H), 6.78-7.82 (m, 8H), 8.67 (s, 1H) |
| 120 | 2.98 (t, 2H), 3.04 (s, 3H), 3.93 (q, 2H), 7.44-7.92 (m, 8H), 8.69 (s, 1H) |
| 121 | 2.84 (t, 2H), 3.46 (s, 3H), 3.87 (q, 2H), 5.16 (s, 2H), 6.22 (d, 1H), 6.95 (d, 2H), 7.28-7.83 (m, 8H), 8.68 (s, 1H) |
| 122 | 2.70 (s, 6H), 2.92 (t, 2H), 3.94 (q, 2H), 6.40 (brs, 1H), 7.44-7.93 (m, 8H), 8.69 (s, 1H) |
| 123 | 2.02 (s, 1H), 2.82 (t, 2H), 3.00 (s, 3H), 3.88 (q, 2H), 6.14 (brs, 1H), 7.07-7.90 (m, 8H), 8.66 (s, 1H) |
| 124 | 2.80 (s, 3H), 2.86 (t, 2H), 3.26 (s, 3H), 3.90 (q, 2H), 6.64 (brs, 1H), 7.22-7.88 (m, 8H), 8.68 (s, 1H) |
| 125 | 2.72 (t, 2H), 3.74 (s, 6H), 3.82 (q, 2H), 7.37-7.97 (m, 8H), 8.53 (s, 1H) |
| 126 | 2.85 (s, 3H), 2.92 (t, 2H), 3.90 (q, 2H), 6.04 (brs, 1H), 7.31-7.80 (m, 9H), 8.64 (s, 1H) |
| 127 | 2.83 (t, 2H), 4.00 (q, 2H), 5.78 (brs, 1H), 7.35-8.08 (m, 8H), 8.37 (s, 1H) |
| 128 | 2.60 (s, 3H), 2.91 (t, 2H), 3.92 (q, 2H), 6.37 (brs, 1H), 7.20-7.87 (m, 8H), 8.58 (s, 1H) |
| 129 | 1.37 (t, 3H), 2.89 (t, 2H), 3.94 (q, 2H), 4.37 (q, 2H), 6.07 (brs, 1H), 7.38-7.98 (m, 8H), 8.65 (s, 1H) |
| 130 | 2.86 (t, 2H), 3.93 (q, 2H), 4.79 (s, 2H), 6.73 (brs, 1H), 7.18-7.90 (m, 8H), 8.60 (s, 1H) |

TABLE 2-9

| Compound No. | δ value (ppm, solvent: CDCl₃, internal standard substance: TMS) |
|---|---|
| 131 | 2.17 (brs, 1H), 2.79 (t, 2H), 3.84 (q, 2H), 4.55 (s, 2H), 6.17 (brs, 1H), 7.13-7.34 (m, 8H), 8.57 (s, 1H) |
| 132 | 2.87 (t, 2H), 3.93 (q, 2H), 4.68 (d, 2H), 6.15 (brs, 1H), 7.26-7.85 (m, 8H), 8.67 (s, 1H) |
| 133 | 2.92 (t, 2H), 3.32 (s, 3H), 4.03 (q, 2H), 4.58 (s, 2H), 7.16-7.81 (m, 7H), 8.27-8.35 (m, 2H) |
| 134 | 2.92 (t, 2H), 3.94 (q, 2H), 5.02 (s, 2H), 6.23 (t, 1H), 6.43 (brs, 1H), 7.22-7.91 (m, 8H), 8.69 (s, 1H) |
| 135 | 2.93 (t, 2H), 3.36 (s, 3H), 4.00 (t, 2H), 4.39 (s, 2H), 7.20-8.12 (m, 8H), 8.65 (s, 1H) |
| 136 | 2.85 (t, 2H), 3.37 (s, 3H), 3.83 (q, 2H), 4.41 (s, 2H), 6.84 (brs, 1H), 7.18-7.88 (m, 8H), 8.69 (s, 1H) |
| 137 | 1.40 (d, 3H), 2.91 (t, 2H), 3.20 (s, 3H), 3.95 (q, 2H), 4.71 (q, 1H), 6.85 (brs, 1H), 7.10-7.92 (m, 8H), 8.70 (brs, 1H) |
| 138 | 2.88 (t, 2H), 3.88 (t, 2H), 5.58 (q, 1H), 7.25-7.85 (m, 9H), 8.54 (s, 1H) |
| 139 | 2.95 (t, 2H), 3.36 (s, 3H), 3.97 (brs, 2H), 4.54 (s, 2H), 6.79-7.84 (m, 8H), 8.24 (brs, 1H) |
| 140 | 2.88 (t, 2H), 3.36 (s, 3H), 3.98 (q, 2H), 4.54 (s, 2H), 6.32 (brs, 1H), 7.22-8.01 (m, 7H), 8.68 (s, 1H) |
| 141 | 2.93 (t, 2H), 3.36 (s, 3H), 3.96 (q, 2H), 4.57 (s, 2H), 6.50 (brs, 1H), 6.98-7.80 (m, 7H), 8.69 (brs, 1H) |
| 142 | 2.88 (t, 2H), 3.33 (s, 3H), 3.94 (q, 2H), 4.52 (s, 2H), 6.71 (brs, 1H), 6.96-7.90 (m, 7H), 8.68 (s, 1H) |
| 143 | 2.88 (t, 2H), 3.33 (s, 3H), 3.94 (q, 2H), 4.53 (s, 2H), 6.58 (brs, 1H), 7.27-8.01 (m, 7H), 8.67 (s, 1H) |
| 144 | 2.31 (s, 3H), 2.88 (t, 2H), 3.33 (s, 3H), 3.95 (q, 2H), 4.56 (s, 2H), 6.62 (brs, 1H), 7.14-8.01 (m, 7H), 8.67 (s, 1H) |
| 145 | 2.35 (s, 3H), 2.87 (t, 2H), 3.35 (s, 3H), 3.96 (q, 2H), 4.56 (s, 2H), 6.51 (brs, 1H), 6.99-7.87 (m, 7H), 8.67 (s, 1H) |
| 146 | 2.85 (t, 2H), 3.35 (s, 3H), 3.94 (q, 2H), 4.88 (s, 2H), 6.28 (brs, 1H), 7.08-7.82 (m, 6H), 8.70 (s, 1H) |

TABLE 2-10

| Compound No. | δ value (ppm, solvent: CDCl₃, internal standard substance: TMS) |
|---|---|
| 147 | 2.95 (t, 2H), 3.81 (s, 2H), 3.95 (q, 2H), 6.54 (brs, 1H), 7.15-7.79 (m, 8H), 8.67 (s, 1H) |
| 148 | 2.89 (t, 2H), 3.42 (s, 3H), 3.93 (q, 2H), 4.70 (s, 2H), 4.76 (s, 2H), 6.84 (brs, 1H), 7.18-7.90 (m, 8H), 8.68 (s, 1H) |
| 149 | 2.84 (t, 2H), 3.32 (s, 6H), 3.98 (q, 2H), 5.76 (s, 1H), 6.67 (brs, 1H), 7.13-8.00 (m, 8H), 8.67 (s, 1H) |
| 150 | 1.24 (t, 5H), 2.92 (t, 2H), 3.44 (q, 4H), 3.96 (q, 2H), 5.82 (s, 1H), 6.66 (brs, 1H), 7.10-7.97 (m, 8H), 8.67 (s, 1H) |
| 151 | 1.24 (t, 6H), 2.88 (t, 2H), 3.58 (q, 2H), 3.92 (q, 2H), 5.48 (s, 1H), 6.10 (brs, 1H), 7.34-8.02 (m, 8H), 8.69 (s, 1H) |
| 152 | 2.01 (s, 3H), 2.91 (t, 2H), 3.83 (s, 2H), 3.96 (q, 2H), 6.42 (brs, 1H), 7.25-7.83 (m, 8H), 8.68 (s, 1H) |
| 153 | 1.21 (t, 3H), 2.88 (t, 2H), 3.48 (q, 2H), 3.93 (q, 2H), 4.63 (s, 2H), 6.76 (brs, 1H), 7.17-7.94 (m, 8H), 8.68 (s, 1H) |
| 154 | 1.18 (d, 6H), 2.88 (t, 2H), 3.49-3.76 (m, 1H), 3.95 (q, 2H), 4.64 (s, 2H), 6.61 (brs, 1H), 7.18-7.81 (m, 8H), 8.68 (s, 1H) |
| 155 | 2.84 (t, 2H), 3.95 (q, 2H), 3.98-4.08 (m, 4H), 6.23 (s, 1H), 6.55 (brs, 1H), 7.24-7.98 (m, 8H), 8.66 (s, 1H) |
| 156 | 1.61-2.01 (m, 6H), 2.84 (t, 2H), 3.60 (m, 2H), 3.90 (q, 2H), 5.40 (s, 1H), 6.23 (brs, 1H), 6.91-7.90 (m, 8H), 8.68 (s, 1H) |
| 157 | 2.84 (t, 2H), 3.13 (t, 2H), 3.87 (q, 2H), 4.54 (t, 2H), 6.68 (d, 1H), 7.12-7.86 (m, 7H), 8.69 (s, 1H) |
| 158 | 2.88-3.15 (m, 4H), 3.86-4.01 (m, 4H), 4.40 (brs, 1H), 7.08-8.13 (m, 9H), 8.61 (s, 1H) |
| 159 | 2.87 (t, 2H), 2.94 (s, 6H), 3.88 (q, 2H), 6.60 (d, 1H), 7.22-7.79 (m, 8H), 8.67 (s, 1H) |
| 160 | 2.04 (s, 3H), 2.88 (t, 2H), 3.95 (q, 2H), 6.21 (brs, 1H), 6.93-7.84 (m, 8H), 8.22 (brs, 1H), 8.68 (s, 1H) |
| 161 | 2.77 (s, 6H), 2.83 (t, 2H), 3.97 (q, 2H), 7.15 (brs, 1H), 7.39-8.19 (m, 8H), 8.64 (s, 1H) |
| 162 | 2.80 (s, 3H), 2.84 (t, 2H), 3.87 (q, 2H), 4.35 (s, 2H), 6.22 (d, 1H), 7.30-7.88 (m, 8H), 8.66 (s, 1H) |

TABLE 2-11

| Compound No. | δ value (ppm, solvent: CDCl₃, internal standard substance: TMS) |
|---|---|
| 163 | 2.91 (t, 2H), 3.95 (q, 2H), 6.10 (brs, 1H), 6.91-7.84 (m, 7H), 8.69 (s, 1H) |
| 164 | 2.90 (t, 2H), 3.94 (q, 2H), 6.10 (brs, 1H), 7.00-7.83 (m, 7H), 8.68 (s, 1H) |
| 165 | 2.92 (t, 2H), 3.95 (q, 2H), 6.57 (brs, 1H), 7.20-7.90 (m, 7H), 8.67 (s, 1H) |
| 166 | 2.86 (t, 2H), 3.89 (q, 2H), 6.05 (brs, 1H), 7.00-7.84 (m, 7H), 8.68 (s, 1H) |
| 167 | 2.35 (s, 3H), 3.00 (t, 2H), 4.02 (q, 2H), 6.23 (brs, 1H), 7.04-8.27 (m, 7H), 8.71 (s, 1H) |
| 168 | 2.91 (t, 2H), 3.96 (q, 2H), 6.10 (brs, 1H), 7.07-7.83 (m, 7H), 8.68 (s, 1H) |
| 169 | 2.88 (t, 2H), 3.94 (q, 2H), 6.33 (brs, 1H), 7.05-7.79 (m, 7H), 8.67 (s, 1H) |
| 170 | 2.90 (t, 2H), 3.95 (q, 2H), 7.37-7.83 (m, 7H), 8.68 (s, 1H) |
| 171 | 2.93 (t, 2H), 3.97 (q, 2H), 6.10 (brs, 1H), 7.03-7.84 (m, 7H), 8.67 (s, 1H) |
| 172 | 2.92 (t, 2H), 3.95 (q, 2H), 6.10 (brs, 1H), 7.13-7.81 (m, 7H), 8.68 (s, 1H) |
| 173 | 2.92 (t, 2H), 3.93 (q, 2H), 6.10 (brs, 1H), 7.28-7.81 (m, 7H), 8.68 (s, 1H) |
| 174 | 2.97 (t, 2H), 4.00 (q, 2H), 6.22 (brs, 1H), 7.05-7.83 (m, 7H), 8.68 (s, 1H) |
| 175 | 2.87 (t, 2H), 3.92 (q, 2H), 6.05 (brs, 1H), 7.13-7.84 (m, 7H), 8.69 (s, 1H) |
| 176 | 2.95 (t, 2H), 4.01 (q, 2H), 6.12 (brs, 1H), 7.18-7.82 (m, 7H), 8.69 (s, 1H) |
| 177 | 2.90 (t, 2H), 3.94 (q, 2H), 6.27 (brs, 1H), 7.19-7.84 (m, 7H), 8.69 (s, 1H) |

TABLE 2-11-continued

| Compound No. | δ value (ppm, solvent: CDCl₃, internal standard substance: TMS) |
|---|---|
| 178 | 2.93 (t, 2H), 3.92 (s, 3H), 4.00 (q, 2H), 6.55 (brs, 1H), 7.12-7.75 (m, 7H), 8.66 (s, 1H) |

TABLE 2-12

| Compound No. | δ value (ppm, solvent: CDCl₃, internal standard substance: TMS) |
|---|---|
| 179 | 2.93 (t, 2H), 4.00 (q, 2H), 6.55 (brs, 1H), 7.16-7.79 (m, 7H), 8.60 (s, 1H) |
| 180 | 2.31 (s, 3H), 2.36 (s, 3H), 2.90 (t, 2H), 3.93 (q, 2H), 6.89-7.83 (m, 7H), 8.68 (s, 1H) |
| 181 | 2.15 (s, 3H), 2.35 (s, 6H), 2.94 (t, 2H), 3.92 (q, 2H), 6.84 (brs, 1H), 6.84-8.00 (m, 6H), 8.67 (s, 1H) |
| 182 | 2.99 (t, 2H), 4.00 (q, 2H), 7.37-8.15 (m, 8H), 8.66 (s, 1H) |
| 183 | 2.88 (t, 2H), 3.87 (q, 2H), 6.10 (brs, 1H), 6.87-7.84 (m, 11H), 8.68 (s, 1H) |
| 184 | 2.91 (t, 2H), 3.88 (q, 2H), 3.92 (s, 3H), 6.10 (brs, 1H), 7.09-7.84 (m, 10H), 8.69 (s, 1H) |
| 185 | 2.88 (t, 2H), 3.38 (s, 3H), 4.04 (q, 2H), 4.81 (s, 2H), 6.62 (brs, 1H), 7.37-8.30 (m, 10H), 8.70 (s, 1H) |
| 186 | 2.33 (s, 3H), 2.86 (t, 2H), 3.92 (q, 2H), 6.81-7.93 (m, 13H), 8.67 (s, 1H) |
| 187 | 2.96 (t, 2H), 4.08 (q, 2H), 6.97 (brs, 1H), 7.40-7.94 (m, 6H), 8.47-8.64 (m, 2H) |
| 188 | 3.62 (t, 2H), 3.90 (q, 2H), 6.80 (brs, 1H), 7.38-8.27 (m, 10H), 8.89 (s, 1H) |
| 189 | 2.95 (t, 2H), 3.74 (q, 2H), 7.02-8.58 (m, 12H) |
| 190 | 2.94 (t, 2H), 4.00 (q, 2H), 6.09 (brs, 1H), 7.29-8.15 (m, 9H), 8.71 (s, 1H), 8.92 (d, 1H) |
| 191 | 3.04 (t, 2H), 4.00 (q, 2H), 6.12 (brs, 1H), 7.21-8.88 (m, 10H) |
| 192 | 3.06 (t, 2H), 4.06 (q, 2H), 6.14 (brs, 1H), 7.38-8.14 (m, 8H), 8.64 (s, 1H), 8.72 (s, 1H), 9.16 (s, 1H) |
| 193 | 2.80 (t, 2H), 3.83 (q, 2H), 6.04 (brs, 1H), 7.25-8.44 (m, 7H), 8.69 (s, 1H) |
| 194 | 2.89 (t, 2H), 3.85 (q, 2H), 6.02 (brs, 1H), 6.79-8.26 (m, 7H), 8.69 (s, 1H) |
| 195 | 2.95 (t, 2H), 3.96 (q, 2H), 7.47-7.84 (m, 6H), 8.23-8.35 (m, 1H), 8.69 (s, 1H) |

TABLE 2-13

| Compound No. | δ value (ppm, solvent: CDCl₃, internal standard substance: TMS) |
|---|---|
| 196 | 2.85 (t, 2H), 3.88 (q, 2H), 6.06 (brs, 1H), 7.11-7.93 (m, 6H), 8.30 (d, 1H), 8.69 (s, 1H) |
| 197 | 2.95 (t, 2H), 3.92 (q, 2H), 6.15 (brs, 1H), 7.30-7.90 (m, 6H), 8.68 (s, 1H), 8.80 (s, 1H) |
| 198 | 2.92 (t, 2H), 3.95 (q, 2H), 6.05 (brs, 1H), 7.44-7.85 (m, 7H), 8.67 (s, 1H) |
| 199 | 2.81 (t, 2H), 3.88 (q, 2H), 3.90 (q, 2H), 6.28 (brs, 1H), 6.72-6.84 (m, 2H), 7.25-8.13 (m, 5H), 8.68 (s, 1H) |
| 200 | 2.54 (s, 3H), 2.90 (t, 2H), 3.95 (q, 2H), 7.03-8.03 (m, 8H), 8.66 (s, 1H) |
| 201 | 2.85 (t, 2H), 3.82 (q, 2H), 4.52 (d, 2H), 5.32 (t, 1H), 7.28-7.87 (m, 5H), 8.25 (d, 1H), 8.52 (s, 1H), 8.65 (s, 1H) |
| 202 | 2.92 (t, 2H), 3.40 (t, 1H), 3.95 (q, 2H), 4.75 (d, 2H), 6.03 (brs, 1H), 7.47-7.84 (m, 6H), 8.57 (s, 1H), 8.69 (s, 1H) |
| 203 | 2.82 (t, 2H), 3.50 (s, 3H), 3.86 (t, 2H), 6.48 (d, 1H), 7.23-7.98 (m, 5H), 8.58 (s, 1H) |
| 204 | 2.86 (t, 2H), 3.92 (q, 2H), 6.10 (brs, 1H), 6.90-7.93 (m, 7H), 8.68 (s, 1H) |
| 205 | 2.80 (t, 2H), 3.85 (q, 2H), 6.23 (brs, 1H), 7.02-7.38 (m, 7H), 8.52 (s, 1H) |
| 206 | 2.44 (s, 3H), 2.88 (t, 2H), 3.91 (q, 2H), 6.55-6.90 (m, 3H), 7.26-7.91 (m, 4H), 8.68 (s, 1H) |

TABLE 2-13-continued

| Compound No. | δ value (ppm, solvent: CDCl₃, internal standard substance: TMS) |
|---|---|
| 207 | 2.90 (t, 2H), 3.29 (s, 3H), 3.90 (q, 2H), 4.45 (s, 2H), 6.85 (brs, 1H), 6.97 (d, 1H), 7.13 (d, 1H), 7.39-7.84 (m, 4H), 8.68 (s, 1H) |
| 208 | 2.26 (s, 3H), 2.92 (t, 2H), 3.90 (q, 2H), 6.13 (brs, 1H), 6.80 (d, 1H), 7.08 (d, 1H), 7.38-7.91 (m, 4H), 8.68 (s, 1H) |
| 209 | 2.83 (t, 2H), 3.90 (q, 2H), 4.57 (s, 2H), 6.10 (brs, 1H), 7.46-7.83 (m, 6H), 8.67 (s, 1H) |
| 210 | 2.90 (t, 2H), 3.94 (q, 2H), 6.27 (brs, 1H), 7.26-7.82 (m, 5H), 8.67 (s, 1H), 8.74 (d, 1H) |
| 211 | 2.67 (s, 3H), 2.90 (t, 2H), 3.84 (q, 2H), 6.07 (brs, 1H), 7.25 (s, 1H), 7.46-7.84 (m, 4H), 8.67 (s, 1H) |

TABLE 2-14

| Compound No. | δ value (ppm, solvent: CDCl₃, internal standard substance: TMS) |
|---|---|
| 212 | 2.87 (t, 2H), 3.91 (q, 2H), 4.06 (s, 3H), 6.25 (brs, 1H), 7.17 (s, 1H), 7.38-7.91 (m, 4H), 8.68 (s, 1H) |
| 213 | 1.33 (t, 3H), 2.94 (t, 2H), 3.92 (q, 2H), 4.35 (q, 2H), 5.62 (brs, 1H), 7.20-7.35 (m, 2H), 8.32 (s, 1H), 8.53 (s, 1H) |
| 214 | 1.34 (t, 3H), 2.71 (s, 3H), 2.93 (t, 2H), 3.89 (q, 2H), 4.34 (q, 2H), 5.60 (brs, 1H), 7.13-7.34 (m, 2H), 8.52 (s, 1H) |
| 215 | 2.79 (t, 2H), 3.80 (s, 3H), 3.84 (q, 2H), 6.44 (brs, 1H), 6.81-7.83 (m, 9H), 8.64 (s, 1H) |
| 216 | 2.79 (t, 2H), 3.74 (s, 3H), 3.82 (q, 2H), 6.69-7.83 (m, 9H), 8.65 (s, 1H) |
| 217 | 2.80 (t, 2H), 3.77 (s, 3H), 3.83 (q, 2H), 6.81-7.88 (m, 9H), 8.64 (s, 1H) |
| 218 | 2.82 (t, 2H), 3.87 (q, 2H), 6.23 (brs, 1H), 6.92 (s, 1H), 7.25-7.89 (m, 8H), 8.65 (s, 1H) |
| 219 | 2.81 (t, 2H), 3.85 (q, 2H), 6.86 (brs, 1H), 6.91 (s, 1H), 7.25-7.88 (m, 8H), 8.66 (s, 1H) |
| 220 | 2.83 (t, 2H), 3.87 (q, 2H), 6.55 (brs, 1H), 6.93 (s, 1H), 7.27-7.88 (m, 8H), 8.66 (s, 1H) |
| 221 | 2.79 (t, 2H), 3.71 (q, 2H), 7.41-8.24 (m, 9H), 8.50 (s, 1H) |
| 222 | 2.82 (t, 2H), 3.85 (q, 2H), 6.93 (s, 1H), 7.17-7.88 (m, 8H), 8.65 (s, 1H) |
| 223 | 2.84 (t, 2H), 3.88 (q, 2H), 6.44 (brs, 1H), 6.97 (s, 1H), 7.27-7.81 (m, 9H), 8.66 (s, 1H) |
| 224 | 2.74 (t, 2H), 3.77 (q, 2H), 6.85-7.85 (m, 9H), 8.63 (s, 1H) |
| 225 | 2.83 (t, 2H), 3.88 (q, 2H), 6.32 (brs, 1H), 6.90-7.89 (m, 9H), 8.66 (s, 1H) |
| 226 | 2.81 (t, 2H), 3.85 (q, 2H), 6.65 (brs, 1H), 6.85-7.88 (m, 9H), 8.66 (s, 1H) |
| 227 | 2.78 (t, 2H), 3.82 (q, 2H), 6.84 (s, 1H), 7.26-7.87 (m, 9H), 8.65 (s, 1H) |
| 228 | 1.65-1.76 (m, 6H), 2.85 (t, 2H), 3.36-3.46 (m, 4H), 3.90 (q, 2H), 6.28 (brs, 1H), 6.27 (s, 1H), 7.25-8.00 (m, 4H), 8.65 (s, 1H) |

TABLE 2-15

| Compound No. | δ value (ppm, solvent: CDCl₃, internal standard substance: TMS) |
|---|---|
| 229 | 1.48 (d, 3H), 2.81 (dd, 2H), 4.62-4.79 (m, 1H), 5.43 (d, 1H), 7.10-7.40 (m, 7H), 8.49 (s, 1H) |
| 230 | 1.45 (d, 3H), 2.80 (d, 2H), 4.55-4.83 (m, 1H), 5.36 (d, 1H), 6.85-7.46 (m, 6H), 8.52 (s, 1H) |
| 231 | 1.50 (d, 3H), 2.87 (dd, 2H), 4.64-4.91 (m, 1H), 5.58 (d, 1H), 7.06-7.48 (m, 6H), 8.51 (s, 1H) |
| 232 | 1.46 (d, 3H), 2.81 (dd, 2H), 4.58-4.85 (m, 1H), 5.40 (d, 1H), 7.11-7.31 (m, 6H), 8.52 (s, 1H) |
| 233 | 1.48 (d, 3H), 2.90 (dd, 2H), 4.63-4.92 (m, 1H), 5.35 (d, 1H), 7.06-7.74 (m, 6H), 8.50 (s, 1H) |

TABLE 2-15-continued

| Compound No. | δ value (ppm, solvent: CDCl₃, internal standard substance: TMS) |
|---|---|
| 234 | 1.50 (d, 3H), 2.84 (d, 2H), 4.63-4.78 (m, 1H), 5.33 (d, 1H), 7.12-7.62 (m, 6H), 8.53 (s, 1H) |
| 235 | 1.48 (d, 3H), 2.85 (d, 2H), 4.58-4.86 (m, 1H), 5.41 (d, 1H), 7.12-7.67 (m, 6H), 8.53 (s, 1H) |
| 236 | 1.54 (d, 3H), 2.84 (dd, 2H), 3.86 (s, 3H), 4.65-4.90 (m, 1H), 5.58 (brs, 1H), 6.80-7.42 (m, 6H), 8.50 (s, 1H) |
| 237 | 1.47 (d, 3H), 2.62 (dd, 2H), 3.09 (s, 3H), 4.83-4.93 (m, 1H), 6.40 (d, 1H), 7.23-7.64 (m, 4H), 8.04-8.15 (m, 1H), 8.53 (s, 1H) |
| 238 | 1.48 (d, 3H), 2.85 (d, 2H), 4.64-4.80 (m, 1H), 5.15 (brs, 1H), 7.10-7.73 (m, 6H), 8.52 (s, 1H) |
| 239 | 1.48 (d, 3H), 2.40 (s, 3H), 2.86 (dd, 2H), 4.64-4.80 (m, 1H), 5.48 (d, 1H), 7.05-7.42 (m, 6H), 8.52 (s, 1H) |
| 240 | 1.20 (t, 3H), 1.47 (d, 3H), 2.60 (q, 2H), 2.85 (dd, 2H), 4.56-4.83 (m, 1H), 5.38 (brs, 1H), 6.99-7.36 (m, 6H), 8.51 (s, 1H) |
| 241 | 1.24 (d, 6H), 1.47 (d, 3H), 2.77-2.97 (m, 3H), 4.62-4.77 (m, 1H), 5.40 (d, 1H), 7.10-7.37 (m, 6H), 8.51 (s, 1H) |
| 242 | 1.30 (dd, 6H), 1.52 (d, 3H), 4.45-4.89 (m, 2H), 5.67 (d, 1H), 6.78-7.42 (m, 6H), 8.50 (s, 1H) |
| 243 | 1.36 (d, 3H), 2.57-3.15 (m, 3H), 4.63-4.79 (m, 3H), 5.90 (d, 1H), 7.13-7.46 (m, 6H), 8.46 (s, 1H) |
| 244 | 1.49 (d, 3H), 2.83 (dd, 2H), 3.71 (s, 1H), 4.60-4.87 (m, 1H), 4.75 (s, 2H), 6.13 (d, 1H), 6.78-7.56 (m, 5H), 8.44 (s, 1H) |

TABLE 2-16

| Compound No. | δ value (ppm, solvent: CDCl₃, internal standard substance: TMS) |
|---|---|
| 245 | 1.49 (d, 3H), 2.90 (dd, 2H), 4.64-4.82 (m, 1H), 4.73 (s, 2H), 6.25 (d, 1H), 7.10-7.42 (m, 5H), 8.46 (s, 1H) |
| 246 | 1.48 (d, 3H), 2.38 (s, 3H), 2.85 (dd, 2H), 4.63-4.79 (m, 1H), 5.40 (d, 1H), 6.69-7.39 (m, 5H), 8.51 (s, 1H) |
| 247 | 1.51 (d, 3H), 2.89 (dd, 2H), 4.63-4.90 (m, 1H), 5.46 (d, 1H), 6.82-7.49 (m, 5H), 8.51 (s, 1H) |
| 248 | 1.48 (d, 3H), 2.89 (dd, 2H), 4.71-4.84 (m, 1H), 5.40 (d, 1H), 6.93-7.72 (m, 5H), 8.51 (s, 1H) |
| 249 | 1.48 (d, 3H), 2.88 (dd, 2H), 4.67-4.83 (m, 1H), 5.30 (brs, 1H), 7.09-7.61 (m, 5H), 8.51 (s, 1H) |
| 250 | 1.48 (d, 3H), 2.35 (s, 3H), 2.86 (dd, 2H), 4.63-4.79 (m, 1H), 5.41 (d, 1H), 7.01-7.31 (m, 5H), 8.52 (s, 1H) |
| 251 | 1.50 (d, 3H), 2.94 (dd, 2H), 4.68-4.95 (m, 1H), 5.60 (d, 1H), 7.04-7.52 (m, 5H), 8.51 (s, 1H) |
| 252 | 1.50 (d, 3H), 2.96 (dd, 2H), 4.67-4.94 (m, 1H), 5.53 (d, 1H), 7.11-7.63 (m, 5H), 8.51 (s, 1H) |
| 253 | 1.51 (d, 3H), 2.88 (dd, 2H), 4.64-4.91 (m, 1H), 5.32 (d, 1H), 7.10-7.81 (m, 5H), 8.52 (s, 1H) |
| 254 | 1.50 (d, 3H), 2.85 (dd, 2H), 4.64-4.72 (m, 1H), 5.74 (d, 1H), 7.29-7.66 (m, 5H), 8.51 (s, 1H) |
| 255 | 1.50 (d, 3H), 2.33 (s, 3H), 2.85 (dd, 2H), 4.67-4.84 (m, 1H), 5.51 (d, 1H), 6.95-7.44 (m, 5H), 8.50 (s, 1H) |
| 256 | 1.52 (d, 3H), 2.92 (dd, 2H), 3.06 (s, 3H), 4.71-4.87 (m, 1H), 5.33 (d, 1H), 7.10-7.99 (m, 5H), 8.52 (s, 1H) |
| 257 | 1.52 (d, 3H), 2.87 (dd, 2H), 4.70-4.86 (m, 1H), 5.56 (d, 1H), 7.13-7.65 (m, 5H), 8.52 (s, 1H) |
| 258 | 1.46 (d, 3H), 2.87 (dd, 2H), 4.70-4.83 (m, 1H), 5.32 (d, 1H), 7.09-7.63 (m, 5H), 8.51 (s, 1H) |
| 259 | 1.48 (d, 3H), 2.30 (s, 3H), 2.36 (s, 3H), 2.85 (dd, 2H), 4.63-4.79 (m, 1H), 5.42 (d, 1H), 6.88-7.30 (m, 5H), 8.51 (s, 1H) |
| 260 | 1.48 (d, 3H), 2.92 (dd, 2H), 4.69-4.83 (m, 1H), 5.28 (d, 1H), 7.09-7.92 (m, 5H), 8.51 (s, 1H) |

TABLE 2-17

| Compound No. | δ value (ppm, solvent: CDCl$_3$, internal standard substance: TMS) |
|---|---|
| 261 | 1.52 (d, 3H), 2.94 (dd, 2H), 4.66-4.93 (m, 1H), 5.62 (d, 1H), 7.05-7.31 (m, 4H), 8.51 (s, 1H) |
| 262 | 1.53 (d, 3H), 3.00 (dd, 2H), 4.65-4.95 (m, 1H), 5.40 (d, 1H), 7.00-7.58 (m, 4H), 8.52 (s, 1H) |
| 263 | 1.50 (d, 3H), 2.15 (s, 3H), 2.35 (s, 6H), 2.91 (t, 2H), 4.60-4.90 (m, 1H), 5.32 (brs, 1H), 6.85-7.30 (m, 4H), 8.51 (s, 1H) |
| 264 | 1.49 (d, 3H), 2.92 (dd, 2H), 4.71-4.86 (m, 1H), 5.57 (d, 1H), 7.15-7.42 (m, 3H), 7.92-8.01 (m, 1H), 8.50 (s, 1H), 8.68-8.74 (m, 1H) |
| 265 | 1.47 (d, 3H), 2.90 (dd, 2H), 4.66-4.80 (m, 1H), 5.33 (brs, 1H), 7.19-7.31 (m, 3H), 7.76-7.82 (m, 1H), 8.51 (s, 1H) |
| 266 | 1.47 (d, 3H), 2.67 (s, 3H), 2.86 (dd, 2H), 4.67-4.82 (m, 1H), 5.70 (brs, 1H), 7.19 (s, 1H), 7.37-7.81 (m, 4H), 8.67 (s, 1H) |
| 267 | 1.05 (t, 3H), 1.70-1.95 (m, 2H), 2.82 (dd, 2H), 4.49-4.59 (m, 1H), 5.42 (d, 2H), 7.05-7.41 (m, 7H), 8.50 (s, 1H) |
| 268 | 0.98 (t, 3H), 1.17-2.07 (m, 4H), 2.82 (dd, 2H), 4.52-4.74 (m, 1H), 5.42 (d, 1H), 7.12-7.43 (m, 7H), 8.51 (s, 1H) |
| 269 | 0.86-0.99 (m, 3H), 1.17-1.47 (m, 4H), 1.64-1.85 (m, 2H), 2.82 (dd, 2H), 4.49-4.71 (m, 1H), 5.31 (d, 1H), 7.11-7.46 (m, 7H), 8.50 (s, 1H) |
| 270 | 1.60 (d, 3H), 2.85 (dd, 2H), 4.63-4.85 (m, 1H), 5.83 (brs, 1H), 7.20-7.83 (m, 9H), 8.67 (s, 1H) |
| 271 | 1.48 (d, 3H), 2.85 (dd, 2H), 4.62-4.88 (m, 1H), 6.80 (brs, 1H), 6.86-7.88 (m, 8H), 8.66 (s, 1H) |
| 272 | 1.58 (d, 3H), 2.90 (dd, 2H), 4.74-4.91 (m, 1H), 6.00 (brs, 1H), 7.03-7.89 (m, 8H), 8.61 (s, 1H) |
| 273 | 1.48 (d, 3H), 2.85 (dd, 2H), 4.61-4.86 (m, 1H), 6.78 (brs, 1H), 7.14-7.84 (m, 8H), 8.67 (s, 1H) |
| 274 | 1.51 (d, 3H), 2.91 (dd, 2H), 4.80 (brs, 1H), 5.82 (brs, 1H), 7.16-7.81 (m, 8H), 8.66 (s, 1H) |
| 275 | 1.52 (d, 3H), 2.85 (dd, 2H), 4.64-4.83 (m, 1H), 6.80 (d, 1H), 7.31-7.81 (m, 8H), 8.68 (s, 1H) |

TABLE 2-18

| Compound No. | δ value (ppm, solvent: CDCl$_3$, internal standard substance: TMS) |
|---|---|
| 276 | 1.52 (d, 3H), 2.90 (dd, 2H), 4.83 (s, 3H), 4.62-4.95 (m, 1H), 6.15 (brs, 1H), 6.82-7.82 (m, 8H), 8.68 (s, 1H) |
| 277 | 1.52 (t, 3H), 2.88 (d, 2H), 4.55-4.92 (m, 1H), 5.84 (d, 1H), 7.37-7.91 (m, 8H), 8.69 (s, 1H) |
| 278 | 1.48 (d, 3H), 2.90 (dd, 2H), 3.33 (s, 3H), 4.60 (s, 2H), 4.74-4.92 (m, 1H), 6.34 (d, 1H), 7.19-7.90 (m, 8H), 8.67 (s, 1H) |
| 279 | 1.50 (d, 3H), 2.32 (s, 3H), 2.80 (dd, 2H), 4.52-4.85 (m, 1H), 6.78 (d, 2H), 7.06-7.82 (m, 8H), 8.66 (s, 1H) |
| 280 | 1.25 (d, 3H), 2.52 (dd, 2H), 3.86-4.08 (m, 1H), 6.81 (s, 1H), 7.26-7.99 (m, 7H), 8.50 (s, 1H) |
| 281 | 1.60 (d, 3H), 3.00 (dd, 2H), 4.85-5.00 (m, 1H), 7.19-8.25 (m, 8H), 8.65 (s, 1H) |
| 282 | 1.58 (d, 3H), 2.97 (dd, 2H), 4.71-5.00 (m, 1H), 6.52 (d, 1H), 7.26-7.97 (m, 8H), 8.59 (s, 1H) |
| 283 | 1.60 (d, 3H), 3.00 (dd, 2H), 4.75-5.08 (m, 1H), 7.26-8.43 (m, 8H), 8.64 (s, 1H) |
| 284 | 1.62 (d, 3H), 3.00 (d, 2H), 4.84-4.92 (m, 1H), 7.13-8.62 (m, 9H) |
| 285 | 1.50 (d, 3H), 2.90 (dd, 2H), 4.73-4.87 (m, 1H), 5.92 (d, 1H), 7.27-7.89 (m, 7H), 8.67 (s, 1H) |
| 286 | 1.50 (d, 3H), 2.90 (dd, 2H), 4.67-4.93 (m, 1H), 5.88 (d, 1H), 7.06-7.91 (7H), 8.67 (s, 1H) |
| 287 | 1.57 (d, 3H), 2.93 (dd, 2H), 3.87 (s, 3H), 3.76-5.05 (m, 1H), 6.90-6.85 (m, 8H), 8.70 (s, 1H) |
| 288 | 1.56 (d, 3H), 2.97 (dd, 2H), 4.65-5.02 (m, 1H), 6.93 (d, 1H), 7.36-8.05 (m, 7H), 8.65 (s, 1H) |
| 289 | 1.25 (d, 2H), 1.50 (d, 2H), 2.62-3.19 (m, 3H), 4.74-4.89 (m, 1H), 5.96 (d, 1H), 7.26-7.89 (m, 7H), 8.67 (s, 1H) |

TABLE 2-18-continued

| Compound No. | δ value (ppm, solvent: CDCl$_3$, internal standard substance: TMS) |
|---|---|
| 290 | 1.55 (d, 3H), 2.58-3.38 (m, 2H), 3.05 (s, 3H), 4.72-5.08 (m, 1H), 6.76 (d, 1H), 7.28-8.17 (m, 8H), 8.64 (s, 1H) |
| 291 | 1.53 (d, 3H), 2.90 (d, 2H), 4.65-4.92 (m, 1H), 5.95 (brs, 1H), 7.17-8.00 (m, 6H), 8.62 (s, 1H) |

TABLE 2-19

| Compound No. | δ value (ppm, solvent: CDCl$_3$, internal standard substance: TMS) |
|---|---|
| 292 | 1.43 (d, 3H), 2.67 (s, 3H), 2.86 (dd, 2H), 4.52-4.82 (m, 1H), 5.75 (d, 1H), 7.37-7.81 (m, 5H), 8.67 (s, 1H) |
| 293 | 1.50 (d, 3H), 2.85 (dd, 2H), 4.60-4.80 (m, 1H), 5.82 (brs, 1H), 6.85-7.80 (m, 5H), 8.62 (s, 1H) |
| 294 | 1.07 (t, 3H), 1.74-1.99 (m, 2H), 2.86 (dd, 2H), 4.42-4.78 (m, 1H), 5.94 (d, 1H), 6.87-7.90 (m, 8H), 8.67 (s, 1H) |
| 295 | 1.07 (t, 3H), 1.74-1.98 (m, 2H), 2.91 (dd, 2H), 4.44-4.78 (m, 1H), 5.96 (d, 1H), 7.04-7.91 (m, 7H), 8.67 (s, 1H) |
| 296 | 2.94 (d, 2H), 5.23-5.50 (m, 3H), 5.96-6.27 (m, 2H), 7.22-7.83 (m, 9H), 8.69 (s, 1H) |
| 297 | 2.93 (d, 2H), 5.23-5.50 (m, 3H), 5.96-6.33 (m, 2H), 6.86-7.90 (m, 8H), 8.70 (s, 1H) |
| 298 | 1.06 (d, 3H), 1.13 (d, 3H), 2.00-2.40 (m, 1H), 2.86 (d, 2H), 4.41-4.60 (m, 1H), 5.94 (d, 1H), 7.21-7.90 (m, 9H), 8.66 (s, 1H) |
| 299 | 2.95 (d, 2H), 3.96-4.12 (m, 2H), 4.50-4.68 (m, 1H), 6.70 (d, 1H), 7.02-7.83 (m, 9H), 8.64 (s, 1H) |
| 300 | 2.08 (t, 1H), 2.97 (dd, 2H), 5.73 (m, 1H), 6.42 (d, 1H), 7.01-7.90 (m, 9H), 8.64 (s, 1H) |
| 301 | 3.17 (d, 2H), 5.80 (m, 1H), 6.45 (d, 1H), 7.18-7.82 (m, 14H), 8.66 (s, 1H) |
| 302 | 3.25 (d, 2H), 5.86 (m, 1H), 6.47 (d, 1H), 7.18-7.87 (m, 13H), 8.66 (s, 1H) |
| 303 | 1.34 (t, 3H), 3.23 (dd, 2H), 4.34 (q, 2H), 5.14-5.32 (m, 1H), 6.87 (d, 1H), 7.21-7.93 (m, 9H), 8.67 (s, 1H) |
| 304 | 1.33 (t, 3H), 2.93-3.36 (m, 2H), 4.33 (q, 2H), 5.08-5.38 (m, 1H), 6.69 (d, 1H), 7.26-7.91 (m, 8H), 8.66 (s, 1H) |
| 305 | 2.78-3.42 (m, 2H), 2.84 (d, 3H), 4.92-5.17 (m, 1H), 6.65 (brs, 1H), 6.94 (d, 1H), 7.22-7.90 (m, 9H), 8.67 (s, 1H) |
| 306 | 2.90 (t, 2H), 3.95 (q, 2H), 6.28 (brs, 1H), 7.31-7.69 (m, 7H), 8.71 (s, 1H) |
| 307 | 2.86 (t, 2H), 3.91 (q, 2H), 6.18 (brs, 1H), 7.13-7.88 (m, 7H), 8.79 (s, 1H) |

TABLE 2-20

| Compound No. | δ value (ppm, solvent: CDCl$_3$, internal standard substance: TMS) |
|---|---|
| 308 | 2.89 (t, 2H), 3.95 (q, 2H), 6.10 (brs, 1H), 7.20-7.84 (m, 7H), 8.65 (s, 1H) |
| 309 | 2.86 (t, 2H), 3.91 (q, 2H), 6.05 (brs, 1H), 7.22-7.75 (m, 7H), 8.65 (s, 1H) |
| 310 | 2.91 (t, 2H), 3.93 (q, 2H), 7.19-7.70 (m, 7H), 8.10 (brs, 1H), 8.58 (s, 1H) |
| 311 | 2.87 (t, 2H), 3.50 (s, 3H), 3.96 (q, 2H), 4.60 (s, 2H), 6.59 (brs, 1H), 7.30-7.89 (m, 7H), 8.78 (s, 1H) |
| 312 | 2.86 (t, 2H), 3.35 (s, 3H), 3.94 (q, 2H), 4.60 (s, 2H), 6.58 (brs, 1H), 7.13-7.84 (m, 7H), 8.64 (s, 1H) |
| 313 | 2.91 (t, 2H), 3.38 (s, 3H), 3.94 (q, 2H), 4.60 (s, 2H), 7.12-7.71 (m, 7H), 8.55 (brs, 1H), 8.58 (s, 1H) |
| 314 | 2.89 (t, 2H), 3.36 (s, 3H), 3.94 (q, 2H), 4.60 (s, 2H), 7.12-7.76 (m, 7H), 8.55 (brs, 1H), 8.58 (s, 1H) |
| 315 | 2.87 (t, 2H), 3.35 (s, 3H), 3.96 (q, 2H), 4.60 (s, 2H), 6.60 (brs, 1H), 7.30-7.72 (m, 7H), 8.71 (s, 1H) |
| 316 | 2.86 (t, 2H), 3.35 (s, 3H), 3.96 (q, 2H), 4.60 (s, 2H), 6.53 (brs, 1H), 7.07-7.95 (m, 7H), 8.64 (s, 1H) |

TABLE 2-20-continued

| Compound No. | δ value (ppm, solvent: CDCl₃, internal standard substance: TMS) |
|---|---|
| 317 | 2.85 (t, 2H), 3.37 (s, 3H), 3.96 (q, 2H), 4.62 (s, 2H), 6.58 (brs, 1H), 7.26-7.93 (m, 7H), 8.64 (s, 1H) |
| 318 | 2.90 (t, 2H), 3.38 (s, 3H), 3.94 (q, 2H), 4.60 (s, 2H), 6.96-7.69 (m, 8H), 8.62 (s, 1H) |
| 319 | 2.83 (t, 2H), 3.37 (s, 3H), 3.96 (q, 2H), 4.63 (s, 2H), 6.66 (brs, 1H), 7.21-7.89 (m, 6H), 8.62 (s, 1H) |
| 320 | 2.86 (t, 2H), 3.35 (s, 3H), 3.95 (q, 2H), 4.60 (s, 2H), 6.60 (brs, 1H), 7.21-8.02 (m, 7H), 8.64 (s, 1H) |
| 321 | 2.84 (t, 2H), 3.39 (s, 3H), 3.94 (q, 2H), 4.65 (s, 2H), 6.76 (brs, 1H), 7.21-8.22 (m, 7H), 8.70 (s, 1H) |
| 322 | 2.82 (t, 2H), 3.40 (s, 3H), 3.96 (q, 2H), 4.67 (s, 2H), 6.78 (brs, 1H), 7.21-8.36 (m, 7H), 8.66 (s, 1H) |
| 323 | 2.88 (t, 2H), 3.36 (s, 3H), 3.92 (q, 2H), 4.61 (s, 2H), 6.73 (brs, 1H), 7.18-8.12 (m, 7H), 8.72 (s, 1H) |

TABLE 2-21

| Compound No. | δ value (ppm, solvent: CDCl₃, internal standard substance: TMS) |
|---|---|
| 324 | 2.88 (t, 2H), 3.36 (s, 3H), 3.92 (q, 2H), 4.61 (s, 2H), 6.73 (brs, 1H), 7.18-8.12 (m, 7H), 8.72 (s, 1H) |
| 325 | 2.70 (s, 3H), 2.88 (t, 2H), 3.35 (s, 3H), 3.95 (q, 2H), 4.59 (s, 2H), 6.38 (brs, 1H), 7.15-7.61 (m, 7H), 8.73 (s, 1H) |
| 326 | 2.49 (s, 3H), 2.88 (t, 2H), 3.34 (s, 3H), 3.94 (q, 2H), 4.60 (s, 2H), 6.48 (brs, 1H), 7.22-8.01 (m, 7H), 8.63 (s, 1H) |
| 327 | 2.66 (s, 3H), 2.86 (t, 2H), 3.38 (s, 3H), 3.92 (q, 2H), 4.62 (s, 2H), 6.64 (brs, 1H), 7.18-7.82 (m, 6H), 8.68 (s, 1H) |
| 328 | 2.87 (t, 2H), 3.50 (s, 3H), 3.75 (s, 3H), 3.96 (q, 2H), 4.60 (s, 2H), 6.59 (brs, 1H), 7.30-7.89 (m, 7H), 8.78 (s, 1H) |
| 329 | 2.87 (t, 2H), 3.32 (s, 3H), 3.75 (s, 3H), 3.93 (q, 2H), 4.53 (s, 2H), 6.62 (brs, 1H), 7.00-7.82 (m, 7H), 8.59 (s, 1H) |
| 330 | 2.84 (t, 2H), 3.31 (s, 3H), 3.95 (q, 2H), 7.20-7.90 (m, 7H), 8.55 (s, 1H), 8.71 (s, 1H) |
| 331 | 2.83 (t, 2H), 3.41 (s, 3H), 4.00 (q, 2H), 4.70 (s, 2H), 7.14-7.44 (m, 4H), 7.85-9.17 (m, 4H) |
| 332 | 2.46 (s, 3H), 2.84 (t, 2H), 3.32 (s, 3H), 3.95 (q, 2H), 4.61 (s, 2H), 6.64 (brs, 1H), 7.26-8.09 (m, 7H), 8.61 (s, 1H) |
| 333 | 2.86 (t, 2H), 3.20 (s, 3H), 3.92 (q, 2H), 4.56 (s, 2H), 6.68 (brs, 1H), 7.24-8.03 (m, 12H), 8.67 (s, 1H) |
| 334 | 2.88 (t, 2H), 3.22 (s, 3H), 3.95 (q, 2H), 4.52 (s, 2H), 6.60 (brs, 1H), 7.08-8.01 (m, 11H), 8.69 (s, 1H) |
| 335 | 2.85 (t, 2H), 3.22 (s, 3H), 3.92 (q, 2H), 4.58 (s, 2H), 6.80 (brs, 1H), 7.18-8.05 (m, 11H), 8.66 (s, 1H) |
| 336 | 2.85 (t, 2H), 3.24 (s, 3H), 3.92 (q, 2H), 4.54 (s, 2H), 6.74 (brs, 1H), 7.00-7.96 (m, 11H), 8.67 (s, 1H) |
| 337 | 2.88 (t, 2H), 3.24 (s, 3H), 2.97 (q, 2H), 4.56 (s, 2H), 7.14-7.37 (m, 5H), 7.91-8.69 (m, 7H) |
| 338 | 2.83 (t, 2H), 3.34 (s, 3H), 3.97 (q, 2H), 4.64 (s, 2H), 6.90 (brs, 1H), 7.25-7.95 (m, 6H), 8.75 (s, 1H) |
| 339 | 2.86 (t, 2H), 3.35 (s, 3H), 3.92 (q, 2H), 4.59 (s, 2H), 4.83 (s, 2H), 6.74 (brs, 1H), 7.13-7.85 (m, 12H), 8.62 (s, 1H) |

TABLE 2-22

| Compound No. | δ value (ppm, solvent: CDCl₃, internal standard substance: TMS) |
|---|---|
| 340 | 2.85 (t, 2H), 3.31 (s, 3H), 3.93 (q, 2H), 4.58 (s, 2H), 4.95 (s, 2H), 6.66 (brs, 1H), 7.15-7.83 (m, 12H), 8.58 (s, 1H) |
| 341 | 2.45 (s, 3H), 2.66 (s, 3H), 2.84 (t, 2H), 3.43 (s, 3H), 3.94 (q, 2H), 4.60 (s, 2H), 7.25-8.00 (m, 6H), 8.68 (s, 1H) |
| 342 | 2.86 (t, 2H), 3.94 (q, 2H), 7.30-8.91 (m, 11H) |

TABLE 2-22-continued

| Compound No. | δ value (ppm, solvent: CDCl₃, internal standard substance: TMS) |
|---|---|
| 343 | 1.50 (d, 3H), 2.90 (dd, 2H), 4.67-4.98 (m, 1H), 5.93 (brs, 1H), 7.16-7.76 (m, 7H), 8.70 (s, 1H) |
| 344 | 1.48 (d, 3H), 2.91 (dd, 2H), 4.65-4.97 (m, 1H), 6.16 (d, 1H), 7.09-7.90 (m, 6H), 8.63 (s, 1H) |
| 345 | 1.53 (d, 3H), 2.93 (dd, 2H), 4.60-4.96 (m, 1H), 6.14 (d, 1H), 7.26-7.62 (m, 5H), 7.81-7.98 (m, 1H), 8.64 (s, 1H) |
| 346 | 1.51 (d, 3H), 2.90 (dd, 2H), 4.63-4.93 (m, 1H), 6.98-7.69 (m, 6H), 8.61 (s, 1H) |
| 347 | 2.48 (d, 3H), 2.90 (dd, 2H), 4.80 (m, 1H), 5.81 (d, 1H), 7.09-7.79 (m, 6H), 8.64 (s, 1H) |
| 348 | 1.51 (d, 3H), 2.92 (dd, 2H), 4.73-4.88 (m, 1H), 5.97 (d, 1H), 7.27-7.63 (m, 6H), 8.70 (s, 1H) |
| 349 | 1.50 (d, 3H), 2.91 (dd, 2H), 4.67-4.93 (m, 1H), 5.94 (d, 1H), 7.23-7.88 (m, 6H), 8.77 (s, 1H) |
| 350 | 1.53 (d, 3H), 2.90 (dd, 2H), 4.65-4.92 (m, 1H), 7.20-8.23 (m, 7H), 8.59 (s, 1H) |
| 351 | 1.53 (d, 3H), 2.94 (dd, 2H), 4.69-4.98 (m, 1H), 6.53 (d, 1H), 7.26-7.61 (m, 4H), 8.04-8.18 (m, 2H), 8.62 (s, 1H) |
| 352 | 1.51 (d, 3H), 2.92 (dd, 2H), 4.06 (s, 3H), 4.62-4.98 (m, 1H), 5.93 (d, 1H), 7.05-7.63 (m, 6H), 8.69 (s, 1H) |
| 353 | 1.49 (d, 3H), 2.86 (dd, 2H), 4.08 (s, 3H), 4.80 (m, 1H), 5.88 (d, 2H), 7.04-7.61 (m, 6H), 8.70 (s, 1H) |
| 354 | 1.52 (d, 3H), 2.70 (s, 3H), 2.92 (dd, 2H), 4.81 (brs, 1H), 6.16 (brs, 1H), 7.26-7.61 (m, 6H), 8.73 (s, 1H) |
| 355 | 1.52 (d, 3H), 2.92 (dd, 2H), 4.62-4.97 (m, 1H), 6.02 (d, 1H), 7.38-7.79 (m, 5H), 8.63 (s, 1H) |

TABLE 2-23

| Compound No. | δ value (ppm, solvent: CDCl₃, internal standard substance: TMS) |
|---|---|
| 356 | 2.15 (s, 3H), 2.75 (t, 3H), 3.74 (q, 2H), 5.28 (brs, 1H), 7.19-7.43 (m, 5H), 8.29 (s, 1H) |
| 357 | 2.76 (t, 2H), 3.76 (q, 2H), 5.93 (brs, 1H), 7.23-7.46 (m, 5H), 8.30 (s, 1H) |
| 358 | 2.74 (t, 2H), 3.60 (q, 2H), 5.44 (brs, 1H), 6.40 (s, 1H), 7.23-7.45 (m, 5H), 8.37 (s, 1H) |
| 359 | 1.24 (d, 3H), 2.33 (s, 3H), 2.55 (d, 2H), 4.68-4.99 (m, 1H), 6.29 (s, 1H), 7.25-7.60 (m, 4H), 8.06 (s, 1H) |
| 360 | 2.47 (s, 3H), 2.79 (t, 2H), 3.78 (q, 2H), 5.74 (brs, 1H), 7.44-7.61 (m, 3H), 8.38 (s, 1H) |
| 361 | 2.34 (s, 3H), 2.47 (s, 3H), 2.79 (t, 2H), 3.41 (s, 3H), 3.76 (q, 2H), 4.57 (s, 2H), 5.80 (brs, 1H), 7.06-7.34 (m, 3H), 8.39 (s, 1H) |
| 362 | 2.46 (s, 3H), 2.80 (t, 2H), 3.41 (s, 3H), 3.76 (q, 2H), 4.60 (s, 2H), 5.85 (brs, 1H), 7.17-7.45 (m, 4H), 8.39 (s, 1H) |
| 363 | 2.04 (s, 3H), 2.78 (t, 2H), 3.38 (s, 3H), 3.77 (q, 2H), 4.58 (s, 2H), 5.43 (brs, 1H), 7.18-7.45 (m, 4H), 8.24 (s, 1H) |
| 364 | 2.08 (s, 3H), 2.79 (t, 2H), 3.79 (q, 2H), 5.26 (brs, 1H), 7.27-7.68 (m, 4H), 8.28 (s, 1H) |
| 365 | 2.10 (s, 3H), 2.78 (t, 2H), 3.40 (s, 2H), 3.80 (q, 2H), 6.10 (brs, 1H), 7.18-7.70 (m, 4H), 8.32 (s, 1H) |
| 366 | 2.82 (t, 2H), 3.40 (s, 3H), 3.78 (q, 2H), 4.58 (s, 2H), 6.02 (brs, 1H), 7.22-7.45 (m, 4H), 8.30 (s, 1H) |
| 367 | 2.82 (t, 2H), 3.78 (q, 2H), 6.04 (brs, 1H), 7.27-7.72 (m, 4H), 8.30 (s, 1H) |
| 368 | 2.80 (t, 2H), 3.47 (brs, 2H), 3.77 (q, 2H), 5.36 (brs, 1H), 7.33-7.68 (m, 4H), 8.07 (s, 1H) |
| 369 | 2.92 (s, 3H), 2.92 (t, 2H), 3.96 (q, 2H), 7.39-7.75 (m, 5H), 8.12 (s, 1H) |
| 370 | 2.80 (t, 2H), 3.89 (q, 2H), 7.34-7.83 (m, 5H), 8.41 (s, 1H) |
| 371 | 2.52 (s, 3H), 2.81 (t, 2H), 3.96 (q, 2H), 6.70 (brs, 1H), 7.42-7.58 (m, 4H), 8.40 (s, 1H) |

TABLE 2-24

| Compound No. | δ value (ppm, solvent: CDCl$_3$, internal standard substance: TMS) |
|---|---|
| 372 | 2.70 (t, 2H), 3.63 (q, 2H), 3.98 (s, 2H), 7.19-7.35 (m, 10H), 7.91 (s, 1H) |
| 373 | 2.66 (t, 2H), 3.62 (q, 2H), 5.20 (brs, 1H), 7.09-7.45 (m, 10H), 8.36 (d, 1H) |
| 374 | 1.65 (dd, 3H), 2.75 (t, 2H), 3.82 (q, 2H), 5.92-6.17 (m, 2H), 7.22-7.48 (m, 5H), 8.45 (s, 1H) |
| 375 | 1.70 (dd, 3H), 2.80 (t, 2H), 3.80 (q, 2H), 5.50-6.20 (m, 1H), 6.05 (brs, 1H), 7.15-7.38 (m, 5H), 8.50 (s, 1H) |
| 376 | 1.65 (dd, 3H), 2.75 (t, 2H), 3.71 (q, 2H), 5.50-6.25 (m, 1H), 5.90 (brs, 1H), 7.19-7.44 (m, 5H), 8.55 (s, 1H) |
| 377 | 1.68 (dd, 3H), 2.81 (t, 2H), 3.80 (q, 2H), 5.89 (dq, 1H), 5.91 (brs, 1H), 7.44-7.61 (m, 3H), 8.54 (s, 1H) |
| 378 | 2.75 (t, 2H), 3.75 (q, 2H), 7.30 (s, 5H), 7.72 (t, 1H), 8.08 (s, 1H), 8.22 (s, 1H) |
| 379 | 2.84 (t, 2H), 3.89 (q, 2H), 5.61 (t, 1H), 6.41 (d, 1H), 7.10 (d, 1H), 7.23-7.47 (m, 5H), 8.39 (s, 1H) |
| 380 | 2.88 (t, 2H), 3.34 (s, 3H), 3.94 (q, 2H), 4.59 (s, 2H), 7.25-7.39 (m, 7H), 8.43 (s, 1H), 9.00 (brs, 1H) |
| 381 | 1.45 (d, 3H), 1.70 (dd, 3H), 2.78 (dd, 2H), 4.35-4.68 (m, 1H), 5.40-6.20 (m, 2H), 5.85 (brs, 1H), 7.17-7.47 (m, 5H), 8.45 (s, 1H) |
| 382 | 1.44 (d, 3H), 1.80 (d, 3H), 2.82 (t, 2H), 4.40-4.72 (m, 1H), 5.65 (d, 1H), 6.13 (q, 1H), 7.26-7.62 (m, 3H), 8.53 (s, 1H) |
| 383 | 1.44 (d, 3H), 1.85 (d, 3H), 2.82 (t, 2H), 4.40-4.72 (m, 1H), 5.48 (q, 1H), 5.70 (d, 1H), 7.45-7.74 (m, 3H), 8.54 (s, 1H) |
| 384 | 1.54 (d, 3H), 2.95 (dd, 2H), 4.68-4.99 (m, 1H), 7.16-7.67 (m, 4H), 8.57 (dd, 1H), 8.88 (s, 1H), 9.01 (dd, 1H) |
| 385 | 1.43 (d, 3H), 2.45 (s, 3H), 2.80 (d, 2H), 4.38-4.64 (m, 1H), 5.48 (brs, 1H), 7.44-7.62 (m, 3H), 8.36 (s, 1H) |
| 386 | 1.42 (d, 3H), 2.57 (s, 3H), 2.78 (d, 2H), 4.32-4.62 (m, 1H), 5.50 (d, 1H), 7.45-7.61 (m, 3H), 8.30 (s, 1H) |
| 387 | 1.34 (d, 3H), 2.50 (s, 3H), 2.80 (d, 2H), 4.37-4.62 (m, 1H), 5.57 (d, 1H), 7.46-7.62 (m, 3H), 8.36 (s, 1H) |

TABLE 2-25

| Compound No. | δ value (ppm, solvent: CDCl$_3$, internal standard substance: TMS) |
|---|---|
| 388 | 1.34 (d, 3H), 2.80 (d, 2H), 4.37-4.62 (m, 1H), 5.57 (d, 1H), 7.46-7.62 (m, 3H), 8.36 (s, 1H) |
| 389 | 1.43 (d, 3H), 2.46 (s, 3H), 2.74 (dd, 2H), 4.42-4.59 (m, 1H), 5.55 (d, 1H), 7.22-7.47 (m, 5H), 8.34 (s, 1H) |

Example 2

Pharmaceutical Agent Examples

Pharmaceutical Agent Example 1

Emulsion 10 parts of the compound of the present invention were dissolved in 45 parts of 1,2-dimethyl-4-ethylbenzene and 35 parts of 1-methyl-2-pyrrolidinone. Thereafter, 10 parts of SORPOL 3005X (the trade name of a surfactant manufactured by TOHO Chemical Industry Co., Ltd.) were added to the solution, and the mixed solution was then stirred and blended, so as to obtain a 10% emulsion.

Pharmaceutical Agent Example 2

Wettable Powder 10 parts of the compound of the present invention were added to a mixture of 2 parts of sodium lauryl sulfate, 4 parts of sodium lignosulfonate, 20 parts of white carbon and 64 parts of clay. The obtained mixture was stirred and blended using a juice mixer, so as to obtain a 10% wettable powder.

Pharmaceutical Agent Example 3

Granule 2 parts of sodium dodecylbenzenesulfonate, 2 parts of carboxymethyl cellulose, 2 parts of sodium lauryl sulfate, 10 parts of bentonite and 79 parts of clay were added to 5 parts of the compound of the present invention. The obtained mixture was fully stirred and blended. Thereafter, an appropriate amount of water was added to the resultant, and the mixture was further stirred. The reaction product was granulated using a granulator, followed by circulation drying, so as to obtain a 5% granule.

Pharmaceutical Agent Example 4

Powdery Agent 1 part of the compound of the present invention was dissolved in 2 parts of soybean oil. Thereafter, 5 parts of white carbon, 0.3 parts of isopropyl acid phosphate (PAP) and 91.7 parts of clay were added to the mixture, and the obtained mixture was then stirred and blended using a juice mixer, so as to obtain a 1% powdery agent.

Pharmaceutical Agent Example 5

Flowable Agent 20 parts of the compound of the present invention were mixed with 20 parts of water comprising 2 parts of polyoxyethylene alkyl ether, 1 part of sodium dialkyl sulfosuccinate and 0.2 parts of 1,2-benzisothiazoline-3-one. The obtained mixture was subjected to wet milling using Dinomill, and the reaction product was then mixed with 60 parts of water comprising 8 parts of propylene glycol and 0.32 parts of xanthan gum, so as to obtain a 20% water suspension.

Pharmaceutical Agent Example 6

Granulated Wettable Powder 2 parts of sodium lauryl sulfate, 3 parts of sodium alkylnaphthalene sulfonate, 5 parts of dextrin, 20 parts of white carbon and 50 parts of clay were added to 20 parts of the compound of the present invention. The obtained mixture was fully stirred and blended. Thereafter, an appropriate amount of water was added to the resultant, and the obtained mixture was further stirred. The reaction product was granulated using a granulator, followed by circulation drying, so as to obtain a 20% granulated wettable powder.

Example 3

Effect Tests (1) Test of Examining Control Effect on *Phytophthora infestans*

Using a spray gun, an agent solution prepared by adjusting a 10% wettable powder of each sample compound to 125 ppm (hereinafter referred to as a "sample agent solution") was sprayed to potted tomato plants (variety: Sugar Lamp, 4.5 leave stage) in a concentration of 15 ml/pot. One day after the spraying, a zoospore suspension of *Phytophthora infestans* (zoospore concentration: $1.0\times10^4$ cells/ml) was applied to the plants by spray inoculation. The plants were left at 21° C. under wet chamber conditions for 1 day, and were then left in a greenhouse for 3 days, so that they were fully infected with the aforementioned disease. Thereafter, the disease level of each leaf was examined, and a preventive value was calculated using the following formula.

Calculation of Preventive Value:

$$\text{Preventive value}=\{(\text{untreated lesion area rate}-\text{treated lesion area rate})/\text{untreated lesion area rate}\}\times100$$

Using the thus calculated preventive value, the control effect of each compound was determined in accordance with the following standards. The results are shown in Table 3.

High control effect: 100%≥preventive value≥60%

Low control effect: 60%>preventive value≥0%

TABLE 3

Test of control effect on *Phytophthora infestans*
Control effect determination result

| Determination of control effect | Table 1. Compound No. |
|---|---|
| Control effect: high | 2, 7, 8, 10, 11, 17, 21, 23, 25, 32-51, 55, 58, 60-63, 65, 67-75, 84, 85, 87, 89, 91-93, 96, 97, 99-105, 107, 110, 115-121, 125-128, 130, 131, 133, 134, 139-141, 142-148, 151, 153, 154, 156, 161, 163, 164, 166, 168-172, 174, 177-180, 183, 184, 193, 195, 199, 200, 204-208, 210-212, 215, 216, 223-227, 230-233, 235, 237-241, 243-247, 249, 250, 255-260, 264-266, 271-276, 278, 279, 283, 285, 286, 290, 292, 293, 296, 298, 299, 306, 311, 315-319, 323, 325, 329, 330, 343, 355-357, 361-363, 365, 366, 375, 376, 380, 381 |
| Control effect: low | 1, 3-6, 9, 12-16, 18-20, 22, 24, 26-31, 52-54, 56, 57, 59, 64, 66, 76-83, 86, 88, 90, 94, 95, 98, 106, 108, 109, 111-114, 122-124, 129, 132, 135-138, 149, 150, 152, 155, 157-160, 162, 165, 167, 173, 175, 176, 181, 182, 185-192, 194, 196-198, 201-203, 209, 213, 214, 217-222, 228, 229, 234, 236, 242, 248, 251-254, 261, -263, 267-270, 277, 280-282, 284, 287-289, 291, 294, 295, 297, 300-305, 307-310, 312-314, 320-322, 324, 326-328, 331-342, 344-354, 358-360, 364, 367-374, 377-379, 382-389 |

(2) Test of Examining Control Effect on *Pseudoperonospora cubensis*

Using a spray gun, an agent solution prepared by adjusting a 10% wettable powder of each sample compound to 125 ppm (hereinafter referred to as a "sample agent solution") was sprayed to potted cucumber plants (variety: Sagamihanjiro, 2.5 leave stage) in a concentration of 15 ml/pot. One day after the spraying, a conidial suspension of *Pseudoperonospora cubensis* (conidial concentration: $1.0\times10^4$ cells/ml) was applied to the plants by spray inoculation. After completion of the inoculation, the plants were left at 21° C. under wet chamber conditions for 1 day, and were then left in a greenhouse for 3 days, so that they were fully infected with the aforementioned disease. Thereafter, the disease level on each leaf was compared with that on an untreated leaf, and the control effect of each compound was determined in the same manner as in Example 3(1). The results are shown in Table 4.

TABLE 4

Test of control effect on *Pseudoperonospora cubensis*
Control effect determination result

| Determination of control effect | Table 1. Compound No. |
|---|---|
| Control effect: high | 2, 3, 5, 7-27, 29-51, 52-56, 58, 60-76, 78-137, 139-148, 151-159, 161-185, 187-219, 221-254, 256-257, 258, 259, 260, 261, 262, 263-300, 303-357, 360-368, 374-377, 380-389 |
| Control effect: low | 1, 4, 6, 28, 57, 59, 138, 149, 150, 160, 186, 220, 301, 302, 358, 359, 369-373, 378, 379 |

(3) Test of Examining Control Effect on *Sphaerotheca fuliginea*

Using a spray gun, an agent solution prepared by adjusting a 10% wettable powder of each sample compound to 125 ppm (hereinafter referred to as a "sample agent solution") was sprayed to potted cucumber plants (variety: Sagamihanjiro, 2nd leave stage) in a concentration of 15 ml/pot. One day after the spraying, a conidial suspension of *Sphaerotheca fuliginea* (conidial concentration: $1.0\times10^5$ cells/ml) was applied to the plants by spray inoculation. The plants were left in a greenhouse for 14 days, so that they were fully infected with the aforementioned disease. Thereafter, the disease level on each leaf was compared with that on an untreated leaf, and the control effect of each compound was determined in the same manner as in Example 3(1). The results are shown in Table 5.

TABLE 5

Test of control effect on *Sphaerotheca fuliginea*
Control effect determination result 1

| Determination of control effect | Table 1. Compound No. |
|---|---|
| Control effect: high | 2, 3, 5-20, 22-27, 29, 32-=56, 61-63, 65, 67, 68, 70-76, 78-80, 82, 83, 85-91, 93, 94, 96-105, 107, 109-111, 113-121, 127, 128, 130, 131, 133, 134, 136, 137, 139-148, 151, 154, 156-159, 163-184, 186, 189, 193-201, 204, 205, 207, 208, 210-217, 219-227, 229-239, 241-253, 255-256, 257-275, 277-279, 281-298, 300, 304, 306-323, 325, 326, 328, 329, 343-356, 358, 360-368, 374-377, 379-389 |
| Control effect: low | 1, 4, 21, 28, 30, 31, 57-60, 64, 66, 69, 77, 81, 84, 92, 95, 106, 108, 112, 122-126, 129, 132, 135, 138, 149, 150, 152, 153, 155, 161, 162, 185, 187, 188, 190-192, 202, 203, 206, 209, 218, 228, 254, 276, 280, 299, 301-303, 305, 324, 327, 330-342, 357, 359, 369-373, 378 |

(4) Test of Examining Effect on *Aphis gossypii*

A cucumber leaf section having a diameter of 3 cm was placed on a wet sponge in a plastic cup. Thereafter, five female adults of *Aphis gossypii* were released into the plastic cup, and they were then left at rest overnight. Thereafter, the number of new-born larvae was counted. 0.4 ml each of an agent solution prepared by diluting a 10% wettable powder of each compound shown in Table 1 to a concentration of 250 ppm was sprayed thereto. Two days later, the number of deaths was counted, and the mortality rate was then calculated. A mortality rate of 95% or more was determined to be A, a mortality rate of 80% or more to less than 95% was determined to be B, and a mortality rate of 60% or more to less than 80% was determined to be C. The results are shown in Table 6.

TABLE 6

Test of effect on *Aphis gossypii* Effect determination result

| Determination | Table 1. Compound No. |
| --- | --- |
| A | 3, 6, 7, 10, 11, 14, 19, 21, 44-49, 53, 54, 87, 88, 91, 99, 100, 102, 103, 107, 108, 113, 133, 137, 139-145, 147-151, 153, 154, 158, 161, 180, 181, 197, 206-208, 229-235, 237, 239-246, 248-252, 255-262, 265-268, 270-275, 277-282, 285-290, 292, 294, 296-300, 304, 306, 312-321, 323, 325, 326, 328, 331, 333, 335, 337, 343-349, 351-353, 355, 360-362, 365, 366, 374, 376, 377, 380, 382-389 |
| B | 1, 8, 12, 13, 17, 22, 23, 32, 89, 93, 106, 122, 130, 169, 170, 178, 204, 205, 211, 236, 238, 247, 254, 276, 283, 284, 310, 336, 350, 354, 367 |
| C | 2, 9, 15, 16, 25, 31, 33-37, 64, 67, 74, 83, 86, 90, 94, 98, 104, 109, 117, 124, 152, 155, 159, 160, 163, 168, 182, 184, 185, 187, 190, 194, 199, 210, 212, 221, 224, 253, 263, 264, 269, 307, 309, 311, 324, 334, 363, 364, 375, 381 |

(5) Test of Examining Effect on *Tetranychus urticae* Female Adults

A kidney bean leaf section having a diameter of 3 cm was placed on a wet sponge in a plastic cup. Thereafter, ten female adults of *Tetranychus urticae* were released into the plastic cup. 0.4 ml each of an agent solution prepared by diluting a 10% wettable powder of each compound shown in Table 1 to a concentration of 250 ppm was sprayed thereto. Two days later, the number of deaths was counted, and the mortality rate was then calculated. A mortality rate of 95% or more was determined to be A, a mortality rate of 80% or more to less than 95% was determined to be B, and a mortality rate of 60% or more to less than 80% was determined to be C. The results are shown in Table 7.

TABLE 7

Test of effect on *Tetranychus urticae* female adults Effect determination result

| Determination | Table 1. Compound No. |
| --- | --- |
| A | 51, 95, 106-109, 113, 124, 133, 136, 139, 153, 181, 240, 249, 259, 262, 271, 273, 277, 278, 281-283, 285, 286, 288-290, 296, 297, 304, 331, 333, 337, 344-347, 350-353, 355, 362, 376, 382-387 |
| B | 188, 206, 232, 233, 241, 246, 253, 258, 348, 349, 356 |
| C | 27, 29, 38, 45, 64, 67, 83, 84, 88, 98, 102, 126, 127, 155, 182, 205, 226, 238, 263, 264, 267, 360 |

(6) Test of Examining Effect on *Tetranychus urticae* Eggs

A kidney bean leaf section having a diameter of 3 cm was placed on a wet sponge in a plastic cup. Thereafter, ten female adults of *Tetranychus urticae* were released into the plastic cup, and they were then allowed to oviposit under a room temperature overnight. Thereafter, the released female adults were removed. 0.4 ml each of an agent solution prepared by diluting a 10% wettable powder of each compound shown in Table 1 to a concentration of 250 ppm was sprayed. Six days later, the number of unhatched eggs was counted, and an ovicidal rate was calculated. An ovicidal rate of 95% or more was determined to be A, an ovicidal rate of 80% or more to less than 95% was determined to be B, and an ovicidal rate of 60% or more to less than 80% was determined to be C. The results are shown in Table 8.

TABLE 8

Test of effect on *Tetranychus urticae* eggs Effect determination result

| Determination | Table 1. Compound No. |
| --- | --- |
| A | 113, 235, 238, 241, 249, 259, 262, 277, 285, 288, 289, 350, 355, 376, 377, 382, 384, 385 |
| B | 107, 109, 232, 233, 239, 245, 246, 257, 286, 348, 356 |
| C | 10, 16, 19, 20, 22, 24, 30, 38, 82, 95, 231, 240, 247, 248, 253, 258, 267, 269, 283 |

(7) Test of Examining Effect on *Spodptera litura*

A Chinese cabbage leaf section having a diameter of 3 cm was immersed in an agent solution prepared by diluting a 10% wettable powder of each compound shown in Table 1 to a concentration of 500 ppm, and it was then subjected to air drying. Thereafter, the Chinese cabbage leaf was placed in a plastic petri dish, and 10 third-instar larvae of *Spodptera litura* were released therein. Two days after the treatment, the number of deaths was counted, and the mortality rate was then calculated. A mortality rate of 95% or more was determined to be A, a mortality rate of 80% or more to less than 95% was determined to be B, and a mortality rate of 60% or more to less than 80% was determined to be C. The results are shown in Table 9.

TABLE 9

Test of effect on *Spodptera litura* Effect determination result

| Determination | Table 1. Compound No. |
| --- | --- |
| A | 99, 102, 133, 139, 143, 144, 238, 249, 250, 257, 258, 275, 277, 278, 285, 286, 288, 289, 331, 337, 343-345, 347, 348, 352, 353, 355, 374, 382 |
| B | 27, 279, 282, 297, 375, 377, 384, 387 |
| C | 13, 14, 16, 19, 52, 55, 112, 113, 121, 130, 137, 154, 177, 224, 232, 235, 264, 268, 271, 273, 290, 296, 317, 319, 332, 336, 360, 380, 381 |

(8) Test of Examining Effect on *Meloidogyne incognita*

1 ml of a diluted solution prepared by diluting a 10% wettable powder of each compound shown in Table 1 to a concentration of 5000 ppm was placed in a test tube. 9 ml of distilled water containing approximately 200 roundworms of *Meloidogyne incognita* was added to the test tube, and it was then left at rest at a room temperature for 48 hours. Subsequently, the agent-treated roundworms were washed out, and the life or death thereof was determined under a microscope. Then, a rate of killing roundworms was calculated. A mortality rate of 95% or more was determined to be A, and a mortality rate of 80% or more to less than 95% was determined to be B. The results are shown in Table 10.

TABLE 10

Test of effect on *Meloidogyne incognita* Effect determination result

| Determination | Table 1. Compound No. |
| --- | --- |
| B | 10-14 |

INDUSTRIAL APPLICABILITY

Since the novel compound represented by the general formula [I] of the present invention particularly exhibits excellent control activity on pests that damage agricultural and horticultural plants, such as pathogens, insects, mites and nematodes, it is extremely useful as a novel agricultural chemical.

The invention claimed is:

1. A compound represented by the following general formula [I]:

[Formula 1]

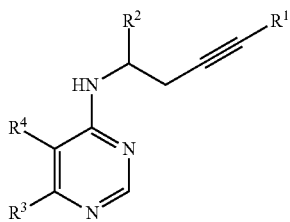

[wherein
R$^1$ is selected from among
a) a mono- or bi-cyclic ring which may contain 0 to 3 heteroatoms selected from the group consisting of phenyl, benzyl, oxazolyl, isoxazolyl, furyl, benzofuryl, isobenzofuryl, dihydrobenzofuryl, thiazolyl, isothiazolyl, naphthyl, pyrimidinyl, pyrazinyl, quinoxalyl, quinazolinyl, pyridyl, quinolyl, isoquinolyl, benzothiazolyl, benzoisothiazolyl, pyrrolyl, indolyl, isoindolyl, benzoxazolyl, benzisoxazolyl, thienyl, benzothienyl, imidazolyl, benzimidazolyl, pyrazolyl, and pyridonyl,
b) linear or branched alkyl containing 1 to 6 carbon atoms, linear or branched alkenyl containing 2 to 8 carbon atoms, linear or branched alkynyl containing 2 to 8 carbon atoms, cycloalkyl containing 3 to 8 carbon atoms, or cycloalkenyl containing 3 to 8 carbon atoms,
c) —SiR$^5$R$^6$R$^7$ (wherein R$^5$, R$^6$ and R$^7$ each represent linear or branched alkyl containing 1 to 6 carbon atoms or phenyl; all of which may be the same substituents, or all of which may be different substituents), and
d) a hydrogen atom, wherein
  in the case of a) or b) above, R$^1$ may be substituted with —C(O)OR, —C(O)R, —R, —OR, —SR, —SO$_2$R, —OC(O)R, —C(O)NHR, —C(O)NR$_2$, —NHSO$_2$R, —NRSO$_2$R, —NHR, —NR$_2$, —NHC(O)R, —NRC(O)R, —NHC(O)OR, —NRC(O)OR, —N(OR)C(O)OR, —NHSO$_2$R, —NRSO$_2$R, —SO$_2$NHR, —SO$_2$NR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), —SiR$^5$R$^6$R$^7$, —OSiR$^5$R$^6$R$^7$ (wherein R$^5$, R$^6$ and R$^7$ each represent linear or branched alkyl containing 1 to 6 carbon atoms or phenyl; two or all of which may be the same substituents, or all of which may be different substituents), haloalkyl, haloalkenyl, haloalkoxy, acylalkoxy, acyloxyalkyl, alkylsulfonylalkyl, siloxyalkyl, hydroxyalkyl, alkoxyalkyl, haloalkoxyalkyl, alkylthioalkyl, dialkoxyacetal, alkoxyalkoxy, cyanoalkyl, halogen, cyano, nitro, amino, hydroxy, pentahalosulfanyl, benzyl, benzyloxy, phenyl, phenoxy, pyridyl, oxazolyl, furyl, thiazolyl, naphthyl, pyrimidinyl, thienyl, benzothiazolyl, benzoxazolyl, benzodioxolyl, imide, formyl (—CHO), carboxyl (—COOH), formamide (—NHCHO), cyclic ether, and cyclic amine, R$^2$ represents a hydrogen atom, —R, —OR, —C(O)OR, —C(O)NHR, —CONR$_2$ (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), hydroxyalkyl, alkoxyalkyl, haloalkoxyalkyl, phenyl, halogen, cyano, haloalkyl, haloalkoxy, or heteroaryl selected from the group consisting of oxazolyl, isoxazolyl, thiazolyl, isothiazolyl, pyrimidinyl, pirazinyl, quinoxalyl, quinazolinyl, quinolyl, isoquinolyl, indolyl, isoindolyl, imidazolyl, pyrazolyl, pyridyl, furyl, thienyl, and pyrrolyl, R$^3$ represents (1) a hydrogen atom, (2) a halogen atom, (3) alkyl containing 1 to 6 carbon atoms substituted with acyloxy represented by 1 to 4 (a linear or branched aliphatic hydrocarbon group containing 1 to 8 carbon atoms)-CO—O— groups, 1 to 13 halogen atoms, or 1 to 4 hydroxyl groups, (4) unsubstituted alkyl containing 1 to 6 carbon atoms, (5) —OR, —SR, or —SO$_2$R (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), or (6) haloalkyl, and R$^4$ represents a hydrogen atom, a halogen atom, alkyl containing 1 to 6 carbon atoms, nitro, amino, phenyl, or benzyl, or alternatively, R$^4$ and R$^3$ together with the carbon atoms on the pyrimidine ring may form a thiophene ring, a pyridine ring, a pyrrole ring, an imidazole ring, a benzene ring, a naphthalene ring, a pyrimidine ring, a furan ring, a pyrazine ring, a pyrazole ring or an oxazole ring.

2. The compound according to claim 1, wherein R$^4$ represents a thiophene ring which is formed together with a carbon atom on a pyrimidine ring as a result of binding with R$^3$.

3. The compound according to claim 1, wherein R$^4$ represents a benzene ring which is formed together with a carbon atom on a pyrimidine ring as a result of binding of with R$^3$.

4. The compound according to claim 1, wherein R$^3$ represents alkyl containing 1 to 6 carbon atoms which is substituted with one or more halogen atoms, and R$^4$ represents a halogen atom.

5. The compound according to claim 1, wherein R$^2$ represents a hydrogen atom, a halogen atom, a cyano group, phenyl, R, —C(O)OR, —C(O)NHR (wherein R represents linear or branched alkyl containing 1 to 8 carbon atoms, linear or branched alkenyl containing 2 to 8 carbon atoms, linear or branched alkynyl containing 2 to 8 carbon atoms, or cycloalkyl containing 3 to 8 carbon atoms), hydroxyalkyl, alkoxyalkyl, or heteroaryl selected from the group consisting of oxazolyl, isoxazolyl, thiazolyl, isothiazolyl, pyrimidinyl, pirazinyl, quinoxalyl, quinazolinyl, quinolyl, isoquinolyl, indolyl, isoindolyl, imidazolyl, pyrazolyl, pyridyl, furyl, thienyl, and pyrrolyl.

6. The compound according to claim 1, wherein R$^1$ is selected from a mono- or bi-cyclic ring which may contain 0 to 3 heteroatoms selected from the group consisting of phenyl, oxazolyl, furyl, thiazolyl, naphthyl, pyrimidinyl, pyridyl, benzothiazolyl, pyrrolyl, benzoxazolyl, pyrazinyl, thienyl, and imidazolyl.

7. A method for producing the compound represented by general formula [I] according to claim 1, which comprises reacting a compound [II] represented by the following general formula [II]:

[Formula 2]

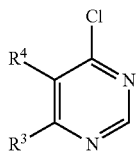

[II]

[wherein R³ and R⁴ have the same meanings as those described in claim 1], with a compound [III] represented by the following general formula [III]:

[Formula 3]

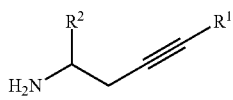

[III]

[wherein R¹ and R² have the same meanings as those described in claim 1], in the presence of a base.

8. A pest control agent comprising, as active ingredient(s), one or two or more of the compounds represented by the general formula [I] according to claim 1.

* * * * *